United States Patent [19]
Vinson et al.

[11] Patent Number: 5,942,433
[45] Date of Patent: Aug. 24, 1999

[54] EXTENSION OF A PROTEIN-PROTEIN INTERACTION SURFACE TO INACTIVATE THE FUNCTION OF A CELLULAR PROTEIN

[75] Inventors: Charles R. Vinson, Silver Spring; Dmitry Krylov, Rockville, both of Md.

[73] Assignee: The United States of America as represented by the Department of Health and Human Services, Washington, D.C.

[21] Appl. No.: 08/690,011

[22] Filed: Jul. 31, 1996

Related U.S. Application Data

[60] Provisional application No. 60/001,654, Jul. 31, 1995, and provisional application No. 60/018,496, May 29, 1996.

[51] Int. Cl.$^6$ ............... C12N 15/11; C12N 15/12; C12N 15/62; C12N 15/63
[52] U.S. Cl. ............... 435/320.1; 536/23.4; 536/23.5
[58] Field of Search ............... 435/69.1, 172.3, 435/320.1; 536/23.4, 23.5

[56] References Cited

U.S. PATENT DOCUMENTS 5,545,563  8/1996  Darlington et al. ................. 435/320.1

OTHER PUBLICATIONS

Gonzalez et al., Nature 337:749–752 (1989).
van Straaten et al., Proc. Natl. Acad. Sci. USA 80:3183–3187 (1983).
Izawa, Biochemica et Biophysica Acta 1216:492–494 (1993).
Nature Biotechnology 15:815 (1997).
Verma et al., Nature 389:239–242 (1997).
"Report and Recommendations of the Panel to Assess the NIH Investment in Research on Gene Therapy," Orkin and Motulsky, Co-chairs, Dec. 7, 1995.
B. Amati et al., 1992, "Transcriptional activation by the human c–Myc oncoprotein in yeast requires interaction with Max", Nature, 359:423–426.
AD Baxevanis et al., 1993, "Interactions of coiled coils in transcription factors: where is the specificity?", Current Opinions in Genetics and Development, 3:278–285.
PH Brown et al., 1994, "Mechanism of action of a dominant–negative mutant of c–Jun", Oncogene, 9:791–799.
EK O'Shea et al., 1991, "X–ray Structure of the GCN4 Leucine Zipper, a Two–Stranded, Parallel Coiled Coil", Science, 254:539–544.
EK O'Shea et al., 1989, "Evidence that the Leucine Zipper is a Coiled Coil", Science, 243:538–542.
EK O'Shea et al., 1989, "Preferential Heterodimer Formation by Isolated Leucine Zippers from Fos and Jun", Science, 245:646–648.

TG Oas et al, 1990, "Secondary Structure of a Leucine Zipper Determined by Nuclear Magnetic Resonance Spectroscopy", Biochemistry, 29:2891–2894.
JC Hu et al., 1990, "Sequence Requirements for Coiled–Coils: Analysis with λ Repressor–GCN4 Leucine Zipper Fusions", Science, 250:1400–1403.
AD Frankel et al., 1991, "Modular Structure of Transcription Factors: Implications for Gene Regulation", Cell, 65:717–719.
EK O'Shea et al., 1992, "Mechanism of Specificity in the Fos–Jun Oncoprotein Heterodimer", Cell, 68:699–708.
K. Kataoka et al., 1995, "Small Maf Proteins Heterodimerize with Fos and May Act as Competitive Repressors of the NF–E2 Transcription Factor", Molecular and Cellular Biology, 15:2180–2190.
C. Muhle–Goll et al., 1994, "The Dimerization Stability of the HLH–LZ Transcription Protein Family is Modulated by the Leucine Zippers: A CD and NMR Study of TFEB and c–Myc", Biochemistry, 33:11296–11306.
M. Billaud et al., 1993, "A dominant–negative mutant of Max that inhibits sequence–specific DNA binding by Myc proteins", Proc. Natl. Acad. Sci. USA, 90:2739–2743.

*Primary Examiner*—Johnny F. Railey, II
*Attorney, Agent, or Firm*—Morgan & Finnegan, L.L.P.

[57] ABSTRACT

Acidic amino acid extensions to multimeric nucleic acid (e.g., DNA or RNA) binding proteins provide novel nucleic acid binding proteins which can inhibit the function of cellular proteins, thereby regulating and controlling cell growth. The nucleic acid binding proteins are engineered to contain a plurality of acidic amino acids appended to the proteins, generally as extensions of the multimerization or dimerization domain at the amino terminus. The acidically extended nucleic acid binding proteins act as potent dominant negatives which were demonstrated to inhibit the activation of endogenous transactivators, such as AP1. The invention provides novel methods to create DNA binding proteins which can specifically and stably heterodimerize with cellular regulatory proteins and control cell growth. Suitable nucleic acid binding proteins for acidic extensions include members of transcription regulatory protein families, e.g., bZIP and HLH proteins, having characteristic leucine zipper motifs and helix-loop-helix motifs, respectively. The amino terminal extensions of the basic regions of nucleic acid binding proteins are comprised of a sequence of amino acid residues, all or some of which are acidic in nature, and produce robust dominant negatives to the native counterpart proteins in the cell. The acidic amino terminal extension affords a unique protein-protein interaction surface and allows stable multimerization or dimerization between a native protein and the acidically extended protein, thereby controlling, via inhibition or inactivation, the functions of cellular protein products of diverse species, including plants, animals, microorganisms, and viruses.

49 Claims, 35 Drawing Sheets

$K_d = 10^{-8}$ M

C/EBP homodimer $10^{-9}$

C/EBP bound to DNA $7 \times 10^{-9}$

C/EBP:C/EBP- F heterodimer $3 \times 10^{-9}$

C/EBP:0heptad- F heterodimer

FIG. 11A

```
                Acidic amphipathic
              α-helical extensions
       4◄──── 3◄──── 2◄──── 1◄──── 0
GGG    LEQRAEE LARENEE LEKEAEE LEQENAE  LEQ  extension
       SNEYRVR RERNNIA VRKSRDK AKQRNVE  TQQ  C/EBP
       DEKYWTR RKKNNVA AKRSRDA RRLKENQ  TQQ  VBP
       ELKRQKR KQSNRES ARRSRLR KQAECEQ  LQQ  GBF1
       defgabc defgabc defgabc defgabc  def  coiled coil
                                             ▲─┐
       bZIP Basic Region                Leucine Zipper
```

```
BamHI
     10             20             30             40             50
      *              *              *              *              *
GG ATCCC CTT CCT ACA CAG CCT GCT GAA GAA GCA GCA CGA AAG AGA GAG GTT CGT
       L   P   T   Q   P   A   E   E   A   A   R   K   R   E   V   R>
      a___CREB (AA 1-341);    NCBI GI: 56005;  CODON_START=1;    a___>

60             70             80             90            100
      *              *              *              *              *
CTA ATG AAG AAC AGG GAA GCA GCA AGA GAA TGT CGT AGA AAG AAG AAA
  L   M   K   N   R   E   A   A   R   E   C   R   R   K   K   K>
      a___CREB (AA 1-341);    NCBI GI: 56005;  CODON_START=1;    a___>

110            120            130            140            150
      *              *              *              *              *
GAA TAT GTG AAA TGT TTA GAG AAC AGA GTG GCA GTG CTT GAA AAC CAA
  E   Y   V   K   C   L   E   N   R   V   A   V   L   E   N   Q>
      a___CREB (AA 1-341);    NCBI GI: 56005;  CODON_START=1;    a___>

160            170            180            190
      *              *              *              *
AAC AAA ACA TTG ATT GAG GAG CTA AAA GAG GCA CTT AAG GAC CTT TAC TGC
  N   K   T   L   I   E   E   L   K   E   A   L   K   D   L   Y   C>
      a___CREB (AA 1-341);    NCBI GI: 56005;  CODON_START=1;    a___>

HindIII
    200            210
      *              *
CAC AAG TCA GAT TAA TTC AAG CTT
  H   K   S   D   *>
      a___CREB (AA 1-3_____>
```

```
900         910         920         930         940
 *           *           *           *           *
CC ATG GAC TAC AAG GAC GAT GAC AAG CAT ATG GCT AGC ATG ACT GGT
   M   D   Y   K   D   D   D   K   H   M   A   S   M   T   G>
   M   D   Y   K   D   D   D   K   H   M   A   S   M   T   G>
   *NcoI*

950         960         970         980         990
 *           *           *           *           *
GGA CAG CAA ATG GGT CGG GAT CCC CTT CCT ACA CAG CCT GCT GAA GAA
 G   Q   Q   M   G   R   D   P   L   P   T   Q   P   A   E   E>
 G   Q   Q   M   G   R   D   P   L   P   T   Q   P   A   E   E>

1000        1010        1020        1030        1040
 *           *           *           *           *
GCA GCA CGA AAG AGA GAG GTT CGT CTA ATG AAG AAC AGG GAA GCA GCA
 A   A   R   K   R   E   V   R   L   M   K   N   R   E   A   A>
 A   A   R   K   R   E   V   R   L   M   K   N   R   E   A   A>

1050        1060        1070        1080        1090
 *           *           *           *           *
AGA GAA TGT CGT AGA AAG AAG AAA GAA TAT GTG AAA TGT TTA GAG AAC
 R   E   C   R   R   K   K   K   E   Y   V   K   C   L   E   N>
 R   E   C   R   R   K   K   K   E   Y   V   K   C   L   E   N>

1100        1110        1120        1130
 *           *           *           *
AGA GTG GCA GTG CTT GAA AAC CAA AAC AAA ACA TTG ATT GAG GAG CTA
 R   V   A   V   L   E   N   Q   N   K   T   L   I   E   E   L>
 R   V   A   V   L   E   N   Q   N   K   T   L   I   E   E   L>

1140        1150        1160        1170        1180
 *           *           *           *           *    *HindIII
AAA GCA CTT AAG GAC CTT TAC TGC CAC AAG TCA GAT TAA TTC AAG CTT
 K   A   L   K   D   L   Y   C   H   K   S   D   *   *
 K   A   L   K   D   L   Y   C   H   K   S   D   *   *
```

```
NcoI                                                     930 *NdeI          940       D10
  *        910  *        920     *                        *                  *         *
CC ATG GAC TAC AAG GAC GAT GAC AAG CAT ATG GCT AGC ATG ACT GGT
   M   D   Y   K   D   D   D   K   H   M   A   S   M   T   G>

970                            990
  950       *        960     *BamHI        *        980     *         *
GGA CAG CAA ATG GGT CGG GAT CCT GAC CTG GAA CAA CGT GCT GAG GAA
 G   Q   Q   M   G   R   D   P   D   L   E   Q   R   A   E   E>

1010       *       1020      *       1030      *       1040      *
 1000      *
CTG GCC CGT GAA AAC GAA CTC GAG GAG CTA AAA GAG GCC GAA GAG CTG GAG
 L   A   R   E   N   E   L   E   E   L   K   E   A   E   E   L   E>

1060      *       1070      *       1080      *       1090      *
 1050      *
CAG GAA CTG GCA GAA CTC ATT GAG GAG CTA AAA AAG CTT GAA AAC CAA
 Q   E   L   A   E   L   I   E   E   L   K   K   L   E   N   Q>

1110      *       1120      *       1130      *       1140      *
 1100      *
AAC AAA ACA TTG GAA GAG CTA AAA GCA CTT AAG GAC CTT TAC TGC
 N   K   T   L   E   E   L   K   A   L   K   D   L   Y   C>

1150      *       1160      *
CAC AAG TCA GAT TAA TTC AAG CTT
 H   K   S   D   *   F   [K   L>
                          HindIII
```

FIG. 19

```
           BamH I    10           20             30           40
              *       *    *   *   *     *   *    *    *   *    *
          GGATCCC AAG GTG GAA CAG TTA TCT CCA GAA GAA GAA GAG AAA AGG AGA
             P  D  K   V   E   Q>
                                L   S   P   E   E   E   E   K   R   R>
                   __1783 TO ____>
                                  __2470_2466 TO 2573 OF HUM FOS _0__b___>

50             60           70           80           90
        *    *    *    *    *    *    *    *    *    *
       ATC CGA AGG GAA AGG AAT AAG ATG GCT GCA GCC AAA TGC CGC AAC CGG
        I   R   R   E   R   N   K   M   A   A   A   K   C   R   N   R>
       __2500_b___b___251_2466 TO 2573 OF HUM FOS _30_b___b___2540b___>

100           110          120          130          140
           *    *    *    *    *    *    *    *    *    *
       AGG AGG GAG CTG ACT GAT ACA CTC CAA GCG GAG ACA GAC CAA CTA GAA
        R   R   E   L   T   D   T   L   Q   A>
                                            E   T   D   Q   L   E>
       ___b_2_2466 TO 2573 OF HUM FOS _570b___>
                                26_2688 TO 3329 OF H_____>

150          160          170          180          190
           *    *    *    *    *    *    *    *    *    *
       GAT GAG AAG TCT GCT TTG CAG ACC GAG ATT GCC AAC CTG CTG AAG GAG
        D   E   K   S   A   L   Q   T   E   I   A   N   L   L   K   E>
       __2710_c____c___272_2688 TO 3329 OF HUM FOS _40_c____c___2750c___>

200          210          220          230          240
               *    *    *    *    *    *    *    *    *    *
       AAG GAA AAA CTA GAG TTC ATC CTG GCA GCT CAC CGA CCT GCC TGC AAG
        K   E   K   L   E   F   I   L   A   A   H   R   P   A   C   K>
       ____c_2760__c____c___2688 TO 3329 OF HUM FOS __2790__c____c__2800_>

250          260
                  *    *    *    *
              ATC CCT GAT TAATTCAAGC TT
               I   P>                           FIG. 20
                                     HindIII
              ___c___>
```

FIG. 22

```
>NdeI                                              >BamHI
 |                                                  |
 |   10          20          30          40        |    50
*|    *     *     *     *     *     *     *     *  |*     *
ATATACAT ATG GCT AGC ATG ACT GGT GGA CAG CAA ATG GGT CGG GAT CCT
         M   A   S   M   T   G   G   Q   Q   M   G   R>
        __a___a___a___a___a_F10___a___a___a___a___a___>
                                                     D   P>
                                                    ___b___>

60          70          80          90
   *     *     *     *     *     *     *     *
GAC CTG GAA CAA CGT GCT GAG GAA CTG GCC CGT GAA AAC GAA GAG CTG
 D   L   E   Q   R   A   E   E   L   A   R   E   N   E   E   L>
___b___b___b___b___4HEPTAD ACIDIC EXTENSION____b___b___b___b___>

>XhoI
                                                |
 100         110         120         130        140
  *     *     *     *     *     *     *     *   |*     *
GAA AAA GAG GCC GAA GAG CTG GAG CAG GAA AAC GCT GAA CTC GAG GCG
 E   K   E   A   E   E   L   E   Q   E   N   A   E   L   E>
___b___b___b___b_4HEPTAD ACIDIC EXTENSION__b___b___b___b___>
                                                         A>
                                                        ___>

150         160         170         180         190
  *     *     *     *     *     *     *     *     *
GAG ACA GAC CAA CTA GAA GAT GAG AAG TCT GCT TTG CAG ACC GAG ATT
 E   T   D   Q   L   E   D   E   K   S   A   L   Q   T   E   I>
___c___c___c___c___c_____C-FOS PROTEIN__c___c___c___c___c___c___>

200         210         220         230         240
  *     *     *     *     *     *     *     *     *     *
GCC AAC CTG CTG AAG GAG AAG GAA AAA CTA GAG TTC ATC CTG GCA GCT
 A   N   L   L   K   E   K   E   K   L   E   F   I   L   A   A>
___c___c___c___c___c_____C-FOS PROTEIN__c___c___c___c___c___c___>

>HindIII
                                          |
 250         260         270             | 280
  *     *     *     *     *     *     *  |  *
CAC CGA CCT GCC TGC AAG ATC CCT GATT AATTCAAGCT T
 H   R   P   A   C   K   I   P>
___c_____C-FOS PROTEIN__c___c___>
```

```
         900  NcoI                                    NdeI
          *
         CC ATG GAC TAC AAG GAC GAC GAT GAC AAG CAT ATG GCT AGC ATG ACT GGT
            M   D   Y   K   D   D   D   D   K   H   M   A   S   M   T   G>
            M   D   Y   K   D   D   D   D   K   H   M   A   S   M   T   G>
           ←─────────── Flag ──────960───────────→  ←────────── φ10
                                    *    BamHI
         GGA CAG CAA ATG GGT CGG GAT CCT GAC CTG GAA CAA CGT GCT GAG GAA
          G   Q   Q   M   G   R   D   P   D   L   E   Q   R   A   E   E>
          G   Q   Q   M   G   R   D   P   D   L   E   Q   R   A   E   E>
                                            1020                4 heptad
                                             *
         CTG GCC CGT GAA AAC GAA GAG CTG GAA AAA GAG GCC GAA GAG CTG GAG
          L   A   R   E   N   E   E   L   E   K   E   A   E   E   L   E>
          L   A   R   E   N   E   E   L   E   K   E   A   E   E   L   E>

XhoI              1080
                                                   *
         CAG GAA AAC GCT GAA CTC GAG GCG GAG ACA GAC CAA CTA GAA GAT GAG
          Q   E   N   A   E   L   E   A   E   T   D   Q   L   E   D   E>
          Q   E   N   A   E   L   E   A   E   T   D   Q   L   E   D   E>
         ──────────────────────→  ←──────────────

AAG TCT GCT TTG CAG ACC GAG ATT GCC AAC CTG CTG AAG GAG AAG GAA
          K   S   A   L   Q   T   E   I   A   N   L   L   K   E   K   E>
          K   S   A   L   Q   T   E   I   A   N   L   L   K   E   K   E>

1140                                            Fos Leucine zipper
          *
         AAA CTA GAG TTC ATC CTG GCA GCT CAC CGA CCT GCC TGC AAG ATC CCT
          K   L   E   F   I   L   A   A   H   R   P   A   C   K   I   P>
          K   L   E   F   I   L   A   A   H   R   P   A   C   K   I   P>

GAT TAA GCTT
          D   *>
          D   *>    HindIII                              FIG. 23
         ─→
```

FIG. 25

```
      >NdeI                                              >BamHI
       |                                                  |
      4090         4100         4110         4120         | 4130
    * | *    *      *      *      *      *      *      *      *
   ATACAT ATG GCT AGC ATG ACT GGT GGA CAG CAA ATG GGT CGG GAT CCC GAC
           M   A   S   M   T   G   G   Q   Q   M   G   R>
           __a___a___a___a___a_F10__a___a___a___a___a___>
                                                    D   P   D>
                                                    __b___b___>

>XhoI
                                  |
      4140         4150         4160         4170         4180
    *      *      *      *      * |*      *      *      *      *
   GAA GAG GAA GAT GAC GAA GAA GAA CTC GAG GAA CTG GAA GAC AGC TTT
    E   E   E   D   D   E   E   E   L   E   E   L   E>
    __b___b___b___b___b_POLY-GLU__b___b___b___b___b___>
                                                    D   S   F>
                                                    __c___c___>

4190         4200         4210         4220         4230
    *      *      *      *      *      *      *      *      *      *
   CAC AGT TTG CGG GAC TCA GTC CCA TCA CTC CAA GGA GAG AAG GCA TCC
    H   S   L   R   D   S   V   P   S   L   Q   G   E   K   A   S>
    __c___c___c___c___c___MAX BHLH DOMAIN_c___c___c___c___c___c___>

4240         4250         4260         4270
    *      *      *      *      *      *      *      *
   CGG GCC CAA ATC CTA GAC AAA GCA ACA GAG TAT ATC CAG TAT ATG CGA
    R   A   Q   I   L   D   K   A   T   E   Y   I   Q   Y   M   R>
    __c___c___c___c___c___MAX BHLH DOMAIN_c___c___c___c___c___c___>

4280         4290         4300         4310         4320
    *      *      *      *      *      *      *      *      *      *
   AGG AAA AAC CAT ACG CAC CAG CAA GAC ATT GAT GAC CTC AAG CGG CAG
    R   K   N   H   T   H   Q   Q   D   I   D   D   L   K   R   Q>
    __c___c___c___c___c___MAX BHLH DOMAIN_c___c___c___c___c___c___>

4330         4340         4350         4360         4370
    *      *      *      *      *      *      *      *      *
   AAT GCT CTT CTG GAG CAA CAA GTC CGT GCA CTG GAG AAG GCA AGA TCA
    N   A   L   L   E   Q   Q   V   R   A   L   E   K   A   R   S>
    __c___c___c___c___c___MAX BHLH DOMAIN_c___c___c___c___c___c___>

>HindIII
                                  |
      4380         4390         4400
    *      *      *      *      * |*      *
   AGT GCC CAA CTG CAG ACC TGAGGCAA GCTTATC
    S   A   Q   L   Q   T>
    __MAX BHLH DOMAIN_c___>
```

FIG. 26

```
       >NdeI                                                    >BamHI
        |                                                         |
     4090        4100         4110         4120       |   4130
   * | *    *    *    *    *    *    *    *    *         *
ATATACAT ATG GCT AGC ATG ACT GGT GGA CAG CAA ATG GGT CGG GAT CCT
          M   A   S   M   T   G   G   Q   Q   M   G   R>
   ___a___a___a___a___a_F10___a___a___a___a___a___>
                                                  D   P>
                                              ___b___>

>XhoI
                                                             |
        4140         4150         4160         4170          |
     *    *    *    *    *    *    *    *    *    * |
    GAC CTG GAA AAA GAG GCC GAA GAG CTG GAG CAG GAA AAC GCT GAA CTC
     D   L   E   K   E   A   E   E   L   E   Q   E   N   A   E   L>
   ___b___b__TWO AMPHIPATHIC HEPTAD S (1st  PHASE- 783) ___b___b___>

4180         4190         4200         4210         4220
  *    *    *    *    *    *    *    *    *    *
GAG CTG GAA GAC AGC TTT CAC AGT TTG CGG GAC TCA GTC CCA TCA CTC
 E   L   E>
___b___b___>
             D   S   F   H   S   L   R   D   S   V   P   S   L>
          ___c___c___c___c_MAX BHLH DOMAIN___c___c___c___c___>

4230         4240         4250         4260         4270
  *    *    *    *    *    *    *    *    *    *
CAA GGA GAG AAG GCA TCC CGG GCC CAA ATC CTA GAC AAA GCA ACA GAG
 Q   G   E   K   A   S   R   A   Q   I   L   D   K   A   T   E>
___c___c___c___c___c___MAX BHLH DOMAIN_c___c___c___c___c___c___>

4280         4290         4300         4310         4320
  *    *    *    *    *    *    *    *    *    *
TAT ATC CAG TAT ATG CGA AGG AAA AAC CAT ACG CAC CAG CAA GAC ATT
 Y   I   Q   Y   M   R   R   K   N   H   T   H   Q   Q   D   I>
___c___c___c___c___c___MAX BHLH DOMAIN_c___c___c___c___c___c___>

4330         4340         4350         4360         4370
  *    *    *    *    *    *    *    *    *    *
GAT GAC CTC AAG CGG CAG AAT GCT CTT CTG GAG CAA CAA GTC CGT GCA
 D   D   L   K   R   Q   N   A   L   L   E   Q   Q   V   R   A>
___c___c___c___c___c___MAX BHLH DOMAIN_c___c___c___c___c___c___>

>HindIII
                                                           |
    4380         4390         4400         4410         | 4420
  *    *    *    *    *    *    *    *    *    * |*    *
CTG GAG AAG GCA AGA TCA AGT GCC CAA CTG CAG ACC TGA GGCAAGCTTA
 L   E   K   A   R   S   S   A   Q   L   Q   T>
___c___c___c___MAX BHLH DOMAIN_c___c___c___c___>

```
>NdeI                                              >BamHI
 |                                                  |
     4090         4100         4110         4120    |   4130
  * |  *      *    *      *    *      *    *      * |  *
ATATACAT ATG GCT AGC ATG ACT GGT GGA CAG CAA ATG GGT CGG GAT CCT
         M   A   S   M   T   G   G   Q   Q   M   G   R>
         ___a___a___a___a___a_F10___a___a___a___a___a___>
                                                     D   P>
                                                     ___b___>

>XhoI
                                                     |
     4140         4150         4160         4170     |
  *      *    *      *    *      *    *      *    * |
GAC CTG GAA AAA GAG GCC GAA GAG CTG GAG CAG GAA AAC GCT GAA CTC
 D   L   E   K   E   A   E   E   L   E   Q   E   N   A   E   L>
 ___b___b__TWO AMPHIPATHIC HEPTAD S (2ND PHASE- 784)____b___b___>

4180         4190         4200         4210         4220
  *      *    *      *    *      *    *      *    *      *
GAG GAA CTG GAA GAC AGC TTT CAC AGT TTG CGG GAC TCA GTC CCA TCA
 E   E   L   E>
 ___TWO AMPH____>
             D   S   F   H   S   L   R   D   S   V   P   S>
             ___c____c____c___MAX BHLH DOMAIN_c____c____c____c___>

4230         4240         4250         4260         4270
  *      *    *      *    *      *    *      *    *      *
CTC CAA GGA GAG AAG GCA TCC CGG GCC CAA ATC CTA GAC AAA GCA ACA
 L   Q   G   E   K   A   S   R   A   Q   I   L   D   K   A   T>
 ___c____c____c____c____c___MAX BHLH DOMAIN_c____c____c____c____c___>

4280         4290         4300         4310         4320
  *      *    *      *    *      *    *      *    *      *
GAG TAT ATC CAG TAT ATG CGA AGG AAA AAC CAT ACG CAC CAG CAA GAC
 E   Y   I   Q   Y   M   R   R   K   N   H   T   H   Q   Q   D>
 ___c____c____c____c____c___MAX BHLH DOMAIN_c____c____c____c____c___>

4330         4340         4350         4360         4370
  *      *    *      *    *      *    *      *    *      *
ATT GAT GAC CTC AAG CGG CAG AAT GCT CTT CTG GAG CAA CAA GTC CGT
 I   D   D   L   K   R   Q   N   A   L   L   E   Q   Q   V   R>
 ___c____c____c____c____c___MAX BHLH DOMAIN_c____c____c____c____c___>

>HindIII
                                                     |
     4380         4390         4400         4410     |   4420
  *      *    *      *    *      *    *      *    * | *
GCA CTG GAG AAG GCA AGA TCA AGT GCC CAA CTG CAG ACC TGAGGCAAGC
 A   L   E   K   A   R   S   S   A   Q   L   Q   T>
 ___c____c____c____c_MAX BHLH DOMAIN____c____c____c____c___>

*
TTATC
```

FIG. 28

```
         >NdeI                                              >BamHI
          |                                                  |
       4090         4100         4110         4120           4130
     * | *     *     *     *     *     *     *     *     *     *
   ATATACAT ATG GCT AGC ATG ACT GGT GGA CAG CAA ATG GGT CGG GAT CCT
            M   A   S   M   T   G   G   Q   Q   M   G   R>
           __a___a___a___a___a_F10___a___a___a___a___a___>
                                                         D   P>
                                                        ___b___>

>XhoI
                                                            |
              4140         4150         4160         4170   |
            *     *     *     *     *     *     *     *   * |
          GAC CTG GAA AAA GAG GCC GAA GAG CTG GAG CAG GAA AAC GCT GAA CTC
           D   L   E   K   E   A   E   E   L   E   Q   E   N   A   E   L>
          ___b___b__TWO AMPHIPATHIC HEPTAD S (3D PHASE- 785)___b___b___>

4180         4190         4200         4210         4220
   *     *     *     *     *     *     *     *     *     *
  GAG GAA GAG CTG GAA GAC AGC TTT CAC AGT TTG CGG GAC TCA GTC CCA
   E   E   E   L   E>
  ___TWO AMPHIPAT____>
                       D   S   F   H   S   L   R   D   S   V   P>
                      ___c___c___c_MAX BHLH DOMAIN___c___c___c___>

4230         4240         4250         4260         4270
     *     *     *     *     *     *     *     *     *     *
   TCA CTC CAA GGA GAG AAG GCA TCC CGG GCC CAA ATC CTA GAC AAA GCA
    S   L   Q   G   E   K   A   S   R   A   Q   I   L   D   K   A>
   ___c___c___c___c___c___c__MAX BHLH DOMAIN_c___c___c___c___c___c___>

4280         4290         4300         4310         4320
     *     *     *     *     *     *     *     *     *     *
   ACA GAG TAT ATC CAG TAT ATG CGA AGG AAA AAC CAT ACG CAC CAG CAA
    T   E   Y   I   Q   Y   M   R   R   K   N   H   T   H   Q   Q>
   ___c___c___c___c___c___MAX BHLH DOMAIN_c___c___c___c___c___c___>

4330         4340         4350         4360         4370
     *     *     *     *     *     *     *     *     *     *
   GAC ATT GAT GAC CTC AAG CGG CAG AAT GCT CTT CTG GAG CAA CAA GTC
    D   I   D   D   L   K   R   Q   N   A   L   L   E   Q   Q   V>
   ___c___c___c___c___c___MAX BHLH DOMAIN_c___c___c___c___c___c___>

>HindIII
                                                          |
            4380         4390         4400         4410   4420
          *     *     *     *     *     *     *     *   *   *
        CGT GCA CTG GAG AAG GCA AGA TCA AGT GCC CAA CTG CAG ACC TGAGGCA
         R   A   L   E   K   A   R   S   S   A   Q   L   Q   T>
        ___c___c___c___c___MAX BHLH DOMAIN_c___c___c___c___c___>

*
  AGCTTATC
```

```
BamHI     10         20         30         40
     *  *      *      *      *      *      *      *      *
GGATCCC AAC GAC AAG AGG CGG ACA CAC AAC GTC TTG GAA CGT CAG AGG
        N   D   K   R   R   T   H   N   V   L   E   R   Q   R>
        ___PUTATIVE; NCBI GI: 50468; CODON_START=1; C-MYC ____>

50         60         70         80         90
    *      *      *      *      *      *      *      *      *
AGG AAC GAG CTG AAG CGC AGC TTT TTT GCC CTG CGT GAC CAG ATC CCT
 R   N   E   L   K   R   S   F   F   A   L   R   D   Q   I   P>
___PUTATIVE; NCBI GI: 50468; CODON_START=1; C-MYC PROTEIN;____>

100        110        120        130        140
    *      *      *      *      *      *      *      *      *      *
GAA TTG GAA AAC AAC GAA AAG GCC CCC AAG GTA GTG ATC CTC AAA AAA
 E   L   E   N   N   E   K   A   P   K   V   V   I   L   K   K>
___PUTATIVE; NCBI GI: 50468; CODON_START=1; C-MYC PROTEIN;____>

150        160        170        180        190
        *      *      *      *      *      *      *      *      *
GCC ACC GCC TAC ATC CTG TCC ATT CAA GCA GAC GAG CAC AAG CTC ACC
 A   T   A   Y   I   L   S   I   Q   A   D   E   H   K   L   T>
___PUTATIVE; NCBI GI: 50468; CODON_START=1; C-MYC PROTEIN;____>

200        210        220        230        240
    *      *      *      *      *      *      *      *      *      *
TCT GAA AAG GAC TTA TTG AGG AAA CGA CGA GAA CAG TTG AAA CAC AAA
 S   E   K   D   L   L   R   K   R   R   E   Q   L   K   H   K>
___PUTATIVE; NCBI GI: 50468; CODON_START=1; C-MYC PROTEIN;____>

250        260        270
    *      *      *      *      *      *      *
CTC GAA CAG CTT CGA AAC TCT GGT GCA TAA AAGCTT
 L   E   Q   L   R   N   S   G   A   *>   |____|
                                          HindIII
___PUTATIVE; NCBI GI: 50468; CODON____>
```

FIG. 29

EXTENSION OF A PROTEIN-PROTEIN INTERACTION SURFACE TO INACTIVATE THE FUNCTION OF A CELLULAR PROTEIN

This application claims priority to U.S. Provisional Patent Application No. 60/001,654, filed Jul. 31, 1995 and to U.S. Provisional Patent Application No. 60/018,496, filed May 29, 1996.

FIELD OF THE INVENTION

The present invention relates to the production of sequence-specific DNA binding proteins which function as eukaryotic transcription factors, i.e., transcription regulatory proteins. The invention more particularly relates to the generation of multimeric proteins having nucleic acid (i.e., DNA or RNA) binding domains in which the binding domain or protein interaction surface is engineered or modified to be acidic in nature. Such a nucleic acid binding protein having an acidic multimerization domain is capable of regulating the function of a target nucleic acid sequence or gene to which it is bound, thereby acting as potent dominant-negative regulators of gene transcription, and cell growth and proliferation.

BACKGROUND OF THE INVENTION

Dominant-negative proteins are capable of inhibiting the binding of nucleic acid binding proteins, i.e., DNA binding proteins, such as transcription regulatory proteins, to target DNA sequences to inactivate gene function. (I. Herskowitz, 1987, *Nature*, 329:219–222).

The basic-region leucine zipper ("bZIP") DNA binding proteins are a family/class of nucleic acid binding proteins, which are eukaryotic transcription regulatory proteins that regulate transcription of genes by binding as dimers to specific DNA sequences. bZIP proteins characteristically possess two domains—a leucine zipper structural domain and a basic domain that is rich in basic amino acids (C. Vinson et al., 1989, *Science*, 246:911–916). The two domains are separated by a short segment known as the fork. Two bZIP proteins dimerize by forming a coiled coil region in which the leucine zipper domains dimerize. The basic regions then interact with the major groove of the DNA molecule at a specific DNA sequence site. The binding to DNA stabilizes the dimer. The dimerization and DNA-interaction event regulates eukaryotic gene transcription.

The leucine zipper motif is common to the primary structure of a number of DNA binding proteins, including the yeast transcription factor GCN4, the mammalian transcription factor CCAAT/enhancer-binding protein C/EBP, and the nuclear transforming oncogene products, Fos and Jun, and is characterized by a repeat of leucine amino acids every seven residues (i.e., a heptad repeat); the residues in this region can form amphipathic α-helices. The leucine-rich amphipathic helices interact and form a dimer complex, called a leucine zipper, at the carboxyl terminus (W. H. Landschultz et al., 1988, *Science*, 240:1759–1764; A. D. Baxevanis and C. R. Vinson, 1993, *Curr. Op. Gen. Devel.*, 3:278–285), such that the dimerization region forms a coiled coil (E. K. O'Shea et al., 1989, *Science*, 243:538–542).

Another class of DNA binding proteins, which have similarities to the bZIP motif, are the basic-region helix-loop-helix ("bHLH") proteins (C. Murre et al., 1989, *Cell*, 56:777–783). bHLH proteins are also composed of discrete domains, the structure of which allows them to recognize and interact with specific sequences of DNA. The helix-loop-helix region promotes dimerization through its amphipathic helices in a fashion analogous to that of the leucine zipper region of the bZIP proteins (R. I. Davis et al., 1990, *Cell*, 60:733–746; A. Voronova and D. Baltimore, 1990, *Proc. Natl. Acad. Sci. USA*, 87:4722–4726). Nonlimiting examples of hHLH proteins are myc, max, and mad; myc and mad are known to heterodimerize.

The existence of the leucine zipper in the dimerization region of bZIP proteins allows for a high degree of biological control through the formation of both homodimers and heterodimers. For example, heterodimers are known to form between Fos and Jun (D. Bohmann et al., 1987, *Science*, 238:1386–1392), among members of the ATF/CREB family (T. Hai et al., 1989, *Genes Dev.*, 3:2083–2090), among members of the C/EBP family (Z. Cao et al., 1991, *Genes Dev.*, 5:1538–1552; S. C. Williams et al., 1991, *Genes Dev.*, 5:1553–1567; and C. Roman et al., 1990, *Genes Dev.*, 4:1404–1415), and between members of the ATF/CREB and Fos/Jun families (T. Hai and T. Curran, 1991, *Proc. Natl. Acad. Sci. USA*, 88:3720–3724). In general, dimerization of bZIP proteins depends upon the ability of both of the individual carboxyl terminal α-helices to line up in correct register with one another and to generate a symmetric coiled coil. This, in turn, places the amino terminal basic regions in a symmetric orientation, thus allowing them to interact with DNA (A. D. Baxevanis and C. R. Vinson, 1993, *Curr. Op. Gen. Devel.*, 3:278–285). It has been shown that the ability of the helices within the coiled coil to find the proper register with respect to one another is controlled inherently by the individual helices themselves, and not by the placement of the basic region with respect to the DNA (W. Pu and K. Struhl, 1993, *Nucleic Acids Research*, 21:4348–4355). However, it will be appreciated that the generation of a symmetric coiled coil structure is not a mandatory requirement for the interaction of the multimerization or dimerization domains of various types of nucleic acid binding proteins.

The bZIP proteins are highly conserved throughout the eukaryotic kingdom and have been isolated and identified in yeast, plants, and mammals. These proteins mediate a variety of biological processes, including oncogenesis, memory, segmentation, and energy regulation (R. Boussoudan, 1994, *Cell*, 79:59–68; S. Cordes, and G. Barsh, 1994, *Cell*, 79:1025–1034; S. McKnight et al., 1989, *Genes Dev.*, 3:2021–2024; and I. Verma, 1986, *Trends in Genetics*, 2:93–96.). Therefore, the ability to inhibit the activity of those proteins associated with oncogenesis or abnormal cell growth and proliferation, for example, is a desirable goal in the field.

In addition, inhibition of the production or function of other cellular proteins that are detrimental, or that influence unwanted or inappropriate phenotypes, in cells, tissues, and, ultimately, the whole organism, is an aim for practitioners in the art.

Of the nearly 70 bZIP proteins that have been identified to date, (H. Hurst, 1994, *Protein Profiles*, 1:123–168), most can be categorized into one of five major subfamilies on the basis of their DNA recognition properties and amino acid sequence similarities (P. F. Johnson, 1993, *Mol. Cell. Biol.*, 13:6919–6930). These bZIP subgroups include the AP-1, CREB/ATF, C/EBP, PAR, and plant G-box proteins. The proteins in each subfamily recognize highly similar or identical DNA sites whose consensus sequences are 9- or 10-base pair palindromes composed of two 5-base pair half-sites. Binding sites for the various classes of bZIP proteins may differ either by their half-site sequences or their half-site spacing properties. AP-1 proteins, such as Fos, Jun, and GCN4 bind to a 9-base pair pseudopalindromic sequence that can be viewed as two half-sites that overlap by a single base pair, while the consensus binding sites for the other four families have directly abutted pairs of half-sites (N. B. Haas et al., 1995, *Mol. Cell. Biol.*, 15:1923–1932). In addition, thyrotroph embryonic factor (TEF), a transcription factor expressed in the developing anterior pituitary gland, and the liver-enriched albumin D box-binding protein (DBP), (C. R. Mueller et al., 1990, *Cell*, 61:279–291), have been reported to constitute another class of bZIP proteins (D. W. Drolet et al., 1991, *Genes Dev.*, 5:1739–1753).

bZIP proteins lacking the transactivation domain are naturally occurring dominant negatives that are generally produced by a genetic deletion of the transactivation domain (A. Clark and K. Dougherty, 1993, *Biochem J.*, 296:521–541; P. Descombes and U. Schibler, 1991, *Cell*, 67:569–579; N. Foulkes et al., 1991, *Cell*, 64:739–749; and J. Yin et al., 1994, *Cell*, 79:49–58). These truncated bZIP proteins are able to dimerize and bind to DNA, and if overexpressed, can act as dominant negatives, presumably by competing with the endogenous bZIP protein for its promoter DNA binding site. Accordingly, the truncated bZIP proteins act by mass action to occlude the normal transactivator from the DNA. In addition, it is possible that the deletion of the transactivation domain could also produce a protein having increased, rather than decreased, DNA binding properties. If this were the case, then this type of truncated and naturally occurring dominant negative would not have to be overexpressed to generate particular phenotypes (A. Braiser and A. Kumar, 1994, *J. Biol. Chem.*, 269:10341–10351).

Needed in the art are proteins, expressed and operative in cells, having dominant-negative function to control the transcription of genes or which regulate RNA production and function in a cell. Such expressed proteins can be used for regulating abnormal cell growth in a variety of eukaryotic organisms, including plants, animals, mammals, including humans, insects, microorganisms, and viruses. The present invention provides to the art proteins which can be modified in a particular way to control gene regulation. The particular type of modification may control gene function, for example, to inhibit abnormal or cancer cell growth and proliferation, to inhibit pathogenic diseases caused by microorganisms, particularly eukaryotic microorganisms, such as yeast, and the like, or viruses and may be used as therapeutics for treating pathological diseases and cancer.

SUMMARY OF THE INVENTION

The present invention provides multimeric nucleic acid (i.e., DNA or RNA) binding proteins, such as transcription regulating proteins, which have been engineered to contain in their multimerization or protein interaction domains at least one amino terminal acidic amino acid residue. The acidic nature of such nucleic acid binding proteins affects the binding of the proteins to other proteins, e.g., forming heterodimers or heteromultimers, and, ultimately the binding of the proteins to a target DNA or RNA sequence or gene. Nucleic acid binding proteins containing an extension of acidic amino acid residues have an extended protein interaction surface or multimerization or dimerization interface. DNA binding proteins are a particular example of nucleic acid binding proteins suitable for the invention. RNA binding proteins are also suitable for use in the invention. In accordance with the invention, the acidic nature of the protein increases the stability of heteromultimeric or heterodimeric complexes that are formed.

It is an object of the present invention to provide an acidic extension to a protein-protein interaction surface or dimerization interface to inactivate the function of a cellular protein. In accordance with the invention, proteins which are useful as drugs, inhibitory molecules, or growth-controlling agents or compounds are provided which, when used both in vitro and in vivo, can inhibit the expression and activity of cellular proteins, the effects of which can be harmful, deleterious, and even lethal, to cell growth and survival.

It is another object of the invention to add acidic amino acid residues to create a multimerization or dimerization surface or extension onto a multimeric complex, particularly a protein, polypeptide or peptide having basic regions that bind to nucleic acids, such as DNA or RNA. More particularly, the acidic extension appended onto the multimeric protein can replace the basic region of such proteins to create molecules that regulate and control cell growth.

It is another object of the invention to regulate gene transcription and expression by providing suitable dominant negative mutant molecules having an acidic phenotype that specifically heterodimerize with native proteins to disrupt the normal action of the native proteins in vivo, thereby causing the subsequent inactivation of cellular gene products.

It is another object of the invention to create dominant negative transcription regulatory proteins by extending the protein-protein interaction surface, making it acidic in nature, to inactivate the function of a cellular protein by specifically and stoichiometrically displacing the native protein from its normal binding with DNA and by inhibiting transactivation and, ultimately, gene transcription and protein production.

It is another object of the invention to provide improved, genetically engineered dominant negative transcription factor proteins that stoichiometrically inhibit the DNA binding of DNA binding proteins, such as bZIP and bHLH proteins, and structurally related types of proteins, to limit the pleiotropic effects normally associated with naturally occurring dominant negative overexpression. The dominant negative mutant proteins of the invention are created by the addition of acidic residues the N-terminus of a multimeric protein, most preferably a DNA binding protein.

It is another object of the invention to provide methods and rationally-designed constructs suitable for producing and expressing the dominant negative proteins described herein for the specific inactivation of cellular gene products and for use in gene therapy techniques.

It is another object of the invention to utilize the acidic extension of the engineered DNA binding proteins to stabilize a variety of different basic regions of proteins and to create robust dominant negative protein members of various families of DNA binding proteins.

It is yet another object of the invention to provide transgenic animals harboring at least one genetically engineered plasmid construct or vector containing a DNA sequence encoding a DNA binding protein that is acidic in nature to control gene expression in a tissue specific manner.

It is a further object of the invention to provide transgenic animals harboring at least one genetically engineered plasmid construct or vector containing a DNA sequence encoding a DNA binding protein that is acidic in nature which behaves as a dominant negative to the wild type protein and provides viable phenotypes to evaluate and assess the in vivo effects of the protein. Such animals may also be used for rational drug design (i.e., with the dominant negatives considered as drugs) and for testing and evaluating additional or supplemental treatments, drugs, therapies, and the like, and for ameliorating or alleviating the produced transgenic phenotypes.

It is another object to provide dimeric and multimeric nucleic acid binding proteins of plant and animal origin and having acidic multimerization domains allowing the nucleic acid binding protein to bind to a target DNA or RNA sequence, i.e., a specific gene, thereby regulating the function of the gene to which it is bound. Such proteins are expressed, as described herein, from expression eukaryotic or prokaryotic vector constructs molecularly engineered to contain isolated DNA sequences encoding a nucleic acid binding protein having an acidically extended dimerization or multimerization domain.

It is a further object of the invention to control the regulation of a gene through the type of acidic modification that is made to a nucleic acid binding protein, thereby providing therapeutic applications where the target gene or DNA or RNA sequence is present in abnormal or diseased cells and tissues and their normal counterparts. The engineered, acidic nucleic acid binding proteins provide tools for use in cancer therapeutics, diseases caused by eukaryotic microorganisms, for example, yeast, protozoans, algae, parasites, or by viruses, as well as tools for drug development, rational drug design, and drug and gene therapies.

Further objects and advantages afforded by the invention will be apparent from the detailed description hereinbelow.

DESCRIPTION OF THE DRAWINGS

As shown in FIG. 4, the mixture of unmodified c-Fos and c-Jun melted as 50° C. (closed circles). An engineered c-Fos protein having the basic region deleted (0heptad-Fos) increased the melting temperature of the Fos-Jun complex to 53° C. (open squares). An engineered c-Fos protein having the basic region replaced with an acidic region containing four heptad repeats (4heptad-Fos) increased the melting temperature of the Fos/Jun complex to 61° C. (open circles). The plasmid carrying DNA encoding 4heptad-Fos has been deposited with the American Type Culture Collection, 10801 University Blvd., Manassas, Va. 20110, under ATCC Designation No. 97583. An engineered c-Fos protein in which one amino acid in the acidic region was changed from an asparagine to a leucine, as described for FIG. 2, called new4heptadFos (or N4heptad-Fos), resulted in a higher melting temperature of 72° C., and more stable heterodimerization with c-Jun (closed squares). The plasmid carrying DNA encoding N4heptad-Fos has been deposited with the American Type Culture Collection, 10801 University Blvd., Manassas, Va. 20110 under ATCC Designation No. 97584. Also as shown in FIG. 4, homodimerization of unmodified c-Jun had a melting temperature of 29.4° C., and homodimerization of acidically modified c-Fos (having four acidic repeats appended at the amino terminus of the c-Fos protein) had a melting temperature of 25° C.

FIG. 5A shows that the specificity of the basic zipper region (bZIP) of the protein CEBP and the acidic extension on the N-terminus of a leucine zipper of the protein 4heptadFos is determined by the leucine zipper for DNA binding proteins having basic and acidic zipper regions (ZIP classes of proteins). A ZIP DNA binding protein having an acidic extension appended N-terminally is an acidically modified protein and is termed aZIP herein. As shown in FIG. 5A, mixing a bZIP CEBP protein and an aZIP 4heptadFos protein with incompatible zippers produces no interaction, i.e., 4heptadFos does not interact with CEBP.

FIG. 5B shows that mixing a bZIP VBP protein and an aZIP 3heptadF (CEBP specific) protein also produces no heterodimeric interaction. In FIGS. 5A and 5B, the solid lines represent the simple sum of the two homodimer curves. The fact that the actual mixture gives identical results to the sum curve demonstrates that no heterodimers are formed.

DPDLEKEAEELEQENAELELEDSF, called 2heptadMax(783); (SEQ ID NO:1). The plasmid carrying DNA encoding this acidically extended Max protein has been deposited with the American Type Culture Collection, under ATCC Designation No. 97585.

DPDLEKEAEELEQENAELEELEDSF, called 2heptadMax(784); (SEQ ID NO:2). The plasmid carrying DNA encoding this acidically extended Max protein has been deposited with the American Type Culture Collection, under ATCC Designation No. 97582.

DPDLEKEAEELEQENAELEELEDSF, called 2heptadMax(785); (SEQ ID NO:3). The plasmid carrying DNA encoding this acidically extended Max protein has been deposited with the American Type Culture Collection, under ATCC Designation No. 97586. AcidMax is an expressed Max protein having appended N-terminally an acidic extension as follows: DPDEEEDDEEELEELEDSF; (SEQ ID NO:4). The plasmid carrying DNA encoding this acidically extended Max protein has been deposited with the American Type Culture Collection, under ATCC Designation No. 97581.

0heptadMax is an expressed Max protein having an acidic extension as follows:

DPDLEELEDSF (SEQ ID NO:5).

Figure 9:
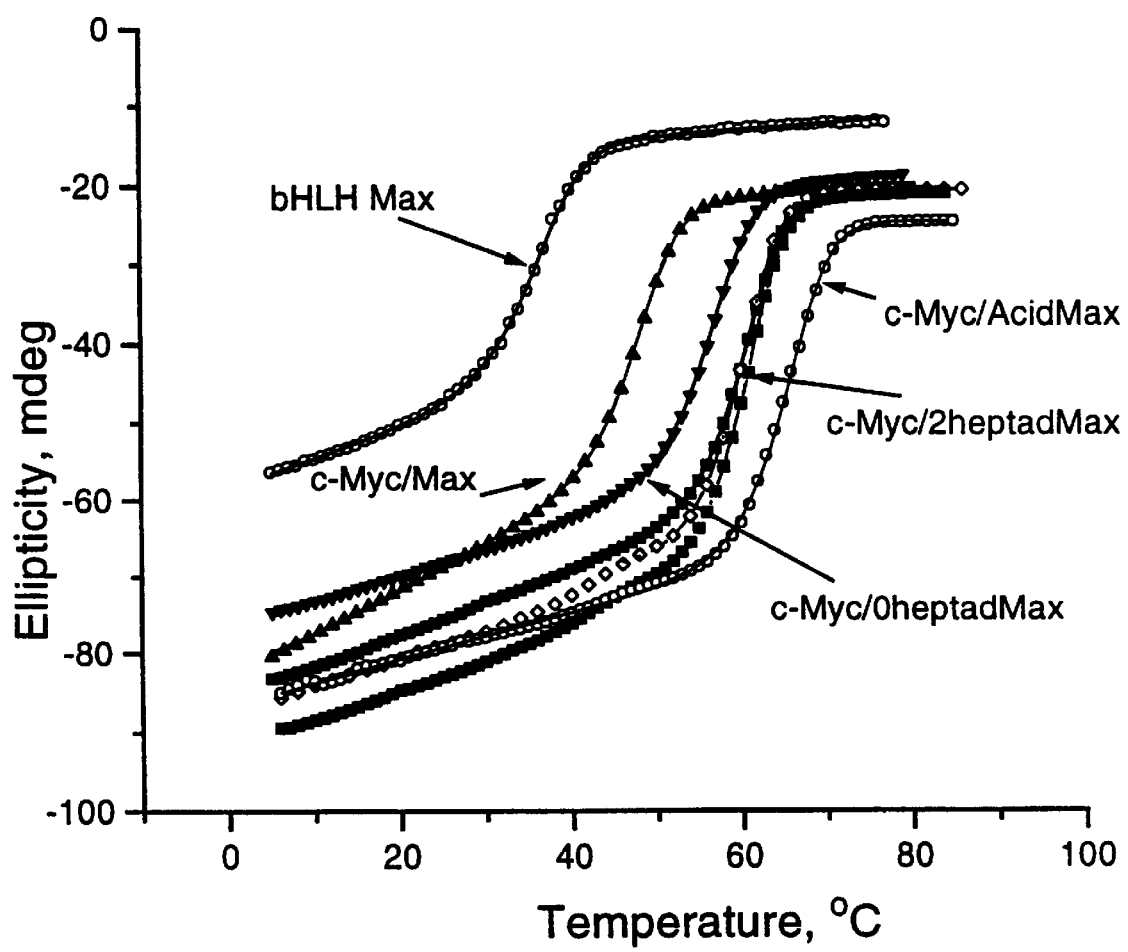
FIG. 9 shows the results of appending an acidic extension onto the dimerization domain of Max, a DNA binding protein of the bHLH class. The 2heptadMax proteins used in the heterodimerization studies shown in FIG. 9 are expressed Max proteins having acidic extensions as follows.

As can be seen from FIG. 9, an expressed Max protein having an appended polyglutamic acid sequence (i.e., AcidMax) heterodimerized better with c-Myc than did the expressed 2heptadMax proteins having the above-described acidic extensions.

Figure 10A:
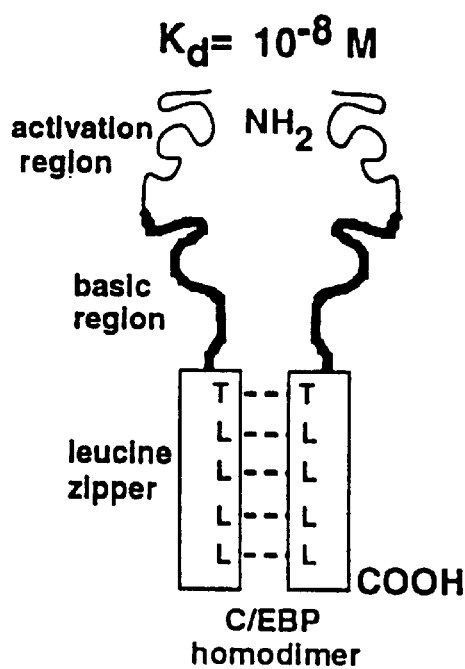
Figure 10B:
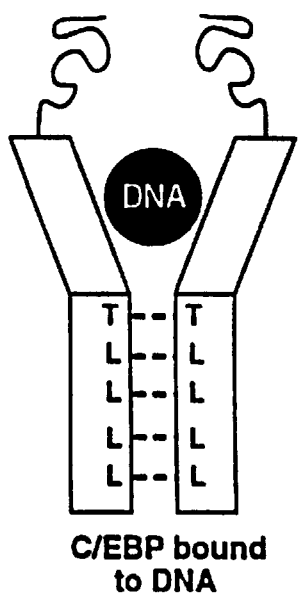
Figure 10C:
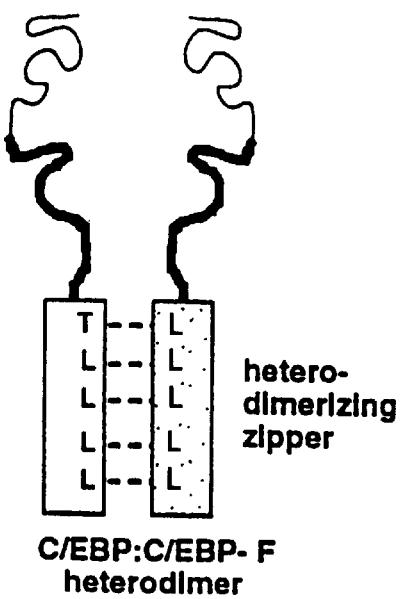
Figure 10D:
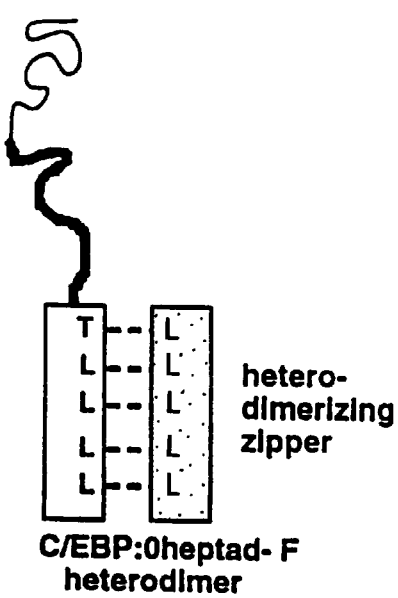

FIGS. 10A–10D are schematic depictions of the bZIP protein C/EBP dimerization both with and without DNA. The relative positions of the activation region, basic region, and leucine zipper within the protein are shown. The $NH_2$ (amino) terminus of the protein is the activation domain. The dashed line between the amino acids in the d positions of the leucine zipper represent a physical interaction. FIG. 10A: C/EBP dimerization. The basic region, presented as a bold line, is not helical. FIG. 10B: C/EBP binding to DNA. The presence of DNA induces the basic region to form an α- which increases the stability of the complex approximately 10-fold. FIG. 10C: Heterodimerization between wild type C/EBP and a C/EBP mutant having an F zipper which preferentially heterodimerizes with the C/EBP leucine zipper. FIG. 10D: Heterodimerization between C/EBP and 0heptad-F (i.e., the F zipper as shown in FIG. 10C, but having the basic region removed).

Figure 11B:
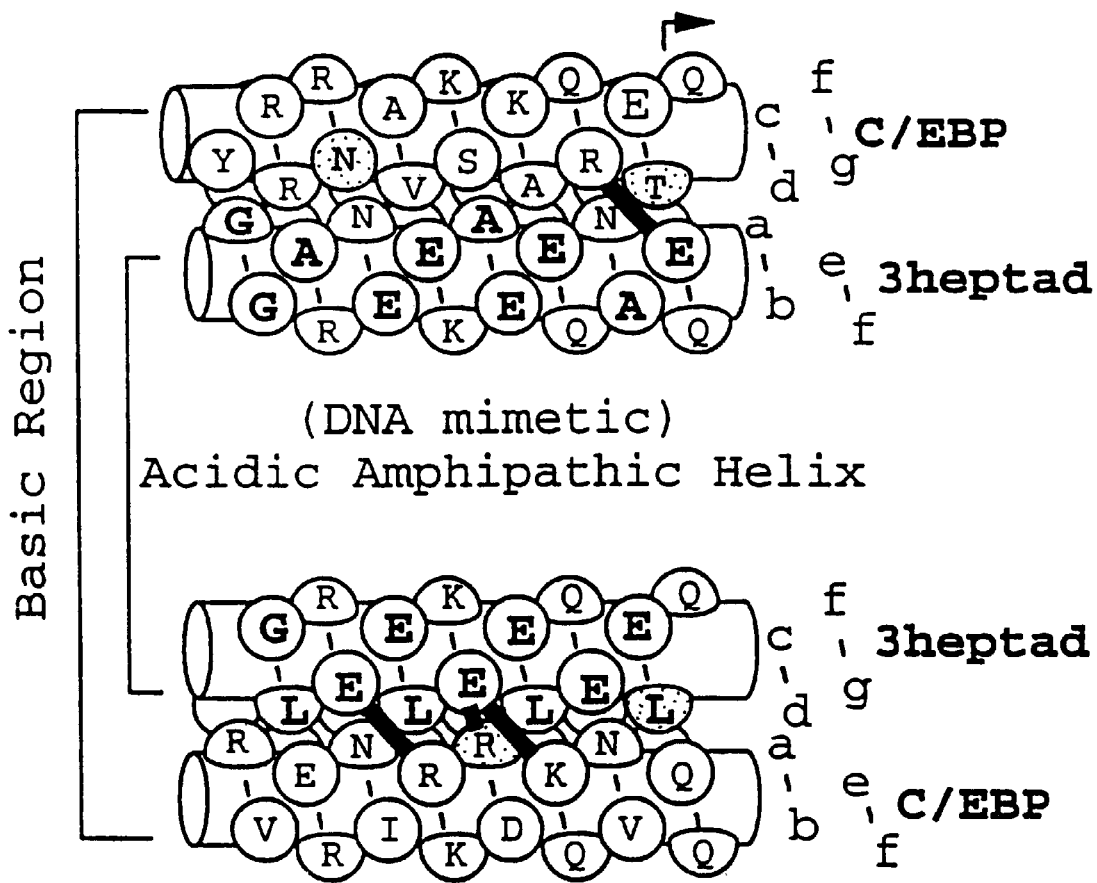
Figure 11C:
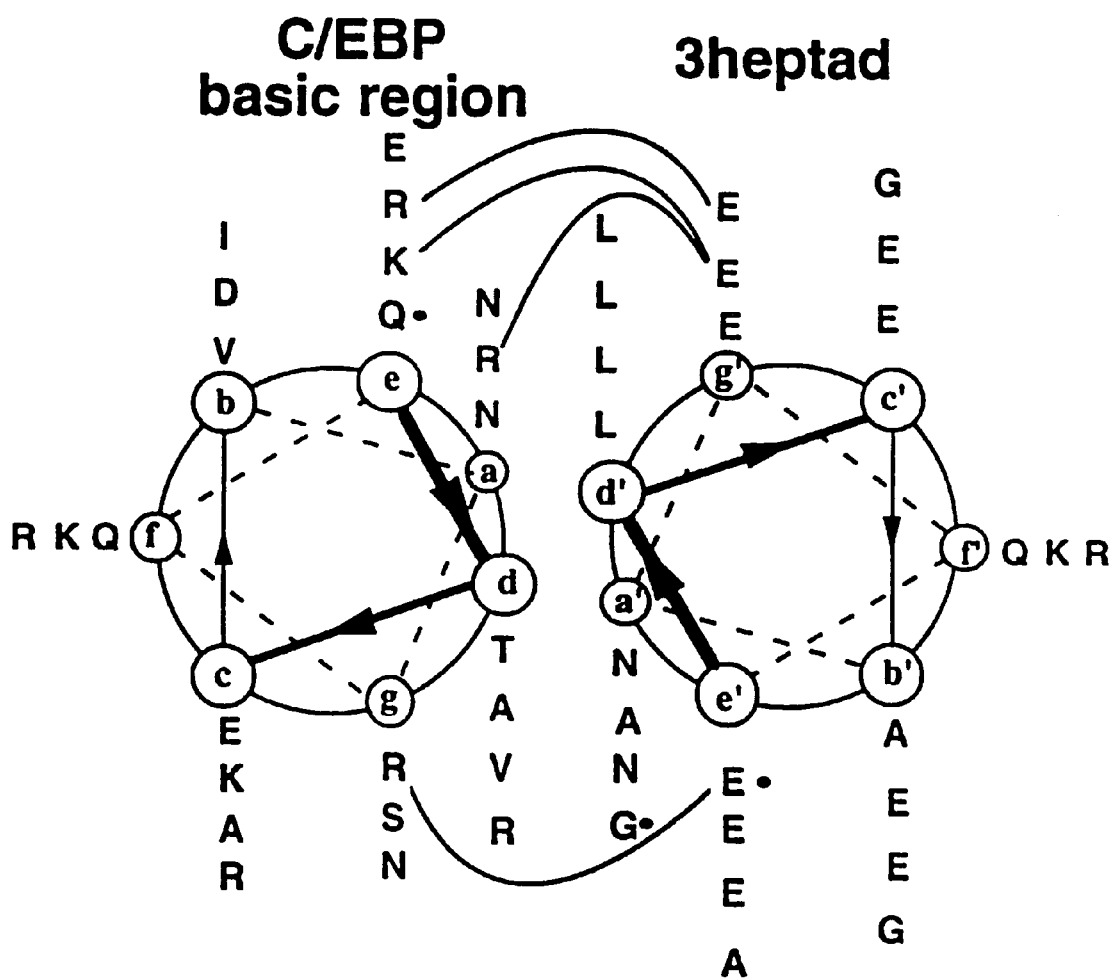

FIGS. 11A–11C demonstrate that acidic helical extension of the leucine zipper stabilizes dimerization with wild type bZIP protein. FIG. 11A shows the amino acid sequences of the 4heptad acidic helical extension, SEQ ID NO:57, and the three different basic regions of bZIP proteins that were examined, i.e., C/EBP, SEQ ID NO:58; VBP, SEQ ID NO:59; and GBF1, SEQ ID NO:60. The first leucine position of the zipper, the invariant asparagine and arginine of the basic region, and the tryptophan in the VBP bZIP protein are presented in bold-faced type. The coiled coil nomenclature of the basic region extending from the leucine zipper is indicated below with the hydrophobic a and d positions in bold type. FIG. 11B depicts a proposed heterodimeric coiled coil structure between the 3heptad acidic helical extension and the C/EBP basic region; both nonequivalent sides are shown. The f position amino acids are shown in both views. The amino acids in the 3heptad extension that have been changed from the parental C/EBP basic region are shown in bold type. The first leucine position of the zipper and the invariant asparagine and arginine of the basic region are stippled. The designed g⇌e' and g⇌a' electrostatic interactions are indicated by a black bar between the amino acids. The right-most d amino acid shown, indicated by an arrow, is the first d position of the leucine zipper (T for C/EBP and L for 3heptad) The coiled coil heptad letter designations (a,b,c,d,e,f,g) are shown to the right. The supercoiling of the two helices is not depicted. FIG. 11C is a coiled coil helical wheel diagram of the interaction shown in FIG. 11B, with a view from the C-terminus toward the N-terminus. The coiled coil sequence reads outward from the C- to N-termini around the wheel, starting at the e position following the first d position of the leucine zipper. Presumed electrostatic interactions between g⇌e' and g⇌a' are indicated.

Figure 12:
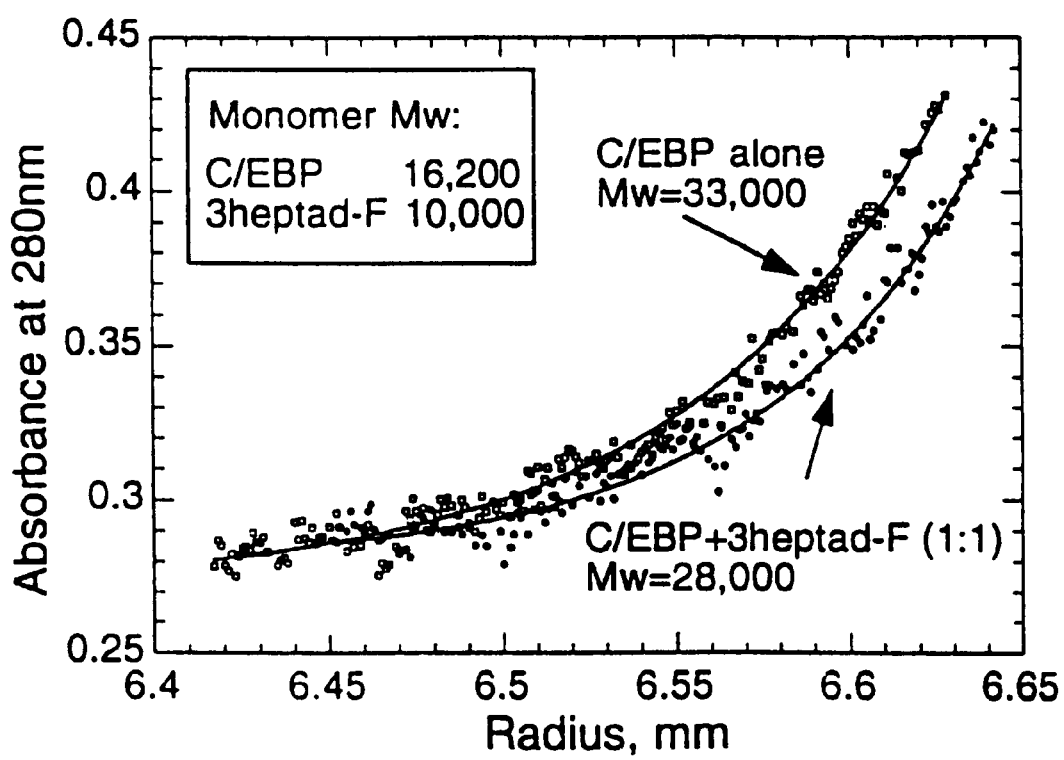

FIG. 12 shows the oligomerization of C/EBP determined in the presence or absence of 3heptad-F using sedimentation equilibrium analysis at 37° C. C/EBP alone (open squares) behaves as a single species with an apparent MW=33,000 Daltons, suggesting a homodimer structure. An equimolar mixture of C/EBP and 3heptad-F (closed circles) has an apparent MW=28,000 Daltons, indicating heterodimer formation.

Figure 13A:
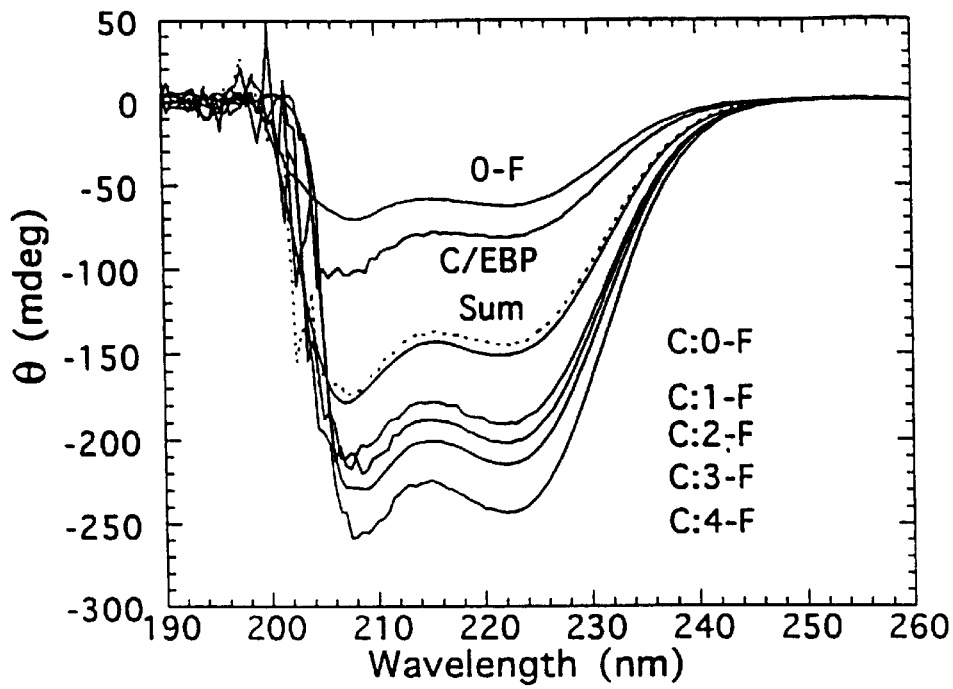
Figure 13B:
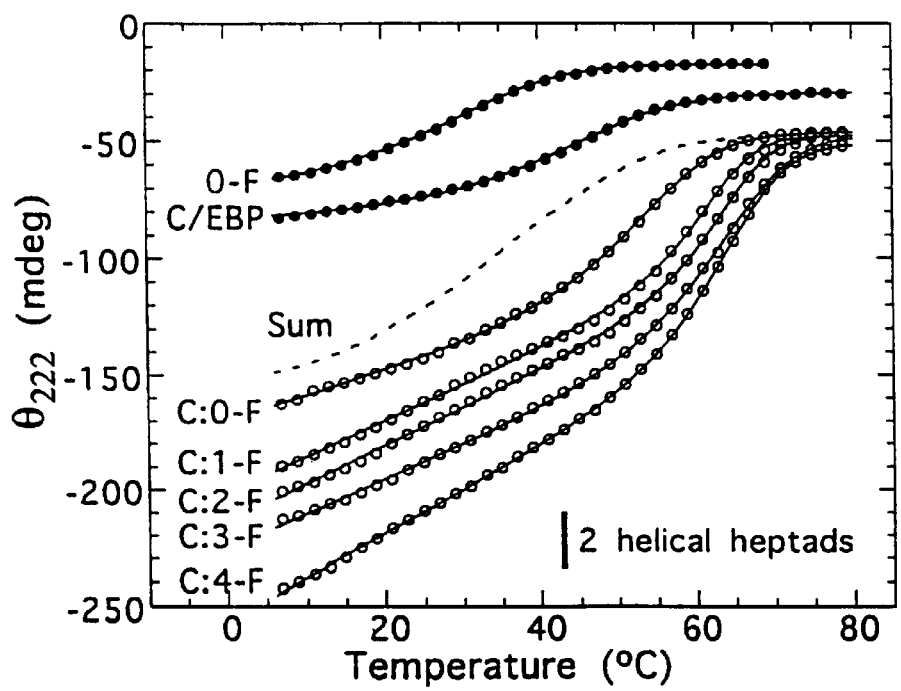

FIGS. 13A and 13B: FIG. 13A shows the circular dichroism (CD) spectra of the C/EBP bZIP domain (4 $\mu$M), 0heptad-F (4 $\mu$M), and the equimolar mixture of C/EBP and the F zipper containing different length acidic extensions (0,1,2,3,4,) (4 $\mu$M+4 $\mu$M). The minima at 208 and 222 nm indicate $\alpha$-helices. The sum of the spectra of C/EBP and 0heptad-F, which would be observed if the two samples did not interact, is shown as a dotted line. The increase in the 222 nm signal for the different mixtures suggests an increase in $\alpha$-helical content. The noise below 210 nm is due to the absorbance of dithiothreitol (DTT). FIG. 13B shows CD thermal melting curves at 222 nm of the samples shown in FIG. 13A. The fitted curve through each of the data sets was used to calculate $T_m$. The mixtures were more stable than C/EBP alone suggesting a stabilizing interaction between the two proteins. The bar shows the amount of ellipticity at 222 nm generated by extending the leucine zipper one heptad on both proteins of the heterodimer.

Figure 14A:
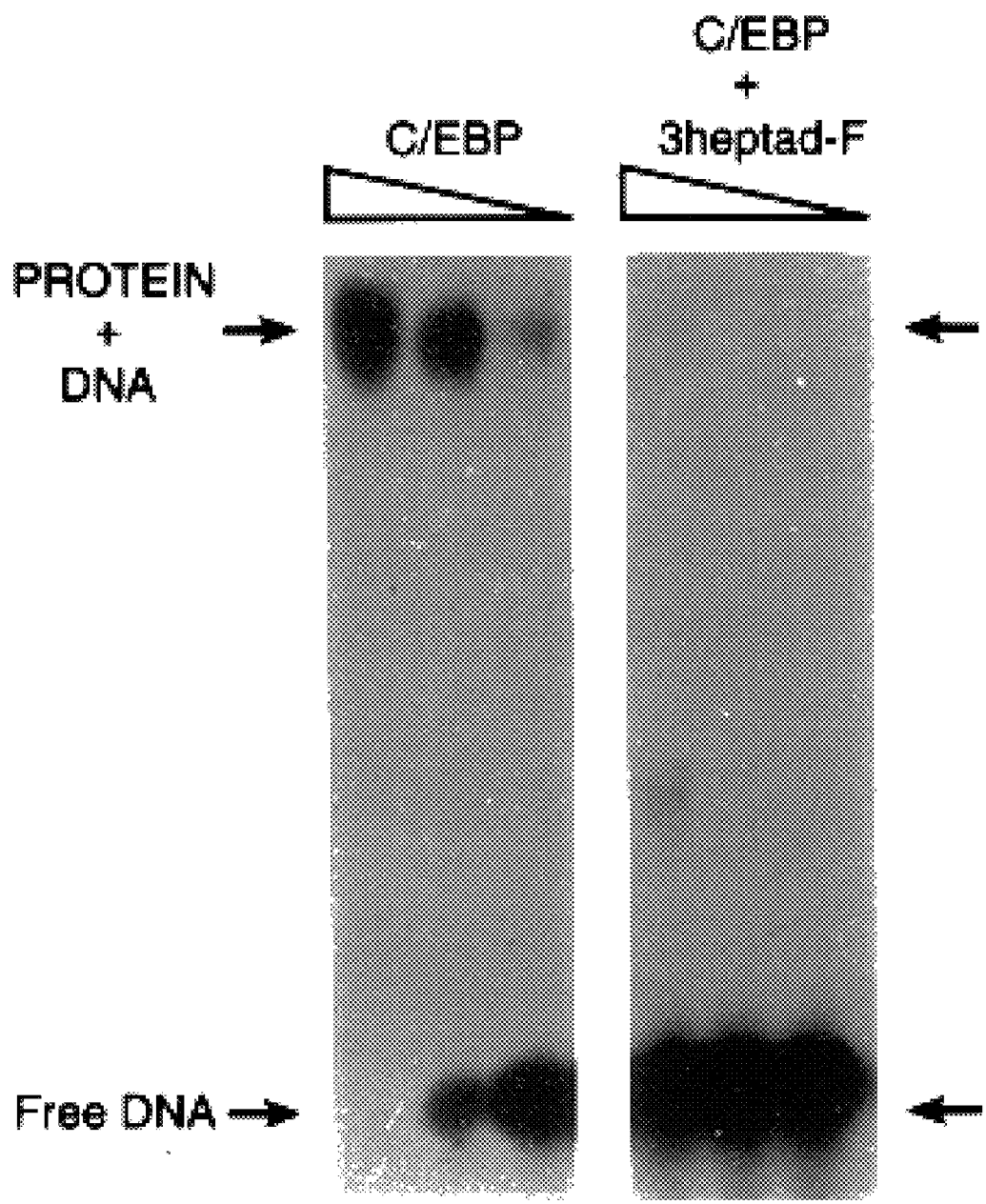
Figure 14B:
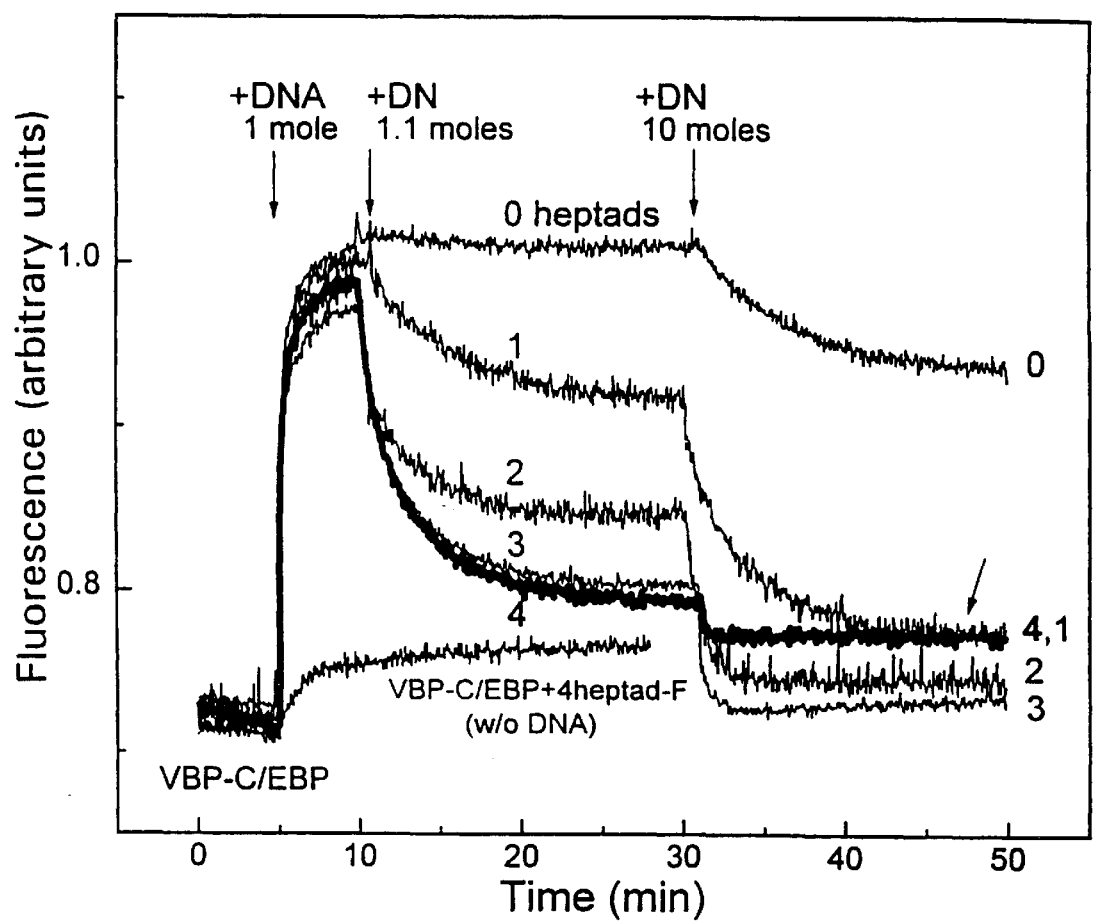

FIGS. 14A and 14B show that acidic extension inhibits the binding of C/EBP to DNA. FIG. 14A: 3heptad-F inhibits C/EBP DNA binding. The left panel shows a gel retardation assay of C/EBP binding to a specific DNA probe 28 bp in length. Protein was diluted four-fold in the successive lanes. The right panel shows the same assay as the left, except that 3heptad-F was added at the same concentration as C/EBP, resulting in a total absence of C/EBP DNA binding. FIG. 14B: Displacement of VBP-C/EBP from DNA by five dominant negatives (DNs) assayed by fluorescence. Fluorescence of a single tryptophan located in the basic region of VBP-C/EBP increased upon DNA binding (minutes 5–10). The addition of 1.1 molar equivalents of the F zipper or of the four different acidic extension caused a decrease in fluorescence. After 20 minutes, 10 more molar equivalents were added, causing an additional displacement of VBP-C/EBP from the DNA. 4heptad-F, shown in bold, causes the most dramatic displacement of VBP:C/EBP. The bottom line shows that mixing of VBP-C/EBP with 4heptad-F results in a new base line. This is not observed for the other four mixtures which return to the VBP-C/EBP-only baseline.

Figure 15:
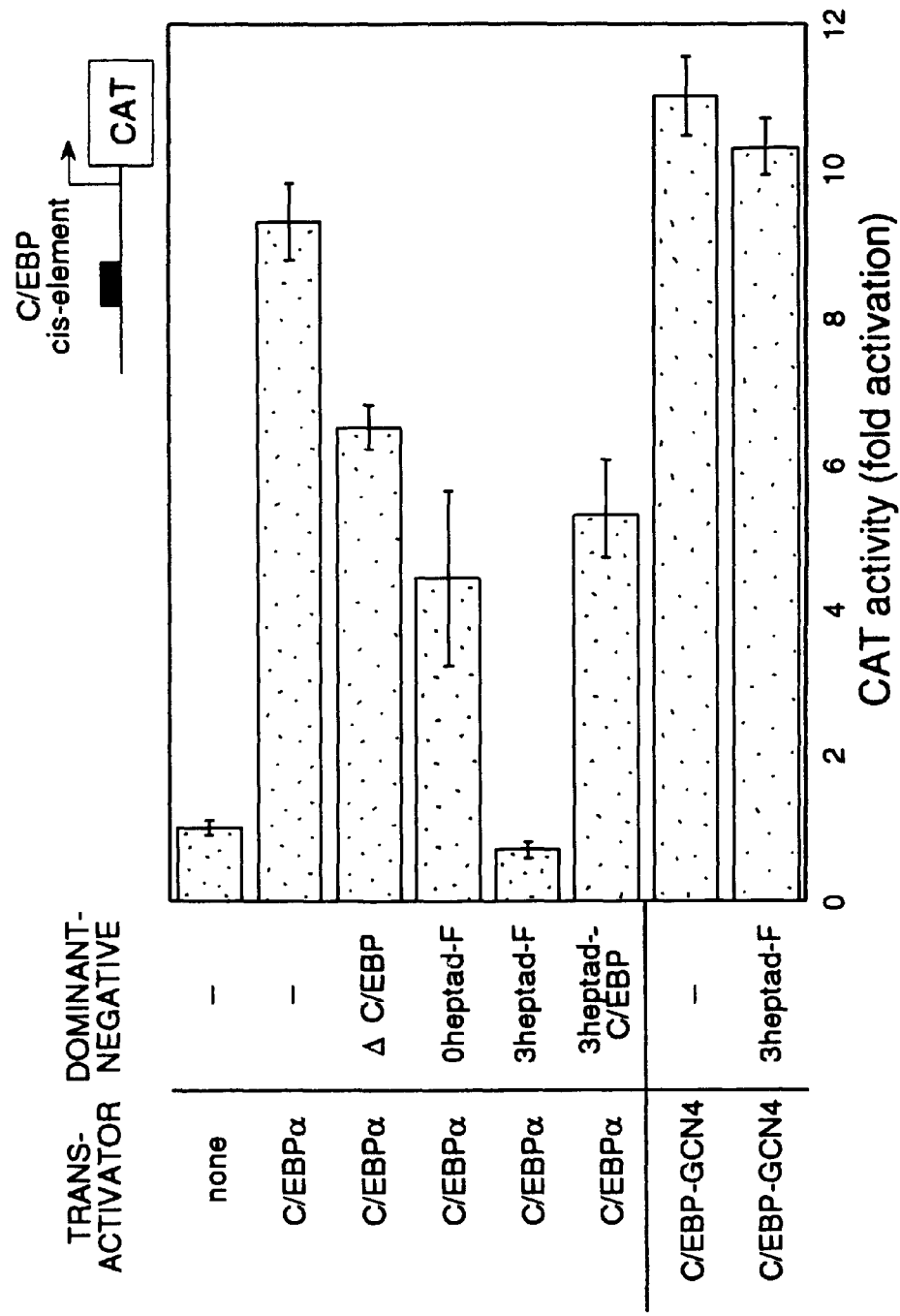

FIG. 15 demonstrates that acidic extension inhibits C/EBP transactivation. Human hepatoma cells (HepG2) were transiently transfected with three plasmids, a chloramphenicol acetyl transferase (CAT) expression plasmid driven by a single C/EBP cis element, the C/EBP transactivator, and different DNs. The histogram presents the extent of transactivation observed in the presence of different combinations of transactivator and dominant-negatives. In the absence of any DN, expressed C/EBP transactivated a single C/EBP site approximately 10 fold. This transactivation was partially inhibited by a C/EBP lacking the transactivation domain ($\Delta$C/EBP), the heterodimerizing zipper (0heptad-F), and the acidic extension appended to the regular C/EBP zipper (3heptad-C/EBP). Transactivation was completely inhibited by expressed 3heptad-F. The final two bars of the histogram show transactivation of an expressed C/EBP protein containing an alternate leucine zipper, the GCN4 zipper. This protein was able to transactivate a C/EBP containing promoter and was not inhibited by 3heptad-F.

Figure 16A:
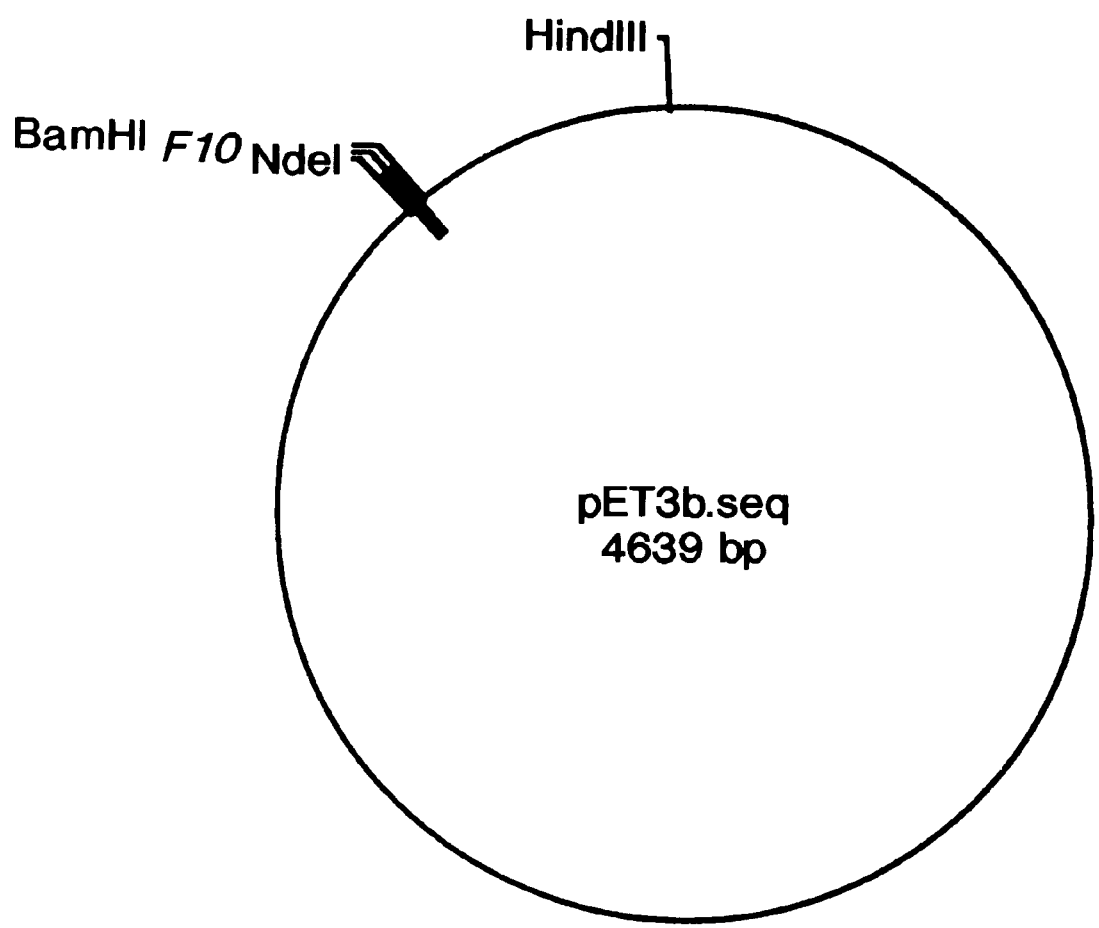
Figure 16B:
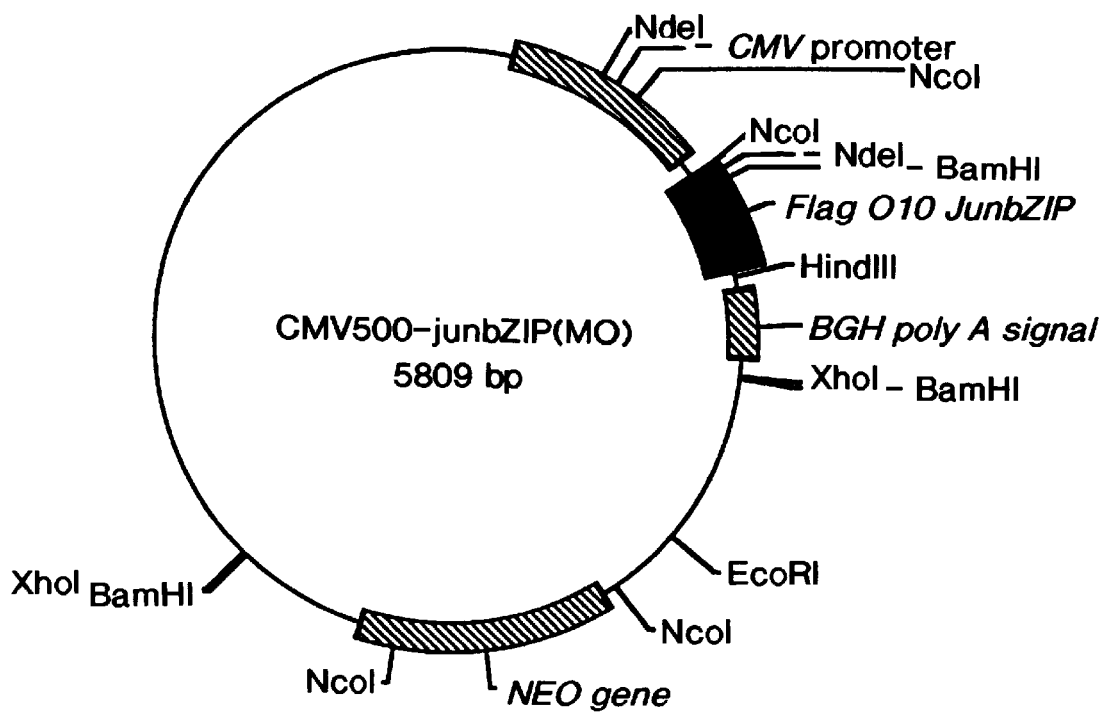
Figure 16C:
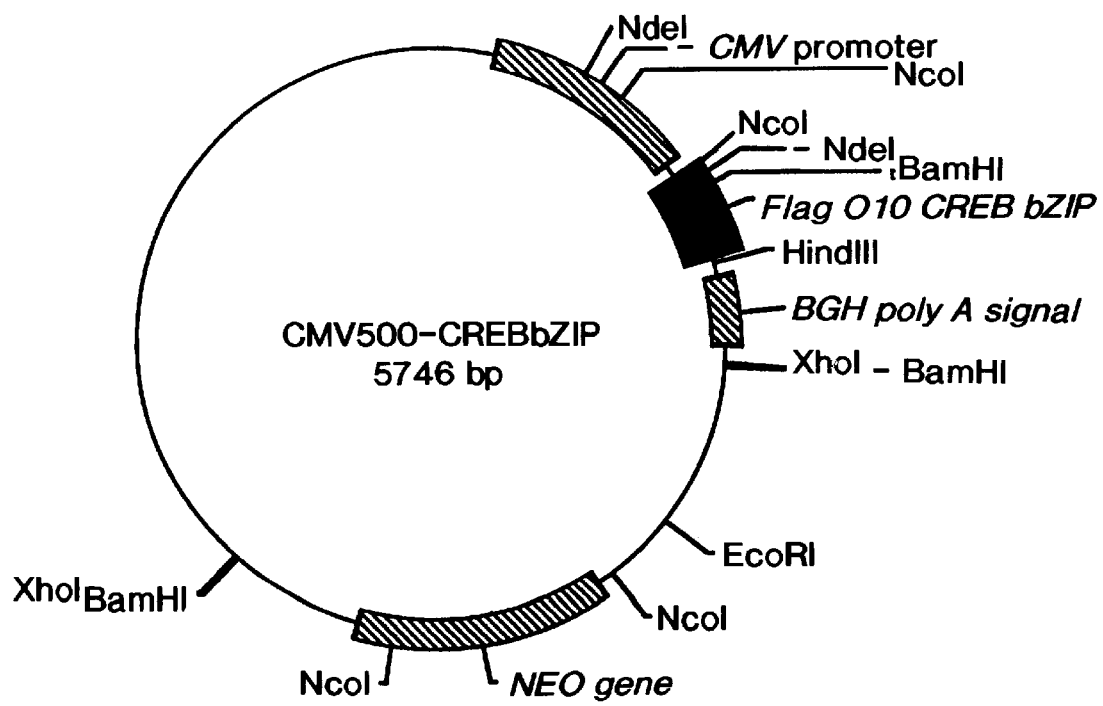

FIGS. 16A and 16B are schematic diagrams of plasmid vectors used in the transfection studies as described. FIG. 16A shows the vector pET3b.seq into which the DNA encoding DNA binding proteins (with and without acidic extensions) are inserted between the BamHI and the HindIII sites. FIG. 16B shows the vector CMV500-junbZip comprising the CMV promoter, and the FLAG and JunbZip sequences inserted between the NcoI and HindIII sites. The sequence range for this vector is from 1 to 5809. Restriction enzyme cleavage sites, the number of cutting sites per enzyme, and their sequence positions are as follows: BamHI: 3 cuts at positions 965, 1571, and 3615; EcoRI: 1 cut at position 2106; HindIII: 1 cut at position 1245; NcoI: 4 cuts at positions 610, 898, 2342, and 3077; NdeI: 2 cuts at positions 484 and 928; and XhoI: 2 cuts at positions 1562 and 3628. FIG. 16C shows the vector CMV500 -CREBbZip comprising the CMV promoter, and the FLAG and CREB-bZip sequences inserted between the NcoI and HindIII sites. The sequence range for this vector is from 1 to 5746. Restriction enzyme cleavage sites, the number of cutting sites per enzyme, and their sequence positions are as follows: BamHI: 3 cuts at positions 965, 1508, and 3552; EcoRI: 1 cut at position 2043; HindIII: 1 cut at position 1182; NcoI: 4 cuts at positions 610, 898, 2279, and 3014; NdeI: 2 cuts at positions 484 and 928; and XhoI: 2 cuts at positions 1499 and 3565.

FIG. 17 depicts the isolated nucleotide sequence (SEQ ID NO:6) and the translated amino acid sequence (SEQ ID NO:7) of a CREB protein having an appended acidic extension. A 5' BamHI restriction site and a 3' HindIII restriction site serve as sites for insertion of the nucleotide sequence into an expression vector, e.g., the pET3b.seq vector of FIG. 16A.

FIG. 18 depicts the isolated nucleotide sequence (SEQ ID NO:8) and the translated amino acid sequence (SEQ ID NO:9) of CMV500-CREBbZIP protein which has no appended acidic extension. A 5' NcoI restriction site and a 3' HindIII restriction site serve as sites for insertion of the nucleotide sequence into an expression vector, e.g., the CMV500-CREBbZip vector of FIG. 16C.

FIG. 19 depicts the isolated nucleotide sequence (SEQ ID NO: 10) and the translated amino acid sequence (SEQ ID NO: 11) of CMV500-4heptadCREB (called New4hepCREB; FIG. 3) protein which has a 4heptad appended acidic extension as described in FIG. 2. A 5' NcoI restriction site and a 3' HindIII restriction site serve as sites for insertion of the nucleotide sequence into an expression vector, such as a vector similar to that shown in FIG. 16C.

Figure 4:
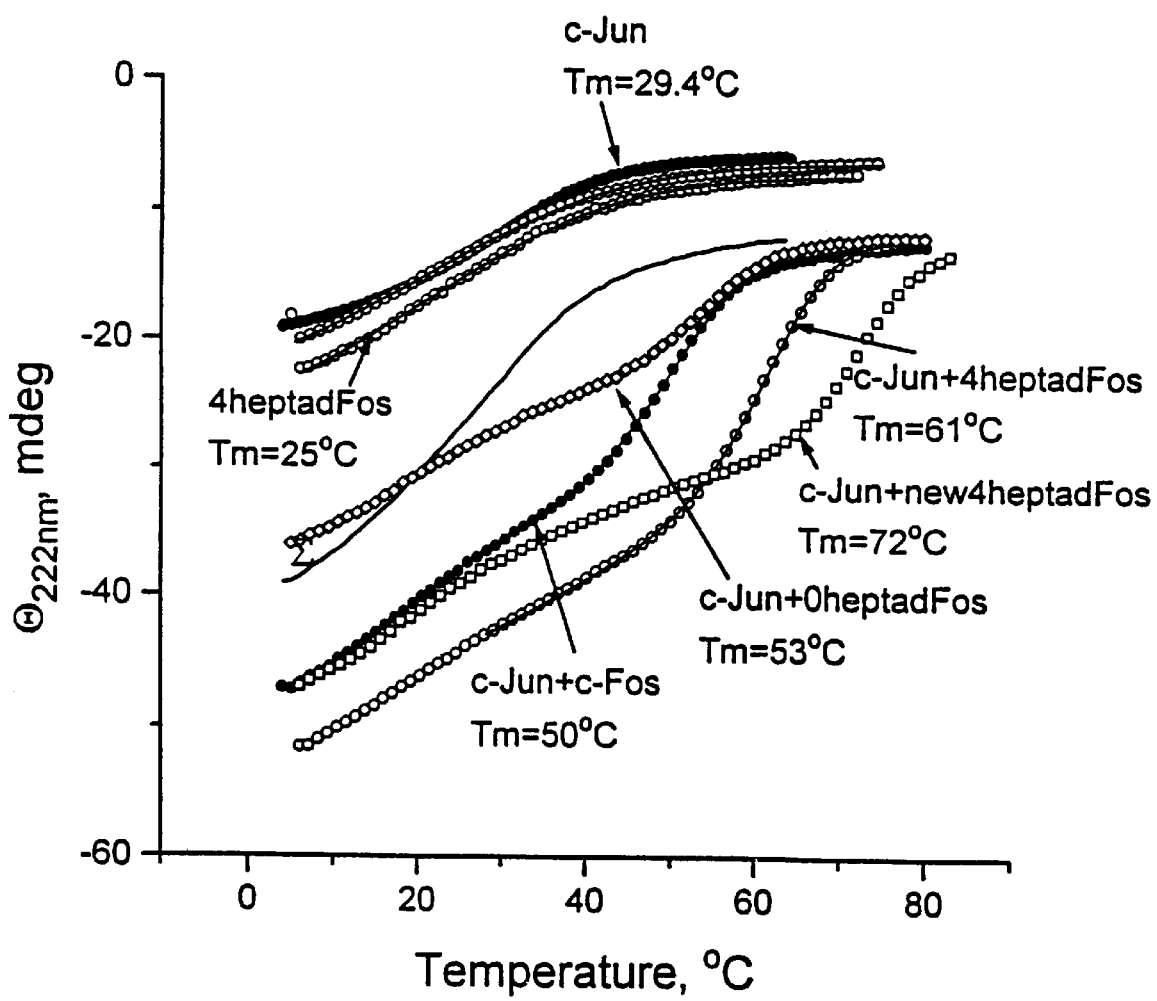
FIG. 4 demonstrates thermal melting curves showing the extent of heterodimerization between the oncogenic DNA binding proteins of the bZIP class, c-Fos and c-Jun, as a consequence of engineering or modifying the expressed c-Fos protein to contain an amino terminal extension of acidic amino acid residues.
Figure 5A:
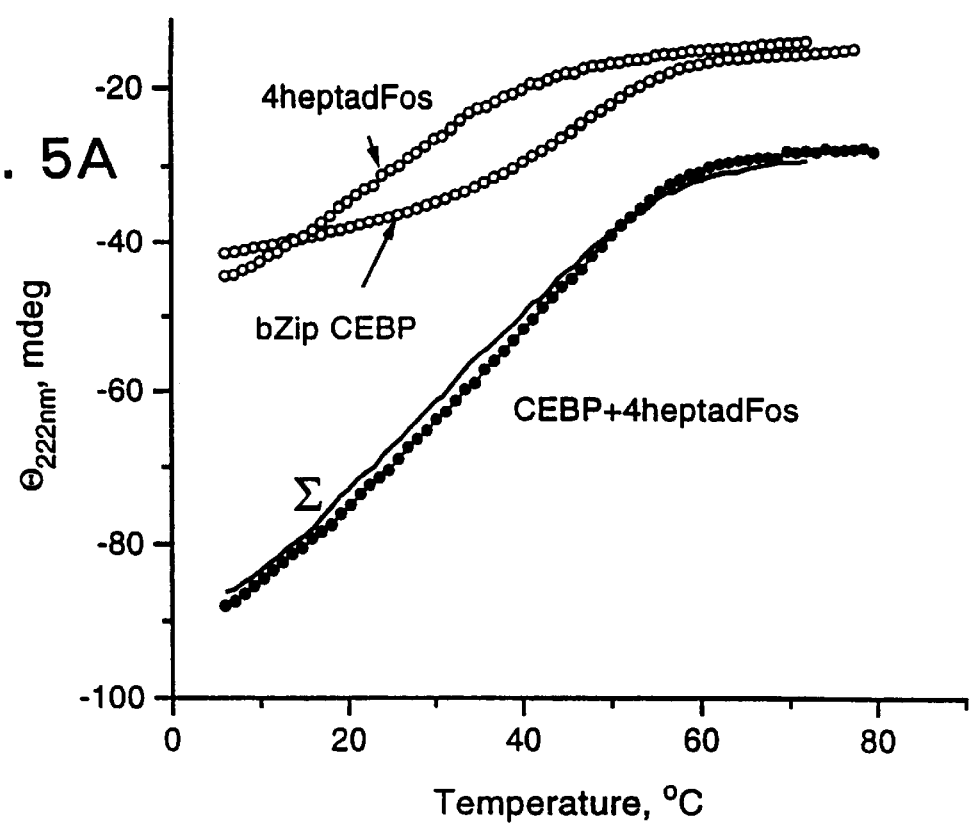
FIGS. 5A and 5B.
Figure 5B:
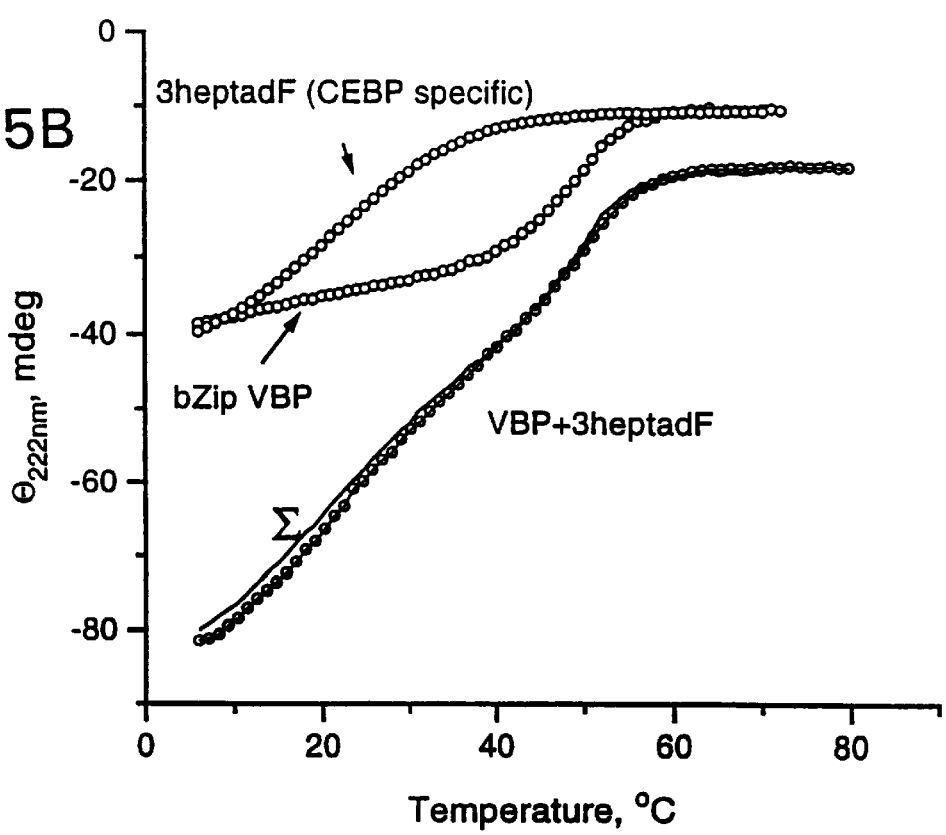
Figure 6:
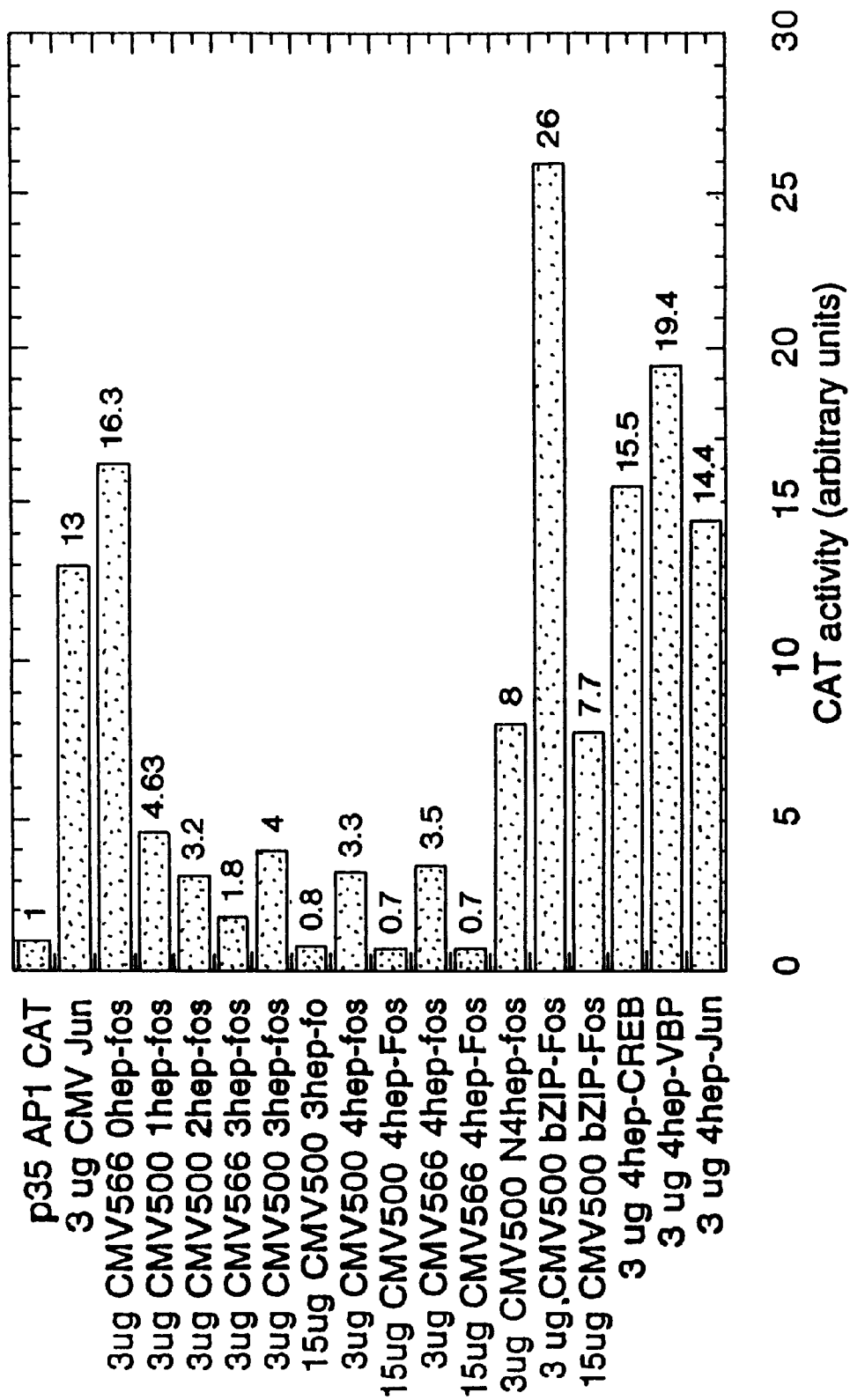
FIG. 6 shows the results of transient transfections of human cells with expression constructs designed to contain cytomegalovirus (CMV) promoter and DNA sequences encoding various DNA binding proteins engineered to have acidic amino acid extensions resulting in expressed acidically modified DNA binding proteins. The constructs harbored DNA sequences encoding the cloned and isolated Fos gene having no acidic extensions (0hep-fos), or the Fos gene sequence modified to encode from 1–4 acidic extensions appended thereto (i.e., 1hep-fos, 2hep-fos, 3hep-fos, and 4hep-fos, respectively). Other constructs contained DNA encoding unmodified Fos (bZIP-Fos); CREB having 4 acidic extensions (4hep-CREB); VBP having 4 acidic extensions (4hep-VBP); and Jun having 4 acidic extensions (4hep-Jun). In these experiments, human hepatoma cells (HepG2) were transiently transfected with up to three plasmids, e.g., a chloramphenicol acetyl transferase (CAT) expression plasmid driven by a single AP1 cis transactivation element, and different DNA binding protein-encoding DNAs. CMV566 AND CMV500 are plasmids containing the cytomegalovirus promoter driving the expression of DNA binding proteins that contain at their N-termini, either the Hemagglutinin or the FLAG epitopes, respectively (Example 4). The histogram presents the extent of transactivation observed in the presence of different combinations of expressed transactivator and various acidically extended, expressed dominant-negative (DN) DNA binding proteins. In the absence of any DN, AP1 transactivation was from approximately 10 to 30 fold. Transactivation was inhibited by 1–3heptad-Fos. The results in FIG. 6 show that an AP1 cis element is activated by Jun transactivation. This activation is inhibited by the acidic extension on the Fos zipper protein (aFos). The acidic extension appended to other leucine zipper proteins did not inhibit AP1 transactivation, thus indicating the specificity of the inhibition.
Figure 7:
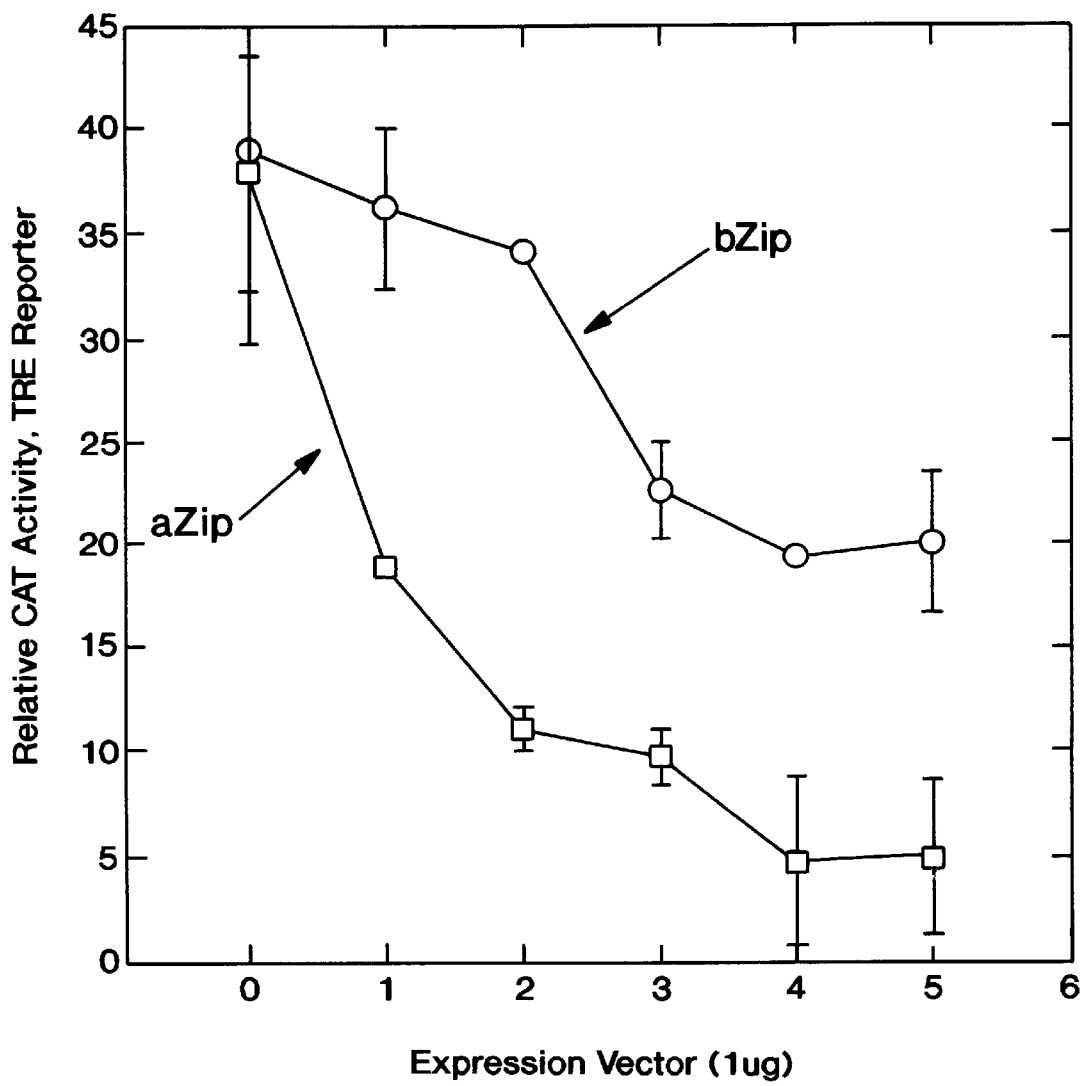
FIG. 7 shows relative CAT activity in an additional cell system (Jurkat) demonstrating that an expressed Fos protein containing an acidic extension (aFos) is a better dominant negative than an expressed Fos protein containing no acidic extension (bFos). Jurkat cells (a B cell model) have a high level of endogenous Fos/Jun (AP1) activity. Cells were transiently transfected with two plasmids (1 μg), namely, a reporter construct containing AP1 cis elements and a second construct containing the CMV500 promoter driving the expression of either a truncated form of Fos (bZipFos) or the Fos leucine zipper containing the 4heptad acidic extension (aFos). AP1 activity was induced by the addition of 12-O-tetradecanoylphorbol (TPA) which results in a 40-fold induction of the reporter gene. The transactivation of the reporter gene occurs because of endogenous AP1 activity. As demonstrated in FIG. 7, expression of the bZipFos protein by the bZipFos construct results in dominant negative activity; however, expression of the aZipFos protein by the aZipFos construct is more efficacious and has a more complete inhibition of AP1 activity.

FIG. 20 depicts the isolated nucleotide sequence (SEQ ID NO:12) and the translated amino acid sequence (SEQ ID NO:13) encoding human c-Fos protein, as used in the experiments described and shown in FIGS. 4–6. A 5' BamHI restriction site and a 3' HindIII restriction site serve as sites for insertion of the nucleotide sequence into an expression vector, such as a vector similar to that shown in FIG. 16A.

Figure 21:
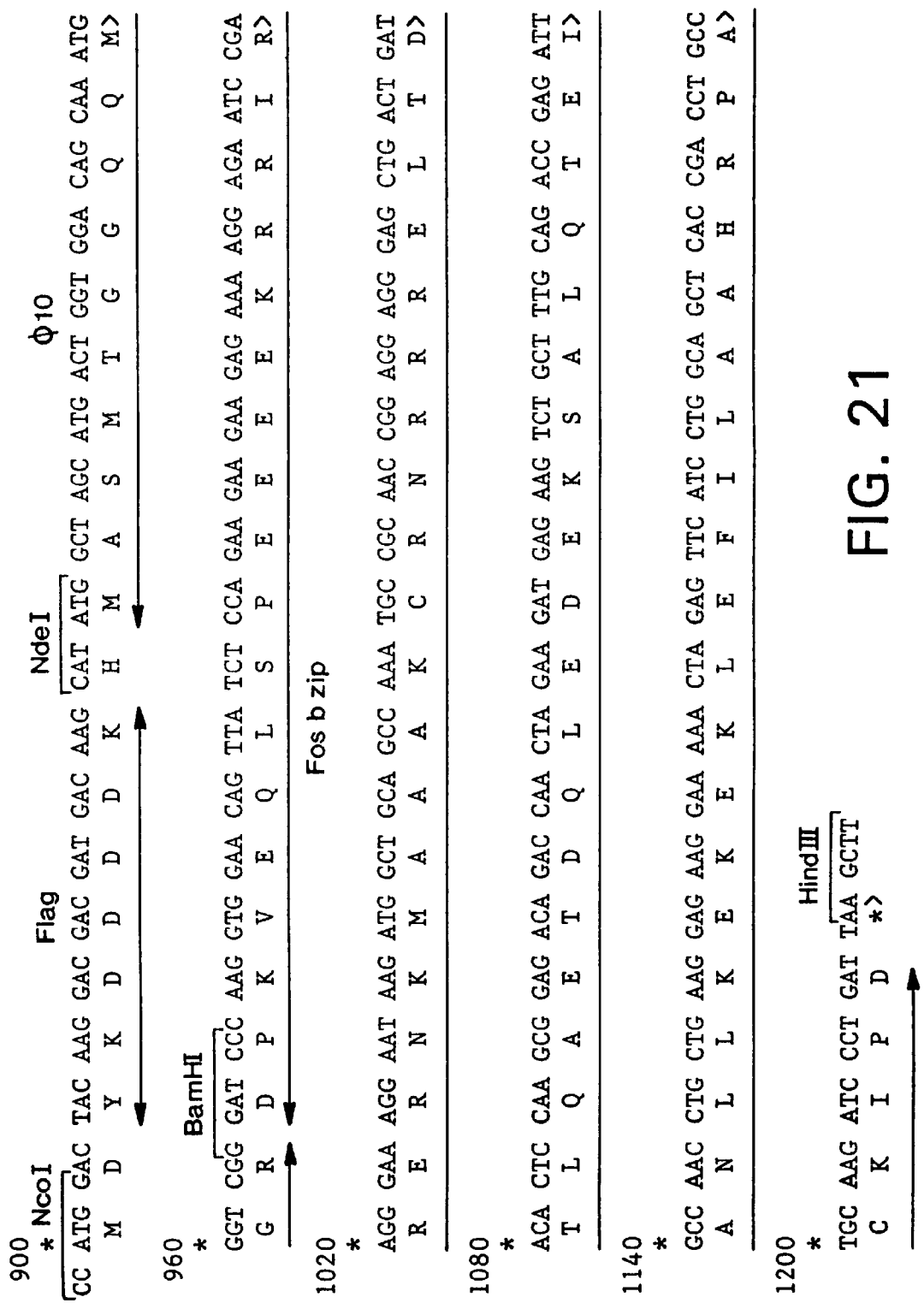

FIG. 21 depicts the isolated nucleotide sequence (SEQ ID NO:14) and the translated amino acid sequence (SEQ ID NO:15) of CMV500-FosbZIP(MO) protein, as used in the experiments described and shown in FIG. 6. A 5' NcoI restriction site and a 3' HindIII restriction site serve as sites for insertion of the nucleotide sequence into an expression vector, such as a vector similar to that shown in FIG. 16C. The nucleotide sequence as shown contains nucleotide sequence encoding the FLAG epitope, nucleotide sequence encoding $\phi$10, and the nucleotide sequence encoding Fos-bZIP.

Figure 2:
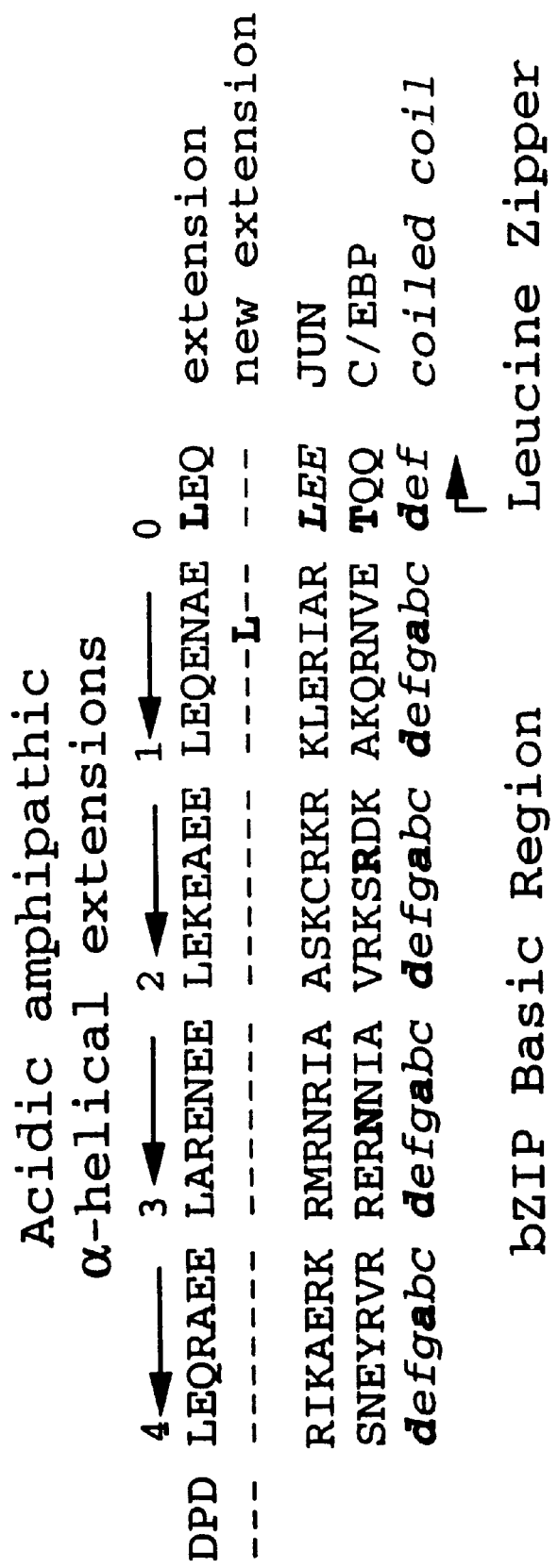
FIG. 2 shows the protein sequence of the 4heptad extension (top line), SEQ ID NO:53, and a modified version of the 4heptad extension (new extension:4heptad) which has one amino acid change (N to L), SEQ ID NO:54, which produces a better dominant negative to the proteins Jun and CREB. Specifically, an asparagine in the a position of the first acidic heptad has been changed to a leucine, resulting in a more potent dominant negative to bZIP proteins containing a hydrophobic amino acid in the same a position, e.g., Jun, CREB, opaque, and ATF2. The basic region of the bZip protein JUN is shown (SEQ ID NO:55) and the basic region of the bZip protein C/EBP is shown (SEQ ID NO:56).
Figure 3:
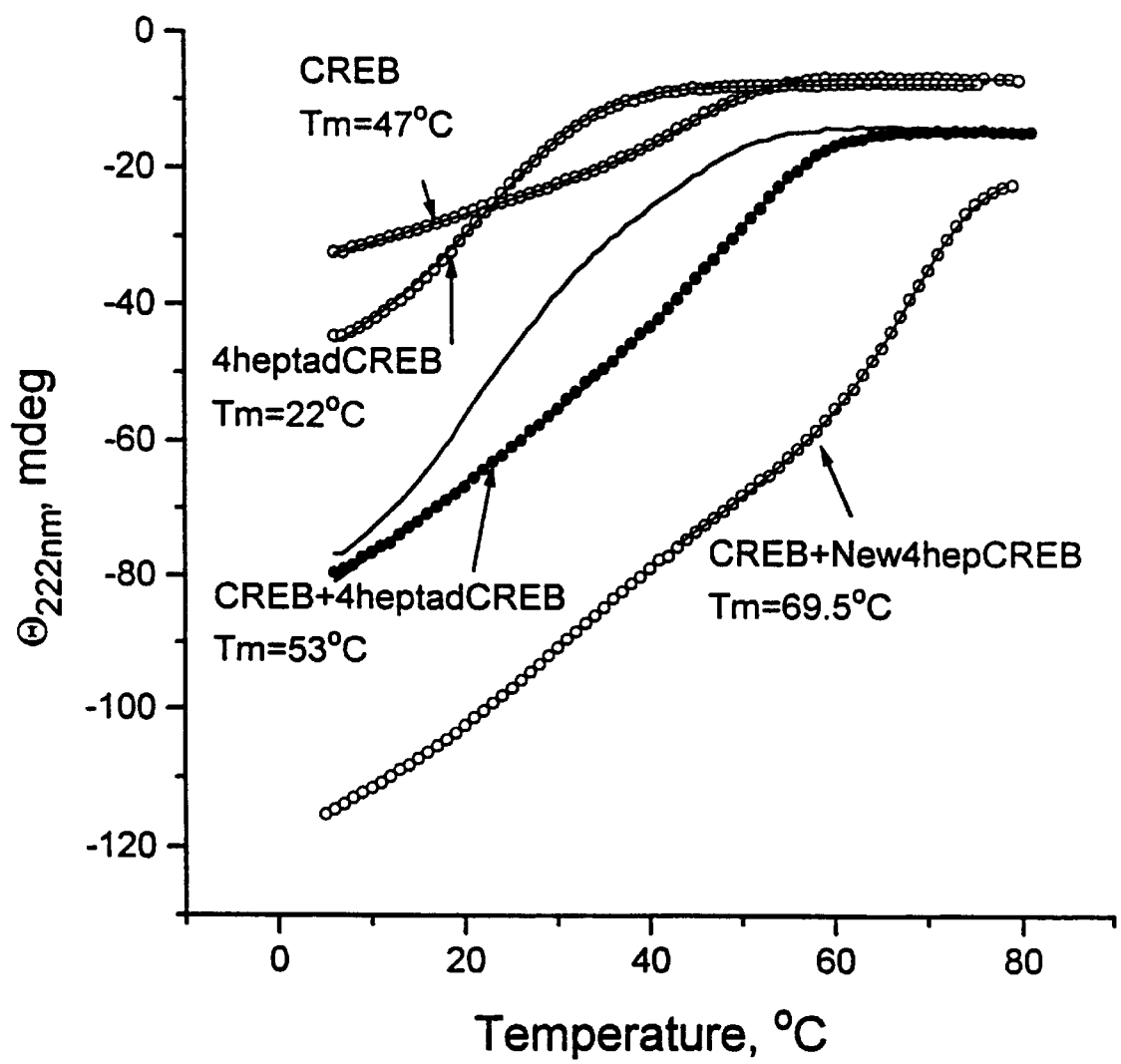
FIG. 3 demonstrates thermal melting curves of CREB. As shown, the melting temperature of unmodified CREB homodimerization is 47° C. (Tm=47° C.) and the melting temperature of CREB containing 4 heptad amino acid residue repeats appended at the amino terminus of the CREB protein (4heptadCREB homodimerization) is 22° C. (Tm=22° C.). The melting temperature of dimerization of the CREB protein with 4heptadCREB is 53° C. (Tm=53° C.). An acidically extended CREB was designed to contain a new acidic extension (New4hepCREB) in which the asparagine was changed to a leucine as described in FIG. 2. As shown, CREB+New4heptadCREB have a melting temperature of 69.5° C. (open circles). This dramatic increase in thermal stability relative to the asparagine-containing acidic extension suggests that different classes of acidic extensions can be used depending on the exact bZIP protein to be inactivated.

FIG. 22 depicts the isolated nucleotide sequence (SEQ ID NO:16) and the translated amino acid sequence (SEQ ID NO:17) encoding the 4heptadFos protein, containing the 4heptad acidic extension as described in FIG. 2 and as used in the experiments described and shown in FIGS. 4, 5A, 6, and 7.

FIG. 23 depicts the isolated nucleotide sequence (SEQ ID NO:18) and the translated amino acid sequence (SEQ ID NO:19) of CMV500-4heptadFos leucine zipper protein, containing the 4heptad acidic extension as described in FIG. 2 and as used in the experiments described and shown in FIG. 6. A 5' NcoI restriction site and a 3' HindIII restriction site serve as sites for insertion of the nucleotide sequence into an expression vector, such as a vector similar to that shown in FIG. 16C. The sequence as shown contains sequence encoding the FLAG epitope, sequence encoding φ10, sequence encoding the 4heptad acidic extension, and sequence encoding the Fos leucine zipper.

Figure 24:
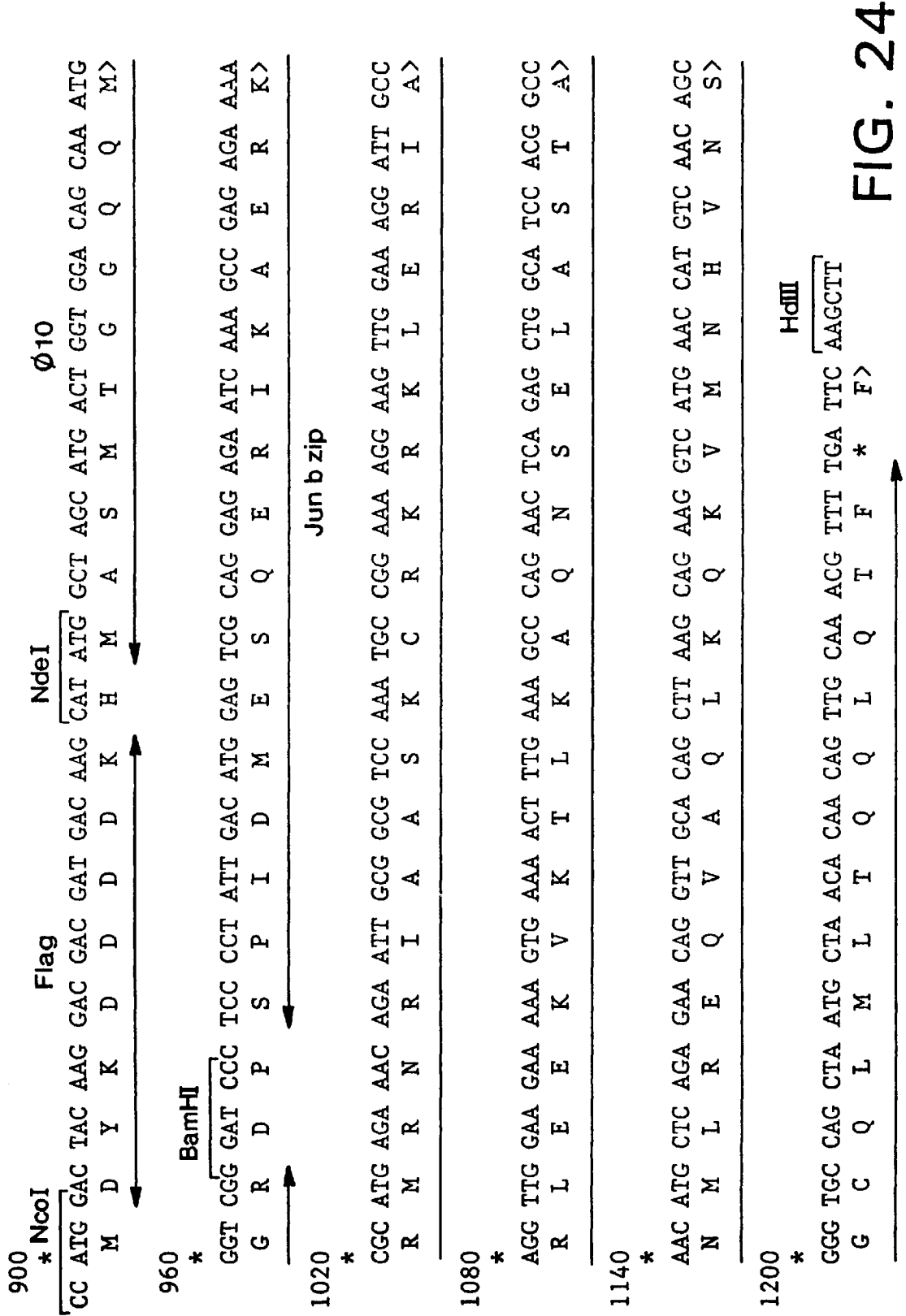

FIG. 24 depicts the isolated nucleotide sequence (SEQ ID NO:20) and the translated amino acid sequence (SEQ ID NO:21) of CMV500-JunbZIP protein. A 5' NcoI restriction site and a 3' HindIII restriction site serve as sites for insertion of the nucleotide sequence into an expression vector, such as the vector shown in FIG. 16B. The sequence as shown contains sequence encoding the FLAG epitope, sequence encoding φ10, sequence encoding the JunbZip protein.

FIG. 25 depicts the isolated nucleotide sequence (SEQ ID NO:22) and the translated amino acid sequence (SEQ ID NO:23) encoding AcidMax, the bHLH Max protein containing an acidic extension comprising a tract of polyglutamic acids appended to the dimerization domain of Max as shown.

FIG. 26 depicts the isolated nucleotide sequence (SEQ ID NO:24) and the translated amino acid sequence (SEQ ID NO:25) encoding 2heptadMax(783), the bHLH Max protein containing two amphipathic acidic extensions, as described in FIG. 9 and in Example 6, appended to the dimerization domain of Max as shown.

FIG. 27 depicts the isolated nucleotide sequence (SEQ ID NO:26) and the translated amino acid sequence (SEQ ID NO:27) encoding 2heptadMax(784), the bHLH Max protein containing two amphipathic acidic extensions, as described in FIG. 9 and in Example 6, appended to the dimerization domain of Max as shown.

FIG. 28 depicts the isolated nucleotide sequence (SEQ ID NO:28) and the translated amino acid sequence (SEQ ID NO:29) encoding 2heptadMax(785), the bHLH Max protein containing two amphipathic acidic extensions, as described in FIG. 9 and in Example 6, appended to the dimerization domain of Max as shown.

FIG. 29 depicts the isolated nucleotide sequence (SEQ ID NO:30) and the translated amino acid sequence (SEQ ID NO:31) encoding murine c-Myc bHLH protein, as used in the experiments described and shown in FIGS. 4–6. Murine, rat and human c-myc sequences are highly conserved and virtually identical. A 5' BamHI restriction site and a 3' HindIII restriction site serve as sites for insertion of the nucleotide sequence into an expression vector, such as a vector similar to that shown in FIG. 16A.

Figure 30:
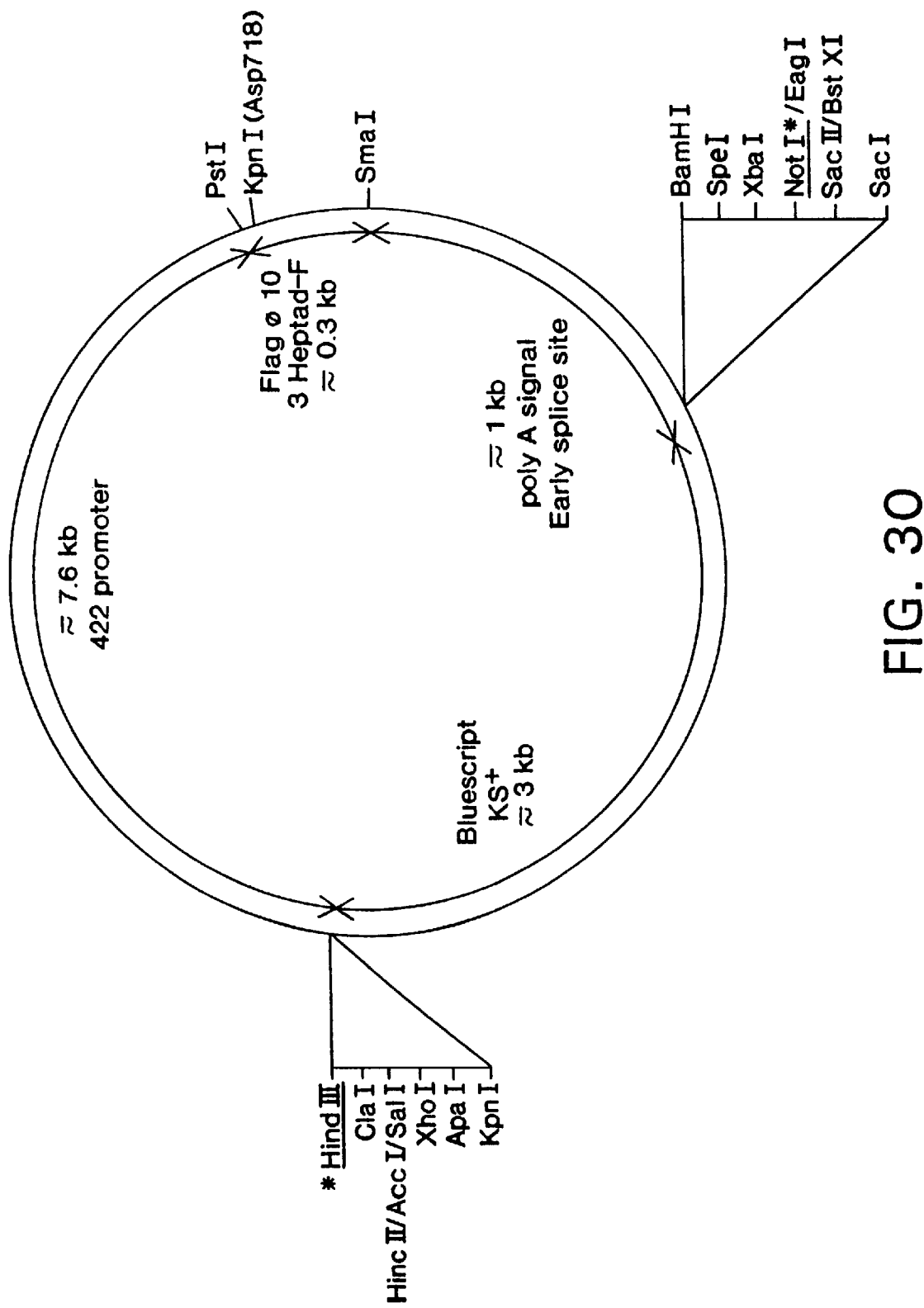

FIG. 30 is a schematic diagram of a plasmid vector (approximately 11.9 kb) which was linearized by cutting with the restriction enzymes HindIII and NotI, as indicated by the asterisks (*). The resulting linearized plasmid DNA contained the 422 or aP2 promoter (approximately 7.6 kb) contained within the HindHIII-PstI site as shown. The 422 or aP2 promoter is known to be associated with the regulation of the expression of adipocyte-specific genes during adipocyte (fat cell) differentiation. The 422/aP2 gene encodes the adipose fatty acid-binding protein. The 5' flanking sequence of the 422/aP2 gene contains regulatory regions for adipose-specific expression (Bernlohr et al., 1985, *J. Biol. Chem.*, 260:5563–5567; Spiegelman et al., 1983, *J. Biol. Chem.*, 258:10083–10089; Cook et al., 1988, *Proc. Natl. Acad. Sci. USA*, 85:2949–2953). The plasmid also contained, operably linked therewith, nucleotide sequence (approximately 0.3 kb) encoding the 3heptadC/EBP dominant negative (Flagφ10 3heptadF), in accordance with the invention as described hereinabove, contained within the KpnI-SmaI site as shown, and a fragment of approximately 1 kb which contained the polyadenylation site from the early region of SV40 and a splice-donor acceptor sequence from the small t antigen intron from SV40 (Gorman et al., 1982, *Mol. Cell. Biol.*, 2:143–190). The insert containing the 422/aP2 promoter, the Flagφ10 3heptadF C/EBP, the polyadenylation and splice sites was cloned between the HindIII and BamHI sites of the polylinker of the vector Bluescript KS+ (Stratagen). The linearized plasmid was used to transfect mice for transgenic mouse production and breeding, employing techniques routinely known in the art.

Figure 31:

FIG. 31 shows the results of the transgenic mouse experiments using the plasmid DNA construct described and shown in FIG. 30. Two litter mates resulting from successful breeding of transgenic animals are shown: the smaller mouse near the left side of the cage exhibits the transgenic phenotype and has the scruffy, scrawny appearance of a skinny or thin mouse, relative to the normal-sized, non-skinny littermate on the right, which does not carry the transgene. The thin, scruffy transgenic mouse as shown in the figure was found to possess several copies of the transgene as assayed by Southern Blot hybridization.

DESCRIPTION OF THE INVENTION

The present invention provides the production of novel multimeric nucleic acid (i.e., DNA or RNA) binding proteins and transcription regulatory proteins which function as potent dominant negative proteins to regulate gene expression and to inhibit cellular protein production and function. Those skilled in the art will appreciate that DNA and RNA are also referred to as polynucleic acids to which the proteins of the invention can bind. These novel proteins are produced by adding acidic amino acid residues (e.g., glutamic acid, aspartic acid) to a dimeric or multimeric protein, e.g., bZIP or bHLH transcription regulatory proteins, such that an engineered acidic extension, comprised of acidic amino acids, is appended onto the protein. For example, a basic region of a multimeric DNA or RNA binding protein can be replaced with an acidic region to yield a dominant negative function. Alternatively, for example, a plurality of acidic amino acids can be appended to a nucleic acid binding protein, preferably onto the N-terminus of the protein, to afford an acidic nature to the resulting protein. As will be appreciated by those having skill in the art, and as exemplified and described herein, the acidically extended nucleic acid binding proteins of the invention are produced using conventional molecular techniques by manipulating isolated DNA sequence encoding a nucleic acid binding protein such that the DNA sequence encoding the dimerization or multimerization domain of the protein contains nucleotides which encode one or more acidic amino acid residues. Also, DNA encoding nucleic acid binding proteins having acidic extensions, or parts of such DNA, e.g., DNA encoding an acidic extension, can be synthetically produced using DNA synthesis techniques conventionally known in the art.

The proteins to which an acidic region has been extended or added can be derived from a variety of protein types, nonlimiting examples of which include DNA or RNA binding proteins, transcription regulatory proteins, such as the bZIP and the bHLH classes of proteins, e.g., fos, jun, opaque, DBP, ATF2, CREB, Max and Myc (e.g., N-myc, C-myc, and v-Myc). Several members of the bZIP class of transcription factors, or structurally similar types of proteins, have functional roles in activating the transcription of genes, the protein products of which are subsequently expressed and function during the growth response of cells. Some of these transcription regulatory proteins are closely linked to tumorigenesis, oncogenesis, and to mediating the production of proteins involved in a variety of aspects of cell growth and differentiation. Such transcription factors are prime candidates for conversion into dominant negatives to control the activity of their wild type counterparts and, ultimately, to regulate or inactivate the function of particular cellular protein products. It will be apparent to those in the art that the terms wild type protein, native protein, naturally occurring protein and non-mutant or non-mutated protein are synonymous as used herein. It will also be understood by those in the art that the nucleic acid binding proteins of the invention may be derived from plants, animals, including mammals and humans, microorganisms such as yeast and fungi, protozoans, algae, and parasites, as well as from RNA and DNA viruses.

More specifically, those skilled in the art are aware that non-mammalian eukaryotic organisms, such as plants, have nucleic acid binding proteins, which are involved with plant physiology. GBF-1 is an example of a plant nucleic acid binding protein of the bZIP class of DNA binding proteins, which binds to the most divergent cis element of the bZIP proteins. Acidic extensions to plant nucleic acid binding proteins are encompassed by the invention to modulate or regulate gene transcription. Indeed, an acidic extension appended onto GBF-1 resulted in stable heterodimerization (see Example 11 and Table 2). In other organisms, preferably eukaryotic and mammalian organisms, tissue specific regulation can be effected by appending an acidic extension onto a molecule such as a protein or polypeptide in accordance with the invention to cause controlled regulation, in particular cell and tissue types, of a cellular protein that is associated with the physiology and endogenous growth of the organism.

Applications for use of the acidically extended proteins in accordance with the invention include the growth of specific organs and tissues by selective regulation of proteins expressed during plant development. For example, storage proteins may modified to achieve healthier and more vigorously-growing plants, vegetables and crops. As another nonlimiting example, plant or crop growth can be augmented or otherwise modified by appending acidic extensions in accordancewith the invention onto suitable endogenous regulatory molecules to increase carbohydrate production, for example, in potato tubers, and the like. The use of acidic extensions appended onto specific proteins, polypeptides, and cellular regulatory molecules is intended to have broad application throughout the plant kingdom. For example, it is envisioned that both monocotyledonous and dicotyledonous plants can be used, as well as stem and leaf vegetables (e.g., broccoli, lettuce, spinach, cabbage), fruit and seed vegetables (e.g., tomato), fiber crops and cereals (e.g., corn, oats, wheat), and forest and ornamental crops (e.g., cotton). In addition, other uses include controlled regulation of proteins to either enhance or decrease the growth of specific plant organs and tissues by reducing the expression or effectiveness of endogenous growth-associated proteins, for example, in fruits (e.g., grapes, citrus fruits, apples, pears, apricots, and the like), or to regulate leaf, root, stem or petiole growth (e.g., cabbage, spinach, celery, beets, soybeans, sugarcane, flower stalks). Plant tissues whose growth and development may be regulated in accordance with the invention can result in the modification of various traits, such as durability, size, succulence, texture, and longevity. The control of the expression of certain genes in accordance with the invention may reduce the expression of growth regulatory genes or genetic control elements that regulate gene expression to result in such nonlimiting and exemplary uses as the dwarfing of stems for durability or enhanced mechanical stability, genetic pruning, stunting, or the elimination of undesirable plant organs.

Examples of candidate nucleic acid binding and transcription regulating proteins suitable for creating dominant negatives to use as inhibitory and regulatory compounds or drugs in accordance with the invention include any dimeric or multimeric DNA binding protein to which an acidic extension may be appended or which can be manipulated to contain acidic amino acid residues. Nonlimiting examples of such proteins are the bZIP family of transcription regulatory proteins having basic and leucine-zipper domains, especially, proteins in the Jun and Fos families, LRF-1 (liver regenerating factor 1), (J. C. Hsu et al., 1991, *Proc. Natl. Acad. Sci. USA,* 88:3511–3515); C/EBP, GCN4, DBP, CHOP-10, GBF-1; and the bHLH family having basic domains and helix-loop-helix motifs, such as ID, MyoD1, E12, c-myc, n-myc, i-myc, max, AP-4, TFE3, USF, and FIP (A. D. Baxevanis and C. R. Vinson, 1993, *Curr. Op. Gen. Devel.,* 3:278–285); as well as other structurally similar proteins.

In a general sense, the invention includes the production of acidically extended nucleic acid binding multimeric complexes, e.g., proteins, polypeptides, or peptides, which bind to a nucleic acid, i.e., DNA or RNA. The products are nucleic acid binding proteins having an acidic extension of amino acids in the dimerization or multimerization domain of the multimeric complex. The multimeric complex will usually have a basic region, which may be replaced with the acidic extension to create molecules which are capable of controlling cell growth and proliferation when such molecules are introduced into and expressed in cells. This is achieved by engineering the nucleotide sequences encoding nucleic acid binding proteins such that nucleotides encoding acidic amino acid residues are present in N-terminal extensions to the basic region or multimerization or dimerization domains of the proteins ultimately expressed.

Dominant negatives (DN) to both bZIP and bHLH proteins containing basic regions, with and without a leucine zipper motif, have been developed and genetically engineered in accordance with the invention by altering and replacing the normal basic domain of the wild type protein with one or more acidic regions. Expression constructs containing DNA sequences which produce the acidically modified DN proteins that function to regulate or control cell growth (e.g. by inhibiting gene transcription or gene activation) when introduced into cells are described.

In one embodiment of the invention, an acidic extension is appended onto an expressed nucleic acid binding protein. Particularly useful nucleic acid binding proteins for use in the invention are DNA binding proteins. In general, one or more acidic amino acid residues comprise the appended acidic extension. The extension can comprise repeating domains or regions, wherein each region or domain comprises a sequence of amino acids, some or all of which are acidic amino acid residues. Each domain or region comprising the appended extension can comprise from two to about one hundred total amino acids, with each domain or region engineered to contain at least one, more preferably two or more, acidic amino acids. An appended acidic extension generally comprises two or more acidic domains or regions comprising a plurality of amino acids appended to the DNA binding protein. The number of acidic domains or regions comprising the acidic extension appended to the protein, as well as the total number of amino acid residues comprising each domain or region, can be modified as desired or required so as to produce an optimum dominant negative or inhibitory function. In general, an appended extension having two or more acidic regions (e.g., heptads) with at least one (e.g., two to five) acidic amino acids in each region, results in more potent dominant negative or inhibitory function. As a particular but nonlimiting example, an acidic extension can contain four heptad amino acid regions or domains comprising twenty-eight total amino acid residues, with at least two amino to four amino acids in each region or domain being acidic (FIG. 2).

In accordance with the invention, a sequence of amino acid residues, at least one of which, preferably two or more, is an acidic amino acid residue, can be appended onto a DNA binding protein to yield an extended protein interaction surface or an extended dimerization interface that is acidic in nature. The invention encompasses an acidic extension which comprises a sequence of acidic amino acid residues, all of which are acidic, e.g., glutamic acid and/or aspartic acid. The invention also encompasses an acidic extension which comprises a sequence of acidic amino acid residues, some of which are acidic. As a general guide, when all of the amino acids in the extension are not acidic, then about 1% to about 98% of the amino acids in the appended sequence can be acidic. Thus, the appended extension can comprise a sequence of amino acids which are not necessarily grouped in regions or domains, some or all of which are acidic residues. As a simple, but nonlimiting example, the appended acidic extension can comprise fifteen to twenty glutamic acid residues appended onto the multimerization or dimerization domain of the nucleic acid binding protein. Accordingly, the total number of amino acids in the sequence of amino acid residues extended onto the protein can be of variable length, for example, from about two to one hundred amino acid residues, preferably from about three to fifty amino acid residues, more preferably from about three to thirty amino acid residues, most preferably from about four to twenty-eight amino acid residues, some or all of which are acidic amino acids. It is to be understood that the length of the acidic extension may impact upon the specificity of dimerization and DNA binding function of the resulting DNA binding protein. In addition, it will be appreciated by those in the art that acidic extensions of varying length (i.e., long and short extensions) can be appended onto a protein to increase or decrease the potency of the resulting dominant negative protein; i.e., to make a stronger or more toxic "drug" comprising the acidically-extended DNA binding proteins of the invention, the number of acidic amino acids in the extension can be increased as required. Those skilled in the art will appreciate that the number of acidic amino acids can be changed to change the strength of an acidically extended protein to suit the needs of the practitioner. For example, a dominant negative DNA binding protein having a short acidic extension (e.g., three to thirteen amino acids) can be created, as well as a dominant negative DNA binding protein having a long acidic extension (e.g., twenty to one hundred amino acids). In general, a longer acidic extension may be expected to provide increase potency, toxicity, or stability to the dominant negative DNA binding protein to which it is appended. The ability to change the strength of the drug afforded by the acidically extended DNA binding proteins of the invention by increasing the number of acidic amino acids comprising the extension allows the resulting proteins to have differential strength as regulators and controllers of cell growth and proliferation.

In another embodiment, the acidically extended DNA binding protein is an expressed bZIP transcription regulatory protein having a basic region and a leucine zipper. In accordance with the invention, the protein is engineered to contain a designed acidic amino acid sequence which extends N-terminally from the leucine zipper region of the expressed bZIP protein. The extension of amino acids can comprise from two to one hundred amino acid residues, preferably from about three to fifty amino acid residues, more preferably from about three to thirty amino acid residues, some or all of which are acidic residues, thereby making the appended amino acid extension acidic in nature. Alternatively, the acidic extension can comprise a sequence of amino acids, all of which are acidic in nature, e.g., glutamic acid, in which the acidic amino acid sequence comprises from about two to eighty amino acids, preferably from about three to fifty amino acids, and more preferably about five to thirty amino acids. It is to be understood that all of the amino acid residues comprising the acidic extension of the bZIP protein can be acidic amino acids or that at least one amino acid residue in each of the amino acid regions comprising an appended extension is an acidic amino acid (e.g., at least one amino acid residue is an acidic residue in each of four heptad repeats comprising the extension, FIG. 2). More frequently, two or more amino acid residues within a given region of an appended extension of the bZIP protein are acidic (FIG. 2; FIG. 11A)

In another embodiment, the extension of amino acids can be amphipathic. As described above, the extension can also be designed to occur in one or more repeating domains or regions. Preferred are acidic extensions comprising one or more amino acid domains or regions, wherein each domain or region of amino acid residues comprises at least one acidic amino acid residues, preferably two or more acidic residues, among the amino acids comprising each region. For example, an acidic extension containing four repeating regions with each region comprising a sequence of seven amino acids comprised of acidic amino acid residues is a 4heptad repeat appended onto the protein in accordance with the invention.

As described, the acidic amino acid sequence can extend for one or more heptad repeats from the N-terminus of the protein and can have an N-terminal cap, which may be comprised of three glycine residues (e.g., DP-GGG). As described herein (Example 1F), the N-terminal cap may also be comprised of other sequences, namely, DP- (aspartic acid and proline alone); DP-D (aspartic acid and proline and aspartic acid); DP-EE (aspartic acid and proline and two glutamic acid residues), and DP-DEEE (aspartic acid and proline and three glutamic acid residues) to replace the DP-GGG cap.

In another embodiment of the invention, the acidically extended DNA binding protein is an expressed transcription regulatory bHLH protein having a basic region and a hexlix-loop-helix structure. In accordance with the invention, the bHLH protein is engineered to contain a designed acidic amino acid sequence which extends N-terminally from the multimerization or dimerization domain of the protein. In these proteins the N-terminal DNA binding amino acids are deleted and replaced with the acidic extension. The acidic extension comprises repeating domains or regions comprised of a sequence of amino acids having at least one acidic amino acid in each repeating region. Alternatively, the acidic extension comprises a sequence of amino acids, some or all of which are acidic, e.g., glutamic and/or aspartic acid. Such an acidic extensions can comprise from two to eighty amino acids, preferably from three to fifty amino acids, and more preferably four to thirty amino acids. It is also to be understood that an acidic extension can simply comprise a sequence of amino acids appended onto the N-terminal multimerization or dimerization domain of a nucleic acid binding protein, wherein some or all of the amino acid residues in the appended extension are acidic. As but one example, an acidic extension appended to a bHLH protein is comprised of fifteen repeating glutamic acid residues. In another example, as described for the bHLH protein, Max (FIG. 9 and Example 6), it was found that an expression construct resulting in the expression of a Max protein having a stretch of polyglutamic amino acid residues appended N-terminally thereto resulted in superior heterodimerization with c-myc protein. Plasmid vectors harboring the DNA sequence encoding acidically modified Max proteins were created using the N-terminal DPD amino acid sequence, which is a BamHI cloning site (Example 6).

The designed acidic region appended onto the protein, e.g., a leucine zipper protein, functioned as a dominant negative to transcription factors comprised of basic regions and leucine zipper regions; basic regions and helix-loop-helix structures, and other DNA binding proteins that are capable of dimerization and/or of binding to a target DNA sequence or gene and regulating or controlling the function of the DNA target sequence or gene to which the DNA binding proteins are bound. In general, specificity is derived from the dimerization domain in the dominant negatives. It will be appreciated that the production of nucleic acid binding proteins which are acidic in nature is applicable to protein-protein interacting systems other than those particularly described and exemplified herein. As but one nonlimiting example, the bHLH family of transcription factors are considered to be good candidates for extending the dimerization motif, because the basic region is an extension of the dimerization region, in a manner that is similar to that of the bZIP protein family.

In another embodiment, the present inventors have designed constructs which contained and expressed isolated DNA encoding a bZIP leucine zipper-containing protein (called the F zipper or heterodimerizing zipper) that preferentially heterodimerized with the wild type bZIP transcription factor C/EBP, a heat-stable DNA-binding protein present in rat liver (W. H. Landschultz et al., 1988, *Genes Dev.*, 2:786–800; C. R. Vinson et al., 1993, *Genes Dev.*, 7:1047–1058). The F-zipper was created by placing charged amino acids in the e and g positions of the coiled coil structure, thereby resulting in the preferential formation of heterodimers over homodimers, as described in C. R. Vinson et al., 1993, *Ibid*. Interestingly, the heterodimer formed by the complexation of native C/EBP and the F zipper constructed without a basic region (i.e., C/EBP:0heptad-F) was more stable than the wild type or native C/EBP homodimer in the absence of DNA. However, the heterodimer was not as stable as the native C/EBP homodimer bound to DNA, and thus, an equimolar amount of the heterodimerizing F zipper without an acidic amphipathic extension (0heptad-F) could not displace native C/EBP from its binding to DNA. Thus, the earlier-produced F zipper was not considered to be a good or useful dominant negative at stoichiometric concentrations.

In accordance with the present invention, the creation of novel multimeric nucleic acid binding proteins containing an acidic extension allows the extension to stretch the protein-protein multimerization or dimerization interface or surface.

A heterodimer complex ultimately formed can be stabilized by over one hundred fold (i.e., 2.5 kcal/mol). For proteins having basic regions, such as bZIP and bHLH proteins, acidic extension allows the extension to increase the protein-protein interaction interface into the basic region of the protein. The acidic extension also can increase the stability of interaction of a heterodimeric complex between the engineered protein containing the acidic extension and the native protein. The increase in heterodimer stability makes the dominant negatives of the invention effective stoichiometric competitors of the wild type or native protein products.

In accordance with the invention and as a particular nonlimiting example, the stability of the heterodimer formed between the wild type C/EBP protein and the F zipper protein was increased by appending a designed three-heptad-long amphipathic α- to the N-terminus of the F zipper (abbreviated 3heptad-F herein), (FIGS. 11A–C). In this way, the acidic extension could electrostatically mimic DNA, thus providing the C/EBP basic region with an alternative interaction surface. In the particular case of C/EBP, the extension of the C/EBP leucine zipper into the basic region would create new a and d positions containing hydrophobic amino acids. For other proteins, such as the bHLH proteins and the like, the acidic extension provides an alternative or extended interaction surface which ultimately controls the extent of binding of a protein to a target DNA sequence (i.e., a gene).

For bZIP proteins, the amino acid sequence of the acidic extension forming a protein interaction surface for binding with the basic region of C/EBP is graphically presented from both a side and an end view (FIGS. 11B–11C). The N-terminal extension was designed to prevent unfavorable stearic or electrostatic interactions with the basic region, and to form attractive electrostatic and hydrophobic interactions that would result in the formation of an appropriate interaction surface. Commercially-available CPK molecular models were used to aid in the molecular design. Leucine was placed in all the d positions of the extension to drive potential hydrophobic interactions. Because the native C/EBP basic region contains two asparagines in the a position, asparagine was placed in the acidic extension to create favorable a⇌a' interactions between the asparagines of the basic region and the acidic extension, as reported for GCN4 leucine zipper structures (T. Ellenberger et al., 1992, *Cell*, 71:1223–1237). In the second and fourth a positions of the native C/EBP basic region is an arginine; the arginine in the second position is conserved in all bZIP proteins. In accordance with the invention, an alanine was placed in the opposing a position of the acidic extension to avoid possible stearic clashes. A glutamic acid was put in the g position to create an attractive g⇌a' electrostatic interaction, to parallel the type of interaction that occurs in the zipper of the c-Fos:c-Jun heterodimer (M. Glover and S. Harrison, 1995, *Nature*, 373:257–261). In addition, glutamic acid was placed in the e and g positions to create favorable g⇌e' interactions. Additional glutamic acids were included in the b and c positions to help electrostatically neutralize the heterodimeric structure. The resulting protein comprising the three heptad N-terminal extension and the F zipper is referred to as 3heptad-F. The hyphen designates the junction between the basic region and the leucine zipper. For heterodimers, the names of the individual proteins comprising the heterodimer are separated by a colon, e.g., C/EBP:3heptad-F.

Also in accordance with the invention, acidic extensions were appended onto the dimerization domain of expressed bHLH proteins, e.g., Max, and heterodimerization with expressed c-myc protein was observed (FIG. 9, Example 6). Increased heterodimerization stability was found when the acidic extension was appended onto the bHLH protein in any of three different orientations, thereby showing the universal nature of the acidic extension to extend protein-protein interaction interfaces of the nucleic acid binding domains of nucleic acid binding proteins, particularly DNA binding proteins.

In accordance with the invention, it was found that the addition of one or more heptads of acidic amino acid sequences onto the N-terminus of a leucine zipper protein stabilized heterodimer formation, as determined by circular dichroism (CD) spectra and thermal melting assays as described herein. This acidic amino acid extension provided an extended protein interaction surface with the basic region of the wild type or native protein containing the leucine zipper and allowed the creation of a dominant negative to the native protein that stoichiometrically displaced the native protein from DNA and inhibited transactivation by the native protein.

It will be appreciated by those in the art that at least one (1heptad) and preferably two to four or more heptads, i.e., 2heptad, 3heptad, 4heptad, and the like (a maximum number can be routinely and empirically determined by those having skill in the art) can be appended to the N-terminal region of appropriate DNA binding proteins to achieve optimal heterodimer binding stability of the proteins produced in accordance with the present invention. However, it is also noted that longer acidic extensions may lead to nonspecificity as a result of an increased interaction with more of the same or similar nucleic acid binding proteins. Such nonspecificity may be alleviated by expressing less protein and/or by employing fewer acidic sequence extensions. A combination of these strategies will allow for the generation of a dominant negative with minimal nonspecific or pleiotropic effects.

In accordance with the invention, plasmid constructs or vectors are provided for the production and expression of the dominant negative nucleic acid binding proteins described. These nucleic acid binding proteins can be expressed, if desired, in a variety of expression systems, particularly eukaryotic and mammalian systems, e.g., yeast, insect, human, hamster, mouse, rat, and the like, using reagents and methods known to those in the art. The constructs for use in both in vitro and in vivo systems are designed to contain at least one promoter, an enhancer sequence (optional, for mammalian expression systems), and other sequences as necessary or required for proper transcription and regulation of gene expression (e.g., transcriptional initiation and termination sequences, origin of replication sites, polyadenylation sequences). As will be appreciated by those skilled in the art, the selection of the appropriate vector and plasmid components for proper transcription, expression, and isolation of proteins produced in eukaryotic and prokaryotic expression systems is known and routinely determined and practiced by those having skill in the art.

Ultimately, the constructs containing the nucleic acid sequences coding for the dominant negative nucleic acid binding proteins of the invention are introduced into cell types of interest, having the appropriate milieu for transcription of the gene(s) whose transcription regulatory proteins and products are to be inhibited or negatively regulated by the dominant negatives of the invention. The constructs can be designed to contain the appropriate and necessary DNA elements for expression of the dominant negative protein in a given cell type, if desired.

For example, the expression of a dominant negative nucleic acid binding protein (e.g., DNA binding protein) having an acidic amino acid extension can be placed under the control of promoters such as viral promoters, e.g., cytomegalovirus (CMV), Rous sarcoma virus (RSV), phosphoglycerol kinase (PGK), thymidine kinase (TK), or the α-actin promoter. Further, a regulated promoter, such as the glucocorticoid response element (GRE) of mouse mammary tumor virus (MMTV), would confer inducibility by glucocorticoids (V. Chandler et al., 1983, Cell, 33:489–499). Alternatively, tissue-specific promoters or regulatory elements can be used (G. Swift et al., 1984, Cell, 38:639–646), non-limiting examples of which include the following: the N-CAM promoter (specific for brain and central nervous system); the PIT-1 promoter (pituitary specific transcription factor); the crystalline promoter (specific for regulating protein expression in the lens of the eye); the keratin promoter (specific for regulating protein expression in the skin); the albumin promoter (liver-specific); the alpha- or beta-globin promoters (specific for red blood cells); the Ig enhancer (specific for B lymphocytes); the T cell receptor α- or β-promoters (specific for T cells); the insulin promoter (specific for pancreatic cells); the gastrin promoter (specific for cells of the stomach); the cardiac actin promoter (specific for heart); the tropomyosin promoter (specific for skeletal muscle); and the lactalbumin promoter and the whey acidic protein (WAP) promoter (A. C. Andres et al., 1987, Proc. Natl. Acad. Sci. USA, 84:1299–1303; C. W. Pittius et al., 1988, Proc. Natl. Acad. Sci. USA, 85:5874–5878), (specific for expression in breast tissue).

Regulated and tissue specific promoters allow the expression of the mutant dominant negative phenotype to be conditional, in general, thereby being exhibited if and when expression of the gene is induced. This would allow the propagation of dominant negative nucleic acid binding proteins of the invention, in the absence of expression of the dominant negative phenotype, so that the inducible dominant negatives can be used in a manner similar to that of temperature sensitive mutations. In addition, since the modification made to DNA binding proteins are dominant and the phenotype is exhibited in the presence of functional wild type genes, the consequences of inactivating the function of genes present in multiple copies can be assessed without having to inactivate each copy of the gene (I. Herskowitz, 1987, Nature, 329:219–222).

As mentioned above, those skilled in the art will appreciate that a variety of promoters, enhancers, and genes are suitable for use in the constructs of the invention, and that the constructs will contain the necessary initiation, termination, and control sequences for proper transcription and processing of the gene of interest when the construct is introduced into a cell. The constructs may be introduced into cells by a variety of gene transfer methods known to those skilled in the art, for example, conventional gene transfection methods, such as calcium phosphate co-precipitation, liposomal transfection, microinjection, electroporation, and infection or viral transduction. In addition, it is envisioned that the invention can encompass all or a portion of a viral sequence-containing vector, such as those described in U.S. Pat. No. 5,112,767 to P. Roy-Burman and D. A. Spodick, for targeted delivery of genes to specific tissues. The choice of the method is within the competence of the skilled practitioner in the art. It will be apparent to those skilled in the art that one or more constructs carrying DNA sequences for expression in cells can be transfected into the cells such that expression products are subsequently produced in and/or obtained from the cells.

In the constructs of the invention, the nucleic acid sequences encoding nucleic acid binding proteins with acidic extensions can be obtained and isolated from natural sources or by synthetic means. For example, using conventionally known techniques in molecular biology, the appropriate DNA sequences can be excised and isolated and purified from genomic clones or from cDNA clones generated from the diverse species known to express nucleic acid binding proteins and the like; the nucleotide sequences can be genetically engineered to encode amino acid residues comprising the acidic extensions as described, and the resulting nucleic acid can then be ligated with at least one of the appropriate or desired segments of DNA sequence to construct a plasmid or vector, comprising, for example, a promoter, an enhancer, terminator site, and polyadenylation site. Alternatively, the nucleic acid sequences can be synthesized for use in the constructs according to all or part of the sequences provided in the sequence ID numbers herein, and in the accompanying figures, by conventional techniques of DNA synthesis, such as the phosphite triester chemistry method (for example, see U.S. Pat. No. 4,415,732 to Caruthers et al.; and Sinha, N. D. et al., 1984, *Nucl. Acids Res.*, 12:4539–4557).

In another aspect of the invention, the acidically extended dominant negatives constructed in accordance with the invention are tested for their in vitro and in vivo functions in inactivating the relevant family of transcription factors in an in vitro or in an in vivo milieu. With regard to in vitro studies, the ability of expressed nucleic acid binding proteins produced in accordance with the invention to inhibit cellular proteins that are associated with cell growth can be assayed using the transient transfection and transformation techniques as described. Such techniques and assays can also be used to screen the engineered, acidically extended nucleic acid binding proteins of the invention for use as candidate anti-cancer or disease drugs and in therapeutic applications.

With regard to in vivo studies, constructs as described for the transient transfection experiments (Examples 1F and 8C) are used to construct transgenic animals, e.g., mice, as described in Example 13. The plasmid constructs carrying the CMV promoter to drive expression of the DNA sequence coding for the DNA binding proteins, e.g., bZIP and bHLH proteins (e.g., 4heptadFos, 4heptadCREB, 2heptadMax, and 3heptad-F proteins), are introduced into animals. Thereafter, the effects of the expression of the acidically extended dominant negatives are monitored in animals harboring the DN transgenes. The animals are assayed for the presence of the transgene and for the expression of the DN protein in cells. Alternatively, DNA sequences encoding the acidically extended dominant negative proteins of the invention are constructed in a vector containing a tissue specific promoter to target the expression of this heterologous gene to specific tissues of the transgenic animals, along with the other components required for a complete vector construct.

Another aspect of the invention provides tissue specific constructs which will target those tissues in which the acidic extension-containing nucleic acid binding proteins are to be expressed. Such constructs are designed to contain tissue-specific promoters such as those enumerated hereinabove, and a DNA sequence encoding a DNA binding protein having acidic extensions, e.g., the 4heptadFos, 4heptadCREB, 3heptadMax, or other transcription factors, the expression of which will be driven by the tissue-specific promoter, and the appropriate initiation and termination sites for transcription, and polyadenylation sites, if necessary, for expression in a given cell and tissue type. Thus, the invention allows the selective expression and the determination of the function of DNA binding protein family members, such as those of the bZIP and bHLH families, in individual tissues by means of the production of transgenic organisms and via genetic therapy approaches known and used in the art.

Figure 1:
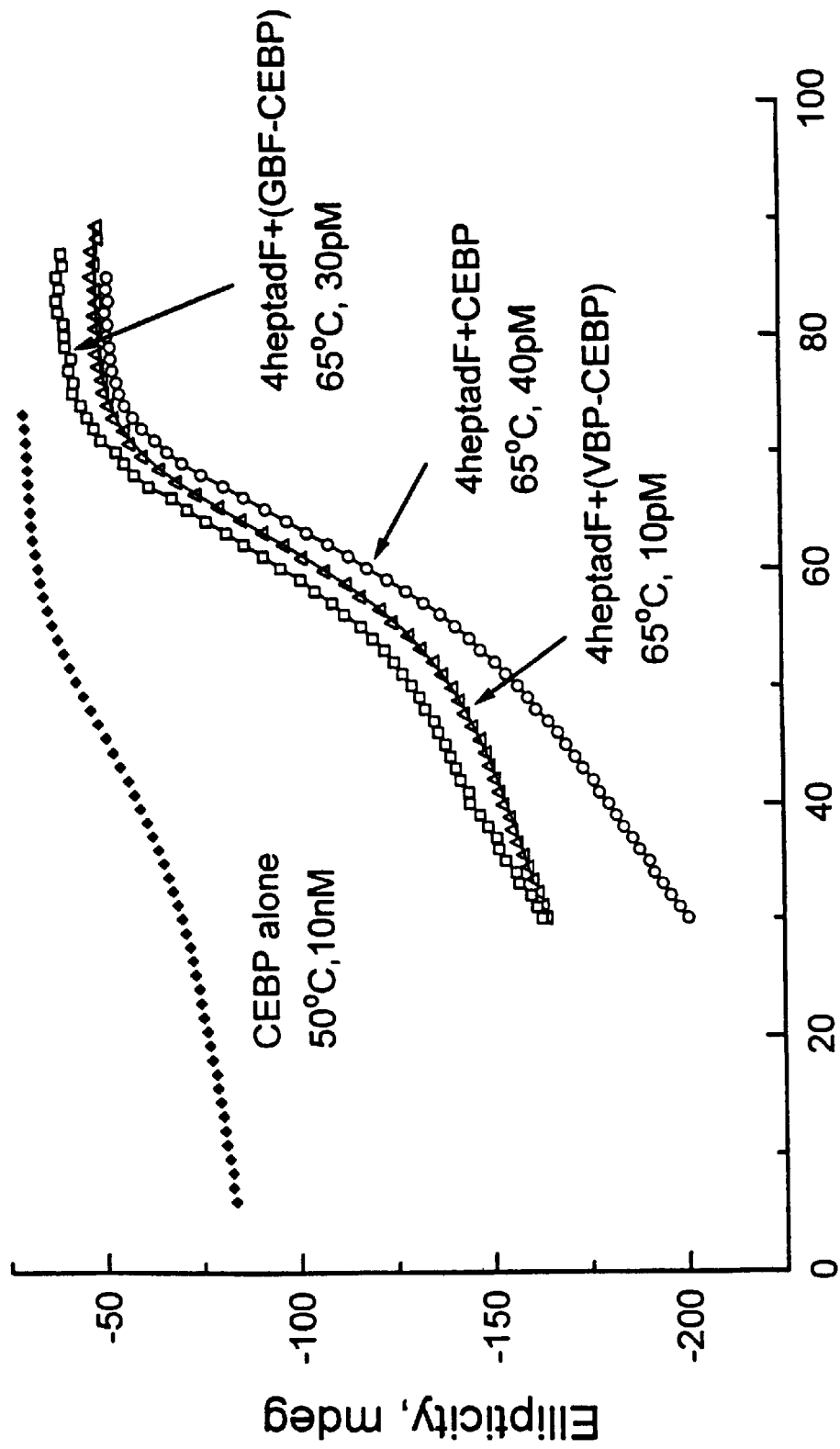
FIG. 1 shows thermal melts of chimeric proteins containing the CEBP leucine zipper and three bZIP basic regions derived from CEBP, VBP and GBF (CEBP, VBP-CEBP, and GBF-CEBP) mixed with the dominant negative 4heptad-F. The results show that the 4heptad acidic extension interacts similarly with three, different basic proteins, i.e., the ellipticity for all three is 65° C.

For gene therapy applications of the present invention, constructs designed to carry the acidically extended nucleic acid binding proteins, e.g. DNA binding transcription regulatory proteins, RNA binding proteins, and the like, as described herein can supply the described DN protein inactivation function to a variety of cell types, including stem cells, differentiated cells, germ cells, and oncogenic or transformed cells. Supplying such an inactivating or inhibitory function by the dominant negatives of the invention can lead to and/or cause the suppression of neoplastic growth in a variety of cell types, especially those cells which have been growth-altered, for example, as a consequence of the interaction and activity of Fos-Jun dimerization (Examples 2 and 4 and FIGS. 1 and 4) or Myc-Max dimerization (Examples 6 and 7 and FIG. 9). In addition, because of the divergent biological roots of the DNA binding proteins, the DN constructs afforded by the invention are applicable to the areas of human biology, non-human mammalian biology, insect biology, and plant biology. In the latter case, the dominant negatives can modulate the expression of valuable gene products related to plant stress, anti-fungal agents, insecticides, and pesticides.

The dominant negatives, or a dominant negative-functioning part or fragment thereof, in accordance with the invention, can be introduced into a cell in a vector such that the DNA segment remains extrachromosomal and will be expressed by the cell from the extrachromosomal location in the cell. Vectors for the introduction of genes and DNA segments suitable for both recombination and extrachromosomal maintenance are known in the art. Cells transformed or transfected with the DN-containing constructs of the invention can be used as model systems to study cancer or tumor remission.

Gene transfer systems known in the art may be useful in the practice of the invention. Both viral and non-viral methods are suitable. Numerous viruses have been used as gene transfer vectors, including papovaviruses, e.g., Simian Virus 40, (SV40), adenovirus, vaccinia virus, adeno-associated virus, herpes viruses, including Herpes Simplex Virus, (HSV) and Epstein Barr Virus, (EBV), and retroviruses of avian, murine, and human origin. As is appreciated by those in the art, most human gene therapy protocols have been based on disabled murine retroviruses. Recombinant retroviral DNA can also be employed with amphotropic packaging cell lines capable of producing high titer stocks of helper-free recombinant retroviruses (e.g., R. Cone and R. Mulligan, 1984, *Proc. Natl. Acad. Sci. USA*, 81:6349).

Receptor-mediated gene transfer methods allow targeting of the DNA in the construct directly to particular tissues. This is accomplished by the conjugation of DNA (frequently in the form of covalently-closed supercoiled plasmid) to a protein ligand via poly-lysine. The appropriate or suitable ligands are selected on the basis of the presence of the corresponding ligand receptors on the cell surface of the target cell or tissue type. These ligand-DNA conjugates can be injected directly into the blood, if desired, and are directed to the target tissue where receptor binding and DNA-protein complex internalization occur. Co-infection with adenovirus to disrupt endosome function can be used to overcome the problem of intracellular destruction of DNA.

Nonviral gene transfer methods known in the art include chemical techniques, such as calcium phosphate co-precipitation, direct DNA uptake and receptor-mediated DNA transfer, and mechanical means, such as microinjection and membrane fusion-mediated liposomal transfer. In addition, viral-mediated gene transfer can be combined with direct in vivo gene transfer using liposomes, thereby allowing the delivery or the viral vectors to tumor cells, for example, and not to surrounding non-proliferating cells. The retroviral vector producer cell line can be injected directly into specific cell types, e.g., tumors, to provide a continuous source of viral particles, such as has been approved for use in patients afflicted with inoperable brain tumors.

An approach that combines biological and physical gene transfer methods utilizes plasmid DNA of any size combined with a polylysine-conjugated antibody specifically reactive with the adenovirus hexon protein. The resulting complex is bound to an adenovirus vector. The trimolecular complex is then used to infect cells. The adenovirus vector allows efficient binding to the cell, internalization, and degradation of the endosome before the coupled DNA can be damaged.

The described constructs may be administered in the form of a pharmaceutical preparation or composition containing a pharmaceutically acceptable carrier and a physiological excipient, in which preparation the vector may be a viral vector construct, or the like, to target the cells, tissues, or organs of the recipient organism of interest, including human and non-human mammals. The composition may be formed by dispersing the components in a suitable pharmaceutically-acceptable liquid or solution such as sterile physiological saline or other injectable aqueous liquids. The amounts of the components to be used in such compositions may be routinely determined by those having skill in the art. The compositions may be administered by parenteral routes of injection, including subcutaneous, intravenous, intramuscular, and intrasternal. Other modes of administration include intranasal, intrathecal, intracutaneous, percutaneous, enteral, and sublingual. For injectable administration, the composition is in sterile solution or suspension or may be emulsified in pharmaceutically- and physiologically-acceptable aqueous or oleaginous vehicles, which may contain preservatives, stabilizers, and material for rendering the solution or suspension isotonic with body fluids (i.e. blood) of the recipient. Excipients suitable for use are water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures.

It is also envisioned that the nucleic acid binding proteins of the invention can be used to screen compounds using the expressed acidically extended nucleic acid binding proteins or a functional binding fragment thereof in a variety of drug screening methods. For example, an engineered and expressed DNA binding protein or fragment employed in such a test may either be flee in solution, affixed to a solid support, or displayed on a cell surface. One drug screening technique utilizes eukaryotic or prokaryotic host cells which are stably transformed with recombinant polynucleotides expressing the protein or fragment, preferably in competitive binding assays. Such cells, either in viable or fixed form, can be used in standard binding assays. For example, the formation of complexes between a nucleic acid binding protein or fragment and the agent being tested may be quantified, or the degree to which the formation of a complex between a nucleic acid binding protein or fragment and a known ligand is interfered with by the agent being tested can be examined.

Thus, the present invention provides methods of screening for drugs comprising contacting such an agent with a nucleic acid binding protein of the invention or fragment thereof and assaying (i) for the presence of a complex between the agent and the nucleic acid binding protein or fragment, or (ii) for the presence of a complex between the nucleic acid binding protein or fragment and a ligand, by methods well known in the art. In such competitive binding assays, the nucleic acid binding protein or fragment is typically labeled. Free nucleic acid binding protein or a fragment is separated from that present in a protein:protein complex, and the amount of free (i.e., uncomplexed) label serves as a measure of the binding of the agent being tested to the nucleic acid binding protein or of its interference with the nucleic acid binding protein:ligand binding, respectively.

Another technique for drug screening provides high through screening for compounds having suitable binding affinity to the DNA binding proteins and is described in detail in Geysen, European Patent Application 84/03564, published on Sep. 13, 1984. In brief, large numbers of different small peptide test compounds are synthesized on a solid substrate, such as plastic pins or some other surface. The peptide test compounds are reacted with the DNA binding protein and washed. After washing, bound DNA binding protein is then detected by methods well known in the art. Alternatively, purified DNA binding protein can be coated directly onto plates for use in the aforementioned drug screening techniques. However, non-neutralizing antibodies to the polypeptide can be used to capture antibodies to immobilize the DNA binding protein on the solid phase.

The invention also contemplates the use of competitive drug screening assays in which antibodies capable of specifically binding the DNA binding protein compete with a test compound for binding to the DNA binding protein or fragments thereof. In this manner, the antibodies can be used to detect the presence of any peptide which shares one or more antigenic determinants with the DNA binding protein.

Rational drug design is also envisioned as a use for the present invention. In general, the goal of rational drug design is to produce structural analogs of biologically active polypeptides and proteins of interest or of small molecules with which they interact (e.g., agonists, antagonists, inhibitors) in order to fashion drugs which are, for example, more active or stable forms of the protein or polypeptide, or which, for example, enhance or interfere with the function of a protein or polypeptide in vivo. See, e.g., Hodgson, 1991. In one approach, the three-dimensional structure of a protein of interest (e.g., an acidically extended DNA binding protein of the invention) is first determined by x-ray crystallography, by computer modelling or most typically, by a combination of approaches. Less often, useful information regarding the structure of a polypeptide may be gained by modeling based on the structure of homologous proteins. The production and design of nucleic acid binding proteins having acidic amino acid extensions can lead to the expression, production and detection of products having an increased affinity for binding to cognate cellular proteins than do the normal, unmodified cellular counterparts. Upon complexation with its naturally occurring cognate cellular nucleic acid (e.g., DNA) binding protein, an acidically extended nucleic acid binding protein of the invention can inhibit or prevent the function of its cognate protein and ultimately affect cellular gene transcription and expression. Thus, the products designed and created in accordance with the invention can yield more potent dominant negatives of wild type or naturally occurring proteins.

Accordingly, drugs may be designed which have, e.g., improved DNA binding function, activity or stability or which act as more potent dimerization molecules, or as inhibitors, agonists, antagonists, etc. of DNA protein binding activity. By virtue of molecularly synthesizing the DNA binding protein sequences, sufficient amounts of the proteins may be made available to perform such analytical studies as X-ray crystallography. In addition, DNA sequence of the DNA binding protein will allow computer modeling techniques to be employed in place of or in addition to x-ray crystallography.

Active nucleic acid binding protein molecules can be introduced into cells by microinjection or by use of liposomes, for example. Alternatively, some functioning molecules may be taken up by cells, actively or by diffusion. Extracellular application of the gene product of the acidically extended DNA binding proteins of the invention may be sufficient to affect tumor growth, provided that the gene products become localized in the nucleus. The supply of molecules with the activity of an acidically extended DNA binding protein should lead to partial reversal of the neoplastic state. Other molecules with acidically extended nucleic acid binding protein activity (for example, peptides or functional portions thereof) may also be used to effect such a reversal. Modified polypeptides having substantially similar function are also used for peptide therapy.

EXAMPLES

The examples herein are meant to exemplify the various aspects of carrying out the invention and are not intended to limit the invention in any way.

Example 1

Materials and Methods
A. Nucleic Acids, Plasmids, and Proteins

Plasmid constructs harboring DNA encoding the nucleic acid binding proteins, both with and without acidic extensions, for cell expression were produced using routine methods, protocols and reagents in the art. Constructs for the expression of the 4heptad-F zipper protein were built to contain the cytomegalovirus (CMV) promoter, the FLAG epitope (Invitrogen), and the nucleic acid sequence shown in SEQ ID NO:32. The DNA sequence depicted by SEQ ID NO:32 contains an N-terminal leader sequence (described below in SEQ ID NO:33), three glycine (GGG) residues (nucleotides 43–51), which, when deleted, produce a more effective dominant negative, as described herein (see Example 1F), the 4heptad sequence depicted in SEQ ID NO:38, and the F-zipper DNA sequence embraced by SEQ ID NO:34.

SEQ ID NO:32 is as follows:

```
1
ATG GCT AGC ATG ACT GGT GGA CAG CAA ATG GGT CGG
 M   A   S   M   T   G   G   Q   Q   M   G   R

GAT CCT GGC GGT GGC CTG GAA CAA CGT GCT GAG GAA
 D   P   G   G   G   L   E   Q   R   A   E   E

CTG GCC CGT GAA AAC GAA GAG CTG GAA AAA GAG GCC
 L   A   R   E   N   E   E   L   E   K   E   A

GAA GAG CTG GAG CAG GAA AAC GCT GAA CTC GAG CAG
 E   E   L   E   Q   E   N   A   E   L   E   Q

GAA GTG TTG GAG TTG GAA AGT CGT AAT GAC CGC CTG
 E   V   L   E   L   E   S   R   N   D   R   L

CGC AAG GAA GTG GAA CAG CTG GAG CGT GAA CTG GAC
 R   K   E   V   E   Q   L   E   R   E   L   D
```

-continued
```
ACG CTG CGG GGT ATC TTC CGC CAG CTG CCT GAG AGC
 T   L   R   G   I   F   R   Q   L   P   E   S

296
TCC TTG GTC AAG GC CATGGGCAACTGCGCGTGAGGCGAATTCAA
 S   L   V   K   A
```

The protein sequences expressed from the constructs transformed into *E. coli*, produced in vivo, and isolated and purified as described herein are listed below. In each protein, the initiator methionine is processed off in *E. coli*. The conventional one-letter symbols for abbreviating amino acid residues are used herein and are as follows: A (alanine); C (cysteine); D (aspartic acid); E (glutamic acid); F (phenylalanine); G (glycine); H (histidine); I (isoleucine); K (lysine); L (leucine); M (methionine); N (asparagine); P (proline); Q (glutamine); R (arginine); S (serine); T (threonine); V (valine); W (tryptophan); and Y (tyrosine).

All proteins, except for C/EBP and GBF-C/EBP, have a 13 amino acid N-terminal leader sequence as follows: ASMTGGQQMGRDP-(SEQ ID NO:33).

The F-zipper amino acid sequence is:

GGGTQQEVLELESRNDRLRKEVEQLER-ELDTLRGIFRQLPESSLVKAMGNCA (SEQ ID NO:34).

The amino acid sequences of the multiheptad-containing zippers are provided below. The L in the penultimate position in the heptad sequences is the first "L" position of the F leucine zipper. Those skilled in the art will be aware that the nucleic acid sequences, i.e., the triplet codons, corresponding to the various amino acid sequences presented herein and for use in the presently claimed invention can be determined in a conventional manner in accordance with the genetic code.

1heptad-F GGGLEQENAELE (SEQ ID NO:35);
2heptad-F GGGLEKEAEELEQENAELE (SEQ ID NO:36);
3heptad-F GGGLARENEELEKEAEELEQENAELE (SEQ ID NO:37);
4heptad-F GGGLEQRAEELARENEELEKEAEELEQE-NAELE (SEQ ID NO:38);
3heptad-F (cap)GGGLARNNIAVRKSRDKAKQRNVELE (SEQ ID NO:39);
3heptad-F (cap, a d) GGGLARNNIALRKSADKLKQRN-VELE (SEQ ID NO:40);
3heptad-F (cap, e g) GGGLARENIAVEKERDKAEQEN-VELE (SEQ ID NO:41);
3heptad-F (cap, b c) GGGLARNNEEVRKSREEAKQR-NAELE (SEQ ID NO:42).

Three bZIP domains described and utilized herein are shown in 1)–3) below. Unless otherwise noted, the nucleic acid sequences corresponding to the protein sequences of the chimeric bZIP proteins are those reported in the referenced publications.

1) The chimeric sequence of GCN4-C/EBP protein is depicted with the GCN4 sequence in italics:

SEYQPSLFALNPMGFSPLDGSKSTNENV-SASTSTAKPMVGQLIFDKFIKTEEDP GKAKKSVD-KNSNEYRVRRERNNIAVRKSRDKAKQRNVE TQQKVLELTSDNDRLRKRVEQLSRELDTLRGIFR QLPESSLVKAMGNCA, (SEQ ID NO:43). Cloning of GCN4 and its corresponding nucleic acid sequence have been described by A. G. Hinnebusch, 1984, *Proc. Natl.*

*Acad. Sci. USA,* 81:6442. The isolation and nucleic acid sequence of the gene encoding C/EBP are described in W. H. Landschulz et al., 1988, *Genes Dev.,* 2:786–800.

2) The polypeptide sequence of the GBF-C/EBP chimeric protein:

PVKDERELKRQKRKQSNRESARRSRLR-NEAECEQTQQKVLELTSDNDRLRKR VEQLSRELDTLRGIFRQLPESSLVKAMGNCA (SEQ ID NO:44). Cloning of the Arabidopsis thaliana-derived bZIP protein, GBF, and its corresponding nucleic acid sequence have been described in U. Schindler et al., 1992, *The EMBO J.,* 11:1261–1273.

3) The polypeptide sequence of the VBP-C/EBP chimeric protein:

ASMTGGQQMGRDPLEEKVFVPDEQKDE-KYWTRRKKNNVAAKRSRDARRLK ENQTQQKV-LELTSDNDRLRKRVEQLSRELDTL-RGIFRQLPESSLVKAMGNCA (SEQ ID NO:45). Cloning of the chicken vitellogenin gene-binding protein VBP and its corresponding nucleic acid sequence have been described by S. Iyer et al., 1991, *Mol. Cell. Biol.,* 11:4863–4875.

B. Protein Expression and Purification

Proteins with and without acidic extensions were expressed in *E. coli* and isolated and purified from culture supernatants. More particularly, proteins were synthesized in *E. coli* using the phage T7 expression system (F. Studier and B. Moffatt, 1986, *J. Mol. Biol.,* 189:113–130. Bacterial cultures (about 400 mL) were induced with 1 mM isopropyl-b-D-thiogalactopyranoside) at an optical density of 0.6 at 600 nm for about 2 hours. Cells were then recovered by centrifugation, resuspended in 6 mL of lysis buffer (50 mM Tris-HCl, pH 8.0, 1 mM EDTA, 1 mM benzamidine, 1 mM dithiothreitol (DTT), and 0.2 mM phenylmethylsulfonyl fluoride (PMSF)), frozen, thawed, and gently brought to 1 M KCl by the addition of 2 mL of 4 M KCl. The sample was centrifuged at 25,000 rpm in a Beckman T42 rotor, and the supernatant was removed and isolated. The isolated supernatant was then heated to 65° C. for 10 minutes and centrifuged, and the supernatant was isolated. The proteins that were capable of binding DNA were diluted to 100 mM KCl and purified over a heparin-agarose column as described by D. Krylov et al., 1994, *EMBO J.,* 13:1849–1861, and were subsequently purified over a Rainin HPLC system. The proteins lacking DNA binding domains were purified over a Mono Q Sepharose column and eluted with 200 mM, 400 mM, and 600 mM KCl. The fractions enriched in the proteins were then purified on a Rainin HPLC system using a C18 column chromatographed from 0% to 100% acetonitrile in 0.1% trifluoroacetic acid. The molar concentrations were calculated using the molar extinction at 230 nm of amino acids (300/residue). The contribution of tyrosine (4980) and tryptophan (6818) to the absorbance at 230 nm were included if necessary (C. Cantor and P. Schimmel, 1980, *Biophysical Chemistry.* W. H. Freeman and Co., New York; G. Fasman, 1976, *CRC Handbook of Biochemistry and Molecular Biology, 3rd Edition.* CRC Press).

C. Analytical Ultracentrifugation

Analytical ultracentrifugation was performed as described in D. Krylov et al., 1994, *EMBO J.,* 13:2849–2861, except that the protein absorbance was monitored at 260 nm. Protein samples at three concentrations were centrifuged at 24,000 rpm until equilibrium and data were collected after 48 hours. The C/EBP sample (MW=16,104), which contains one tyrosine, absorbed at a wavelength of 260 nm, while 3heptad-F (MW=9,847), which does not contain any aromatic amino acids, does not absorb at 260 nm. This absorption difference allowed the monitoring of the oligomerization state of C/EBP in the presence or absence of 3heptad-F.

D. Circular Dichroism (CD)

CD analyses were performed as described in Materials and Methods of D. Krylov et al., 1994, *EMBO J.,* 13:2849–2861. $T_m$ values were calculated as described in D, Krylov et al., 1994, *Ibid,* converted to $K_{d(25)}$ and $\Delta G(25)$ using a $\Delta C_p$ of –0.96 kcal/mol ° $C.^{-1}$ calculated from a $T_m$ versus $\Delta H$ plot for all of the proteins as described herein. All thermal melts were reversible. Table 2 shows the stability of the mixtures of heterodimerizing zipper (F) with C/EBP under different salt conditions.

TABLE 1

| Protein | Homodimer $T_m(\Delta G)k_d$ | with C/EBP $T_m(\Delta G)k_d$ |
|---|---|---|
| C/EBP (L) | 45.8(–10.3)3e-8 | |
| C/EBP-F (L) | | 52.2(–11.1)8e-9 |
| C/EBP (H) | 49.5(–10.9)1e-8 | |
| C/EBP-F (H) | 28(–7.7)2e-6 | 53.6(–11.2)7e-9 |
| 0heptad-F (H) | 30.0(–8.0)2e-6 | 55.4(–11.8)3e-9 |

Table 1 presents the melting temperature ($T_m$, ° C.), $\Delta G$ and $k_d$ at 25° C. for CD thermal melts of a variety of proteins either as homodimers or an equimolar mixture of two proteins. If the mixture had a higher melting temperature than either homodimer alone, it was inferred that the mixture sample was composed of heterodimers. The (L) denotes 'low' salt conditions (50 mM KCl, 25 mM Tris pH 8.0, 0.5 mM EDTA, 1 mM DTT) and the (H) denotes regular salt conditions (12.5 mM potassium phosphate, pH 7.4, 150 mM KCl, 0.25 mM EDTA, and 0.5 mM DTT). The latter conditions were used in Table 2. "0heptad-F" represents the F zipper with the basic region deleted. The RMS error in $\Delta G$ is 0.2 kcal/mol and 0.5 kcal/mol for homo- and heterodimers respectively.

E. Tryptophan Fluorescence

Fluorescence of a tryptophan in the VBP-C/EBP basic region was monitored using an Aminco SLM8000 photon counting spectrofluorimeter in slow kinetics mode 25° C., with excitation and emission at 296 and 342 nm, respectively. Samples contained the same salt conditions used as described for the CD measurements. Samples containing $10^{-6}$ M VBP:C/EBP monomer were mixed with a DNA probe, 28 base pairs in length and containing the C/EBP binding site ($0.5 \times 10^{-6}$ M of duplex), to which a sequence the VBP basic region binds specifically (N. B. Haas et al., 1995, *Mol. Cell. Biol.,* 15:1923–1932). Haas, et al. 1995) The sequence of the probe is 5' GTCAGTCAG <u>ATTGCGCAAT</u>ATCGGTCAG 3' (SEQ ID NO:46). The consensus C/EBP DNA binding site is shown underlined and in bold.

The $K_d$'s of homo- and heterodimers calculated from the CD thermal melts provided a determination of the fraction of VBP-C/EBP displaced from DNA when the DN was added in the fluorescence equilibrium experiments. For example, the VBP-C/EBP DNA binding constant was calculated by determining how effective the DN was at displacing VBP-C/EBP from DNA using the following equation:

$$[DNA_{bound}]/[DNA_{free}] = (K_{hetero}/K_{DNA})^2 [Heterodimer]^2 / \{K_{DN}[DN]\},$$

wherein $K_{hetero}$ is the heterodimer dissociation constant, $K_{DN}$ is the DN dissociation constant, both measured from CD thermal melts, and $K_{DNA}$ is the DNA binding constant of a transcription factor.

The VBP-C/EBP DNA binding constant was calculated as $10^{-10}$ when data for 0heptad-F in 11 molar excess is used, or 1heptad-F, 2-heptad-F or 3heptad-F in 1.1 molar excess is used. The consistency of the calculated DNA binding constants suggests that the ΔG's for the heterodimers as determined by CD thermal melts are valuable indicators of efficacy.

F. Transient transfections

The C/EBP family of transactivator plasmids (pMEX-C/EBPα, pMEX-C/EBPβ, pMEX-C/EBPδ) containing the MSV promoter used herein were as described by S. Williams et al., 1991, *Genes and Devel.*, 5:1553–1567. These plasmids were modified to include a FLAG epitope (Invitrogen) at the N-terminus. The C/EBPα-GCN4 chimeras contained the leucine zipper from the bZIP protein GCN4. The CAT reporter plasmid contained a consensus C/EBP binding site (i.e., ATTGCGCAAT, SEQ ID NO:47) in front of the minimal promoter. All the DNs were cloned into pRc/CMV (Invitrogen) modified to contain the N-terminal FLAG epitope with a nuclear localization sequence (MDYKDDDDK-KKRK, SEQ ID NO:48). C/EBPα was also cloned into pRc/CMV and gave results similar to those obtained using pMEX-C/EBPα for both the transactivation and inhibition assays. Similar results were obtained for plasmids modified with the FLAG epitope and without the FLAG epitope.

In these experiments, 10 μg of reporter plasmid, 0.3 μg of transactivator, and 5 μg of DN were added to each transient transfection. 3heptad-F with the DPD cap totally inhibited C/EBP transactivation in a 1:1 molar ratio. Sheared salmon sperm DNA was added to bring the DNA concentrations to 20 μg. Calcium phosphate transfections were performed following the manufacturer's instructions (Gibco).

Western blotting of cellular extracts of generated from the transient transfections indicated that 3heptad-F containing a FLAG epitope placed 5' or N-terminal of the acidic extension was not seen on the blot, even though the construct completely inhibited C/EBP transactivation. A possible explanation was that the three glycine N-terminal cap used to stop the acidic extension was a proteolysis-sensitive protein sequence. Consequently, four additional sequences were employed as N-terminal caps, namely, DP-, DP-D, DP-EE, and DP-DEEE, replacing DP-GGG), (J. Richardson and D. Richardson, 1988, *Science*, 240:1648–1652). Their thermal stability as heterodimers with C/EBP was monitored, and their ability to be detected using a Western blot of cell extracts obtained from the transient transfections was determined. All of the sequences were detected in Western blots. Interestingly, the DP- and DP-D caps were three-fold more stable than the DP-GGG cap.

It was found by the present inventors that transactivation of the bZIP protein C/EBP was not totally inhibited either by the heterodimerizing F zipper (i.e., 0heptad-F) or by a three heptad acidic extension appended onto the C/EBP leucine zipper (i.e., 3heptad-C/EBP). Notwithstanding, the 3heptad-C/EBP did inhibit to a measurable degree. Changes in both the leucine zipper and the acidic extension generated a protein (3heptad-F) that formed a sufficiently stable heterodimer with C/EBP to inhibit competitively both C/EBP DNA binding and transactivation. However, it will be appreciated that for other proteins in the bZIP family and in other structurally similar families of proteins, the acidic extension alone may contribute enough stabilizing energy to create a dominant negative without the additional stability conferred by the heterodimerizing zipper. This will depend on the relative stabilizing effect of the DNA binding for particular bZIP proteins. Based on the present invention, acidic extensions can be designed that dimerize even more strongly with the basic region, thus allowing the creation of a dominant negative to any bZIP protein by simply appending an acidic extension onto the N-terminus of any bZIP leucine zipper.

Example 2
Acidic Extensions Increase Heterodimerization of the bZIP Class of Proteins Experiments were conducted to determine the effect of acidic extensions on DNA binding proteins of the bZIP class, c-Fos, CREB, and CEBP. c-Fos and CREB proteins were designed to contain an acidic 4 heptad repeat (FIGS. 3 and 4). An acidicaUy extended CREB was designed to contain a new acidic extension (New4hepCREB) in which the asparagine was changed to a leucine as described in FIG. 3. As shown, CREB+New4heptadCREB had a melting temperature of 69.5° C. (open circles). This dramatic increase in thermal stability relative to the asparagine-containing acidic extension suggests that different classes of acidic extensions can be used to append to the N-terminal dimerization domain of bZIP proteins, depending on the exact bZIP protein to be inactivated.

In FIG. 4, an engineered c-Fos protein having the basic region deleted, called 0heptad-Fos, increased the melting temperature of the Fos/Jun complex to 53° C. (open squares). An engineered c-Fos protein having the basic region replaced with an acidic region (containing four acidic repeats, called "4heptadFos") increased the melting temperature of the Fos/Jun complex to 61° C. (open circles). An engineered c-Fos protein in which one amino acid in the acidic region was changed from an asparagine to a leucine, as described for FIG. 2, called new4heptadFos, resulted in a higher melting temperature of 72° C., and more stable heterodimerization with c-Jun (closed squares). Also as shown in FIG. 4, homodimerization of unmodified c-Jun had a melting temperature of 29.4° C., and homodimerization of acidically modified c-Fos (having four acidic repeats appended at the amino terminus of the c-Fos protein) had a melting temperature of 25° C. Also in FIG. 4, the Kd(37° C.) for the c-Jun homodimer was 20 μM; 0.2 μM for the c-Jun/c-Fos heterodimer; and 6 nM for the c-Jun/4heptadFos heterodimer.

Example 3
Specificity of a bZIP and the Acidic Extension is Determined by the Zipper The specificity of the basic region of a bZIP protein and the acidic extension on the N-terminus of a leucine zipper (i.e., called aZIP) was found to be determined by the leucine zipper. As shown in FIG. 5A, mixing a bZIP CEBP protein and an aZIP 4heptadFos protein with incompatible zippers produces no interaction, i.e., 4heptadFos does not interact with CEBP. FIG. 5B shows that mixing a bZIP VBP protein and an aZIP 3heptadF-(CEBP specific) protein also produces no heterodimeric interaction. In FIGS. 5A and 5B, the solid lines is the simple sum of the two homodimer curves. The fact that the actual mixture gives identical results demonstrates that no heterodimers are formed.

Example 4
Transactivation by an AP1 Cis Element is Inhibited by Acidic Extension Appended onto a DNA Binding Protein AP1 activity was demonstrated to be inhibited by several acidic extensions appended onto the bZIP DNA binding protein c-Fos in transient transfection experiments using human hepatoma cells (HepG2) and AP1-dependent CAT reporter expression constructs and measuring CAT activity (FIG. 6). HepG2 cells were transfected with up to three plasmid constructs for the expression of c-Fos proteins. The three plasmids were: a construct for expression of the Jun transactivator, a reporter construct containing an AP1 cis element driving CAT expression, and a construct containing DNA encoding the dominant negative and appropriate expression and regulatory sequences. CMV566 AND CMV500 are plasmids containing the cytomegalovirus promoter driving the expression of DNA binding proteins that contain at their N-termini, either the Hemagglutinin (YPYDVPDYA) (SEQ ID NO:49) or the FLAG (DYKDDDDK) (SEQ ID NO:50) epitopes, respectively. c-Fos proteins were designed to contain no acidic heptad repeats appended N-terminally from the basic region (0hep-Fos), one acidic heptad repeat appended N-terminally from the basic region (1hep-Fos), two acidic heptad repeats appended N-terminally from the basic region (2hep-Fos), three acidic heptad repeats appended N-terminally from the basic region (3hep-Fos), or four acidic heptad repeats appended N-terminally from the basic region (4hep-Fos). Transfections were carried out using either 3 or 15 μg of plasmid containing CMV566 or CMV500 and DNA sequence encoding bZIP having N-terminal extensions as shown in FIG. 6. The results of these experiments show that AP1 transactivation by expressed c-Jun protein is inhibited by expressed c-Fos protein having appended acidic extensions. The results also demonstrate that the inhibition of AP1 transactivation is specific, since acidic extensions appended onto other bZIP proteins (i.e., CREB, VBP, or Jun) did not inhibit AP1 transactivation.

Figure 8:
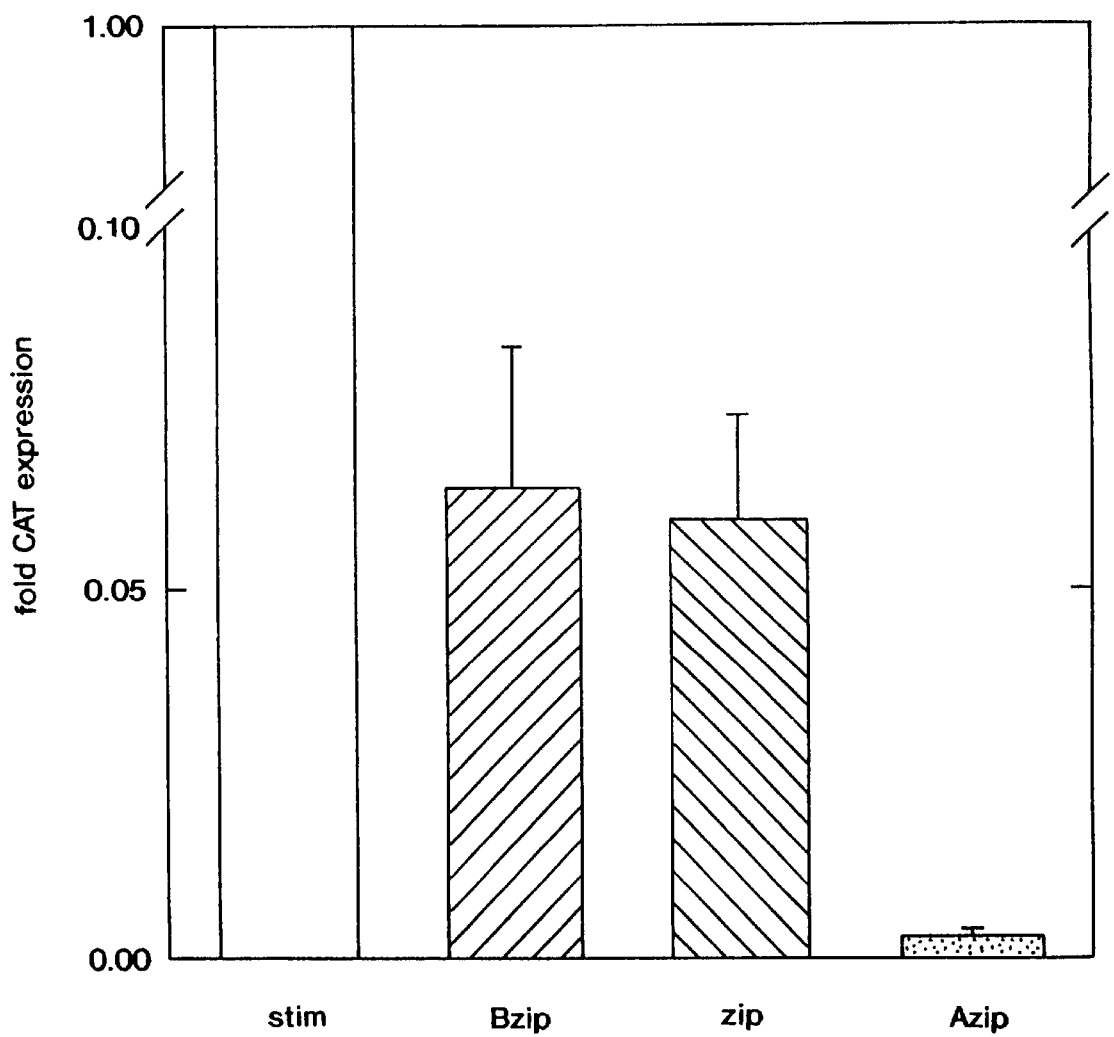
FIG. 8 represents the Jurkat cell system as described in FIG. 7, with the addition that the leucine zipper ("zip") construct alone is also transfected into cells. Jurkat cells were transfected with two plasmids and stimulated with TPA. The efficacy of three potential dominant negatives containing the Fos leucine zipper (i.e., Bzip, zip, and Azip) were compared. These three dominant negatives are the Fos Bzip domain without a transactivation domain (Bzip), the Fos leucine zipper with no basic region (zip), and the Fos leucine zipper containing the 4heptad acidic extension (Azip). The data show that expressed aFos inhibits AP1 transactivation significantly better than does an expressed Fos zipper protein or an expressed bFos protein in the Jurkat cell system.

Example 5
A bZIP Protein Containing an Acidic Extension (aZIP) is a Better Inhibitor of AP1 Activation Than a bZIP Protein Containing no Acidic Extension Experiments similar to those described in Example 4 were performed in an additional transient cell system using Jurkat cells extension (bFos). Jurkat cells (a B cell model) have a high level of endogenous Fos/Jun (AP1) activity. Cells were transiently transfected with two plasmids (1 μg each), namely, a reporter construct containing AP1 cis elements and a construct containing the CMV500 promoter driving the expression of either a truncated form of Fos (bZipFos) or the Fos leucine zipper containing the 4heptad acidic extension (aFos). AP1 activity was induced by the addition of 12-O-tetradecanoylphorbol(TPA) which resulted in a 40-fold induction of the gene. The transactivation of the reporter gene occurred because of endogenous activity. As demonstrated in FIGS. 7 and 8, expression of the bZipFos protein encoded by a bZipFos DNA sequence construct resulted in dominant negative activity; however, expression of aZipFos protein encoded by an aZipFos construct was more efficacious and showed a significantly high level of inhibition of AP1 activity. In these experiments, the aZIP protein c-Fos was designed to contain 4 acidic heptad repeats appended N-terminally (4heptad-Fos). The inhibitory activity of the expressed aZIP protein was compared with that of a c-Fos protein that was not engineered to contain an acidic extension (bZIP).

Example 6
Acidic Extensions Appended to DNA Binding Proteins Provide Compounds for the Control and Regulation of Gene Function An acidic extension was appended onto the dimerization domain of a DNA binding protein of the bHLH class (FIG. 9). Replacing the basic region of an expressed bHLH protein Max having an amphipathic acidic extension (i.e., 2heptadMax) increased heterodimerization of Max with c-Myc, irrespective of the orientation of the acidic extension as appended to the HLH protein. The 2heptadMax proteins used in the heterodimerization studies shown in FIG. 9 are expressed Max proteins having amphipathic acidic extensions as follows:

DPDLEKEAEELEQENAELELEDSF, called 2heptadMax (783), (SEQ ID NO:1);
DPDLEKEAEELEQENAELEELEDSF, called 2heptadMax (784), (SEQ ID NO:2); and
DPDLEKEAEELEQENAELEELEDSF, called 2heptadMax (785), (SEQ ID NO:3).

AcidMax is an expressed Max protein having appended N-terminally an acidic extension as follows: DPDEEED-DEEELEELEDSF (SEQ ID NO:4). 0heptadMax is an expressed Max protein having the sequence DPDLEELEDSF (SEQ ID NO:5) as its acidic extension. 0heptadMax is the dimerization domain of Max without an acidic extension. Because of gene cloning, this protein as expressed has the short acidic extension DPDLEELEDSF (SEQ ID NO:5). The increase in the dimerization with c-Myc by the addition of the acidic extension on Max shows the utility of the approach of the invention.

In addition, the expressed AcidMax protein having a polyglutamic acid sequence heterodimerized with c-Myc better than did Max protein containing any of the three amphipathic extensions. In FIG. 9, the Kd(M) for the acidically modified and unmodified HLH proteins is as follows:

|  | Homodimer Kd (M) | Heterodimer with c-Myc Kd (M) |
| --- | --- | --- |
| bHLH MAX | $6 \times 10^{-6}$ | $3 \times 10^{-8}$ |
| 0heptadMax | $1 \times 10^{-7}$ | $6 \times 10^{-10}$ |
| 2heptadMax | $4 \times 10^{-8}$ | $6 \times 10^{-12}$ |
| AcidMax | $3 \times 10^{-8}$ | $2 \times 10^{-12}$ |

In the plasmid vectors designed to carry the Max DNA sequence, the "DPD" amino acid sequence is a Bam cloning site. Immediately N-terminal of the BamHI cloning site DPD, the protein constructs contain a 13 amino acid sequence that is from the Φ10 phage (ASMTGGQQMGR) (SEQ ID NO:51). The eukaryotic expression vectors can contain an additional N-terminal protein sequence 5' of the Φ10 protein sequence. This additional N-terminal protein sequence is an epitope used to monitor expression in mammalian cells. Its sequence is YPYDVPDYA (SEQ ID NO:49).

The last amino acid of the Max extensions is a phenylalanine (F) in 1 of the dimerization domain of Max. This amino acid is conserved in most bHLH proteins, thus providing a convenient landmark in the Max protein structure from which to know where the designed acidic sequences were appended onto the dimerization domain of Max. In the experiments described in this Example, an amphipathic acidic protein sequence was added onto the N-terminus of the Max dimerization domain. The linker between the acidic extension and the dimerization domain contained different numbers of glutamic acids. This difference in the length of the linker had the effect of rotating the acidic amphipathic sequence relative to the dimerization domain.

These results demonstrate the universal nature of the acidic extension for allowing a DNA binding protein from different classes ultimately to control and regulate gene function.

Example 7
Effects on Cell Growth and Transformation Following Stable Transfection of Cells with Constructs Harboring DNA Binding Proteins Containing Appended Acidic Extensions Cell transfection assays were performed in which cells (e.g., C3H10T1/2) were plated and transfected with 50 ng DNA per plate. The foci assay used in these experiments was as described by S. Min et al., 1993, *Oncogene*, 8:2691–2701. Two experiments with the potential DNs were conducted. First, cells were transformed with the constructs as described and were plated in conventional tissue culture plastic dishes (e.g., Petri dishes). These assays examined the effects that the constructs containing DNA encoding acidically extended DNs had on cell viability. It was found that cell viability was not affected by the constructs. Next, the same cells were transfected with constructs harboring Max DN DNA (described in Example 6) in conjunction with plasmids harboring Ras and/or Myc-encoding DNA, and the ability of the cells to grow in a contact-inhibited independent fashion was examined. The cells were plated in plastic dishes at high concentrations and their ability to overcome contact inhibited growth was evaluated. When the Max DNs of the invention (e.g., acidicauy extended Max) were co-transfected with Ras (10 ng) and/or Myc (300 ng), the action of the DN was clearly observed. OheptadMax (1 µg) inhibited foci formation from 73 colonies to 34 colonies, while 2heptadMax decreased the number of colonies down to zero. A polyacidic Max construct is likely to inhibit foci formation in these assays as well as, or better than, the inhibition activity of 2heptadMax. The ras construct used in the experiments contains a ras gene which contains a mutation which keeps it constitutively active as described in E. Taparowsky et al, 1982, *Nature*, 300:762–765. The ras gene is driven by its normal promoter. The myc construct is a regular myc gene driven by the RSV LTR. After 3 days, plates were fixed and were stained after 14 days. Also, after 14 days, G418 resistant colonies were quantified and the results are shown below.

| Plasmid Construct | Total Number Of Colonies | Number of Foci Per Plate |
|---|---|---|
| pCMV 566 | 509 | 127 |
| pCMV 566 Max | 549 | 137 |
| 0heptad Max | 510 | 128 |
| 2heptad783 Max | 336 | 92 |
| 2heptad784 Max | 524 | 131 |
| 2heptad785 Max | 517 | 129 |
| Ras | | 22 |
| Ras + Myc | | 73 |
| Ras + Myc + pCMV566Max | | 52 |
| Ras + Myc + 0heptadMax | | 34 |
| Ras + Myc + 2heptad784Max | | 0 |

As shown below, the same types of experiments performed using the Fos constructs of the invention showed an inhibition of foci formation. In contrast to Max, the Fos expression constructs were able to inhibit both colony formation and foci formation in these assays. In the colony assay, results are also shown for a control plasmid construct (designated pKOneo) carrying only the neomycin gene for the selection of cells carrying this gene and expressing its product; the control plasmid resulted in 127 colonies. As known by those in the art, the neo gene is a conventional marker gene, built into constructs containing other expressible genes and used as a selection marker for expression of the neo gene as determined by resistance of the cells to neomycin following transformation or transfection of cells with a plasmid construct as described.

| Plasmid Construct | |
|---|---|
| Focus Assay: | Relative Focus Formation |
| Ras (200 ng) | 1 |
| Ras (200 ng) + 0heptad-Fos (600 ng) | 0.38 |
| Ras (200 ng) + 4heptad-Fos (600 ng) | 0.29 |
| Colony Assay: | Colonies Per Plate |
| pKONeo (200 ng) | 127 |
| 0heptad-Fos (200 ng) | 121 |
| 4heptad-Fos (200 ng) | 87 |
| Ras (200 ng) + 0heptad-Fos (600 ng) | 61 |
| Ras (200 ng) + 4heptad-Fos (600 ng) | 49 |

Example 8
Competition Assays

Three types of competition experiments demonstrated that the acidic extension created a robust DN to the bZIP protein C/EBP's activity. Two biochemical assays addressed DNA binding (i.e., gel shift and fluorescence assays) and one biological assay addressed transactivation function (i.e., transient transfection assay).

A. Gel Shifts

Gel shift experiments were undertaken to examine if 3heptad-F inhibited the binding of C/EBP to its cognate DNA sequence. Gel shift data indicated that C/EBP bound to DNA with a $K_d = 10^{-9}$ M (Z. Cao et al., 1991, *Genes Dev.*, 5:1538–1552). The CD experiments presented herein indicated that 3heptad-F heterodimerized with C/EBP with $K_d = 4 \times 10^{-11}$ M. Therefore, an equimolar mixture of DNA, C/EBP dimers and 3heptad-F dimers was expected to prevent C/EBP from binding DNA, because of the formation of the C/EBP:3heptad-F heterodimer. The gel shift data confirmed that this equimolar mixture completely inhibited C/EBP binding to a consensus radiolabeled oligonucleotide (FIG. 13A).

B. Fluorescence

The second competition assay monitored the intrinsic fluorescence of the only tryptophan found in the basic region of VBP. DNA binding of the VBP-C/EBP chimera increased the fluorescence of this tryptophan by approximately 40%. The increase in fluorescence is to be expected if the tryptophan is in a more constrained environment, a situation which is expected upon DNA binding (Cantor and Schimmel, 1980, *Biophysical Chemistry*. W. H. Freeman and Co., New York), (FIG. 13B). This change in the intrinsic fluorescence of VBP-C/EBP upon DNA binding allowed the examination of the kinetic and equilibrium consequences of adding the F zipper-acidic extension series to this bZIP DNA complex. It was found that VBP-C/EBP bound to DNA with a fast on-rate (~5 seconds), and that the addition of the F zipper-acidic extension proteins resulted in a decrease in tryptophan fluorescence. This is expected if the F zipper-acidic extension proteins heterodimerized with VBP-C/EBP, thus preventing DNA binding.

Proteins containing different length acidic extensions appended to the F zipper were mixed with the VBP-C/EBP DNA complex in a 1 to 1.1 molar ratio. The longer acidic extensions caused a greater decrease in the fluorescence, thus indicating more effective heterodimerization with VBP-C/EBP. Ten additional molar equivalents of DN were added after the reaction came to equilibrium in about 20 minutes. 0heptad-F and 1heptad-F were not able to totally displace VBP-C/EBP from DNA, even in 11-fold excess. However, at an 11-fold molar excess, 2heptad-F and 3heptad-F were able to totally displace VBP-C/EBP from DNA. 4heptad-F was the most potent, as 1.1 molar equivalents displaced 85% of VBP-C/EBP from its binding to DNA.

The location of the tryptophan residue in the VBP basic region is four heptads from the leucine zipper. The tryptophan would be expected to be in a random coil conformation as a heterodimer with the shorter acidic extensions, such as those having one, two, or three heptad extensions (i.e., 0–3heptad-F), but would be expected to be in a coiled coil conformation as a heterodimer with more acidic extensions (i.e., 4heptad-F). The tryptophan would be expected to be part of the hydrophobic interface, i.e., it would occupy the a position, and, consequently, might have a greater fluorescence. This was observed. The tryptophan fluorescence of VBP-C/EBP in mixtures with 0, 1, 2, and 3heptad-F is similar to that of VBP-C/EBP alone which we interpret as the tryptophan fluorescence in the random coil state. In the mixture with 4-heptad-F, the fluorescence of VBP-C/EBP increases by about 10% suggesting that the tryptophan is more constrained as would happen if it is in the hydrophobic interface of a coiled coil C. Transient Transfections The third competition assay involved the transient transfection of constructs harboring the acidic extension and bZIP DNA sequences into a hepatoma cell line (HepG2) to monitor the transactivation properties of C/EBP on a promoter containing a single C/EBP binding site (see also Example 1F). C/EBP was shown to be able to transactivate this promoter 10-fold (FIG. 14). Constructs containing four, different, potential DNs were also able to inhibit C/EBP transactivation in a 15 to 1 ratio. These four DNs are a truncation of the transactivation domain (ΔC/EBP), 0heptad-F, 3heptad-F, and 3heptad-C/EBP. Constructs carrying ΔC/EBP, 0heptad-F, and 3heptad-C/EBP inhibited C/EBP transactivation only slightly. In marked contrast, 3heptad-F was able to inhibit completely C/EBP-mediated transactivation. This total inhibition was also observed at a ratio of C/EBP plasmid to 3heptad-F plasmid of 1 to 1. Thus, both the heterodimerizing F zipper and the acidic extension were discovered to be essential for total inactivation of C/EBP. In addition, the 3heptad-F-containing construct was found to inhibit the transactivation activity of all the C/EBP family members examined (C/EBPα, C/EBPβ, C/EBPδ).

To investigate if 3heptad-F inhibition of C/EBP transactivation was dependent on the C/EBP leucine zipper, C/EBP transactivating proteins were generated in which the C/EBP leucine zipper was replaced with the GCN4 leucine zipper. This chimeric protein was able to transactivate a minimal promoter in a C/EBP cis element-dependent manner. This transactivation was not inhibited by 3heptad-F, thus indicating that the DN properties of 3heptad-F are dependent on specific leucine zipper interactions.

Example 9
The Acidic Extension Forms a Coiled Coil with the Basic Region of Leucine Zipper Containing Proteins, e.g., bZIP It was found that the addition of one or more heptads of acidic amino acid sequences onto the N-terminus of the leucine zipper stabilized heterodimer formation, as determined by circular dichroism (CD) spectra and thermal melting assays as described herein. This acidic protein (or polypeptide or peptide) extension formed a heterodimeric coiled coil with the basic region of the wild type or native protein containing the leucine zipper and allowed the creation of a dominant negative to the native protein that stoichiometrically displaced the native protein from DNA and inhibited transactivation by the native protein.

Sedimentation equilibrium analysis was carried out in order to determine the oligomerization state of an equimolar mixture of C/EBP and 3heptad-F (FIG. 11). The data were fitted to a single molecular species. The calculated molecular weight for C/EBP is 33,000 Daltons (dimer MW is about 32,208) and for the C/EBP—3heptad-F mixture is 28,000 (heterodimer MW is about 26,200). These data are consistent with C/EBP forming a heterodimer when mixed with 3heptad-F.

Circular dichroism (CD) was used to determine the amount of α-present in mixtures of C/EBP and different length acidic extensions appended to the F zipper (FIG. 12A) The mixtures of C/EBP with progressively longer acidic extensions showed a progressive increase in α-content. The increase in α-helical content of the heterodimerizing mixtures as described herein reveals that the leucine zipper dimerization interface is extending into the basic region: the longer the acidic extension, the farther the coiled coil structure extends from the leucine zipper into the basic region. The CD spectra of the acidic extensions series (0heptad-F to 3-heptad-F) as homodimers at 6° C. displayed a similar amount of α-helical content, thus indicating that the progressively longer acidic extensions were not helical. The CD melt of 4heptad-F was biphasic; this is believed to indicate that the acidic extension forms a coiled coil which melts at 13° C., independently of the leucine zipper.

The stability of the mixtures of C/EBP and the different length acidic extensions was determined by CD thermal melts (Table 2 and FIG. 12B). All mixtures had a higher $T_m$ than the individual homodimers, thereby suggesting that heterodimers were formed. The 0heptad-F:C/EBP heterodimer was more stable than the C/EBP homodimer, but the former did not contain any additional helical content. This suggests more stability for the leucine zipper structure. The progressively longer acidic extensions created progressively more stable complexes. These extensions raised the $T_m$ about 10° C., which corresponded to 2.5 kcal/mol or over 100 fold stabilization.

The energetic and structural consequences of adding up to four heptads of acidic protein sequence onto the N-terminus of the F leucine zipper was assayed by circular dichroism (CD) spectra and thermal melts. The first acidic heptad appended to the F zipper stabilized the heterodimer with C/EBP by over 1 kcal/mol. This increase in stability was accompanied by an increase in ellipticity, indicative of α-formation. Each additional acidic heptad extension produced an increase in ellipticity consistent with extending the leucine zipper coiled coil by one heptad. However, the contribution to stability became successively less with increased heptad extensions. The combination of the increase in ellipticity and the progressive decrease in the contributed stability suggests that the coiled coil structure between the C/EBP basic region and the acidic extensions is weaker as the structure extends further from the leucine zipper. Similar results were obtained if the C/EBP basic region was replaced with other basic regions, e.g., the VBP or GBF basic regions. On the basis of these findings, extensions can be designed and created to dimerize specifically with a subset of basic regions in bZIP proteins and structurally similar proteins.

Example 10
Stability of the Heterodimerizing Zipper (F) with C/EBP

The thermal stability of the heterodimers formed between C/EBP and the F leucine zipper produced as described by C. Vinson et al., 1993, *Ibid.*, either as a chimera with the C/EBP basic region (C/EBP-F) or alone (0heptad-F), was determined (see Table 1 and FIGS. 9C–9D). Using gel shift conditions (50 mM KCl), a chimera containing the F zipper and the C/EBP basic region (C/EBP-F) formed a heterodimer with C/EBP that was five times more stable than the C/EBP homodimer. However, using more physiological salt conditions (150 mM KCl), C/EBP-F formed a heterodimer with C/EBP that was only twice as stable as the C/EBP homodimer. Deletion of the basic region (0heptad-F) increased the stability of the heterodimer with C/EBP by 0.5 kcal/mol, but the heterodimer was still not as stable as the wild type C/EBP homodimer bound to DNA. These results showed that initial attempts to create a DN that could displace C/EBP from DNA by making modifications only in the leucine zipper were unsuccessful.

The wild type C/EBP homodimer was less stable by 4° C. in 50 mM KCl compared with 150 mM KCl, presumably because of repulsion between the basic regions. This decrease was not observed for a C/EBP:C/EBP-F heterodimer, because the increase in the electrostatic attraction between the F zipper and the wild type C/EBP zipper apparently compensated for the increased repulsion between the two C/EBP basic regions. Similarly, the increased stability of the C/EBP:0heptad-F heterodimer relative to that of the C/EBP:C/EBP-F heterodimer may have been due to the same interactions, because the 0heptad-F mutant lacked the repulsive basic region.

Example 11
The Acidic Extension Forms a Coiled Coil with Two Additional bZIP Basic Regions To investigate if the acidic N-terminal extension formed a coiled coil with other bZIP basic regions, chimeras were generated containing two additional basic regions attached to the native C/EBP leucine zipper. The first basic region was derived from the chicken vitellogenin gene-binding protein (VBP) (S. Iyer et al., 1991, *Mol. Cell. Biol.*, 11:4863–4875), the chicken equivalent of TEF (D. Drolet et al., 1991, *Genes Dev.*, 5:1739–1753), and the second was derived from GBF-1, a plant bZIP protein known to bind to the most divergent cis element of the bZIP proteins (U. Schindler et al., 1992, *EMBO J.*, 11:1261–1273). The results of thermal melts of these chimeras (i.e., VBP-C/EBP and GBF-C/EBP) as homodimers showed a $T_m$ within 1° C. of C/EBP, indicating that dimerization strength was determined by the leucine zipper (Table 2). Table 2 presents the stability of heterodimers between the F zipper with different length acidic extensions and chimeras containing three different bZIP basic regions appended to the C/EBP zipper.

As shown, four acidic heptad extensions were able to interact favorably with the three different bZIP basic regions that were examined. Initially, this was found to be surprising since it was assumed that the C/EBP basic region would be a better candidate for forming a coiled coil with the acidic extension than the GBF and VBP basic regions. Most bZIP proteins, including GBF and VBP, contain a basic amino acid in the first d position N-terminal of the leucine zipper, while C/EBP contains an alanine. It was expected that the basic amino acids would disfavor coiled coil formation while the alanine would be more favorable. CD thermal melts indicated that this was true; C/EBP heterodimerized with 1heptad-F 1.7±0.5 kcal/mol better than with 0heptad-F, while the VBP and GBF basic regions were only stabilized 0.9±0.5 and 1.3±0.5 kcal/mol, respectively. Interestingly, this difference in stability among the three basic region became less pronounced as the basic region was "zippered" up by longer acidic extensions.

The acidic extension to the leucine zipper domain was successfully stabilized by a variety of different basic regions, thus suggesting that this protein sequence can be used to create dominant negatives for a variety of different types of proteins comprised of basic domains and leucine zipper domains. The biological assays exemplified herein demonstrate that C/EBP transcription factor proteins designed and produced to contain the acidic extension are robust dominant negatives of the C/EBP family, which is considered to be representative of other protein members in the bZIP family or in structurally similar protein families.

TABLE 2

| Dominant negative (DN) | Homodimer $T_m(\Delta G)k_d$ | bZIP protein | | |
|---|---|---|---|---|
| | | C/EBP-C/EBP $T_m(\Delta G)k_d$ | VBP-C/EBP $T_m(\Delta G)k_d$ | GBF-C/EBP $T_m(\Delta G)k_d$ |
| | | Homodimer | | |
| | | 49.5 (−10.9)1e-8 | 50.0(−11.1)8e-9 | 50.2(−10.6)2e-8 |
| | | Heterodimer with | | |
| 0heptad-F | 30.0(−8.0)1e-6 | 55.4(−11.8)3e-9 | 55.1(−12.2)1e-9 | 55.7(−11.9)2e-9 |
| 1heptad-F | 29.0(−8.0)1e-6 | 60.8(−13.5)1e-10 | 60.5(−13.1)3e-10 | 62.0(−13.2)2e-10 |
| 2heptad-F | 24.8(−7.4)4e-6 | 63.6(−13.9)7e-11 | 62.8(−13.8)9e-11 | 63.1(−13.6)1e-10 |
| 3heptad-F | 28.3(−7.9)2e-6 | 63.8(−14.3)4e-11 | 64.2(−14.7)2e-11 | 64.0(−14.2)4e-11 |
| 4heptad-F | 15.2(−6.3)2e-5 | 64.8(−14.2)4e-11 | 65.2(−14.8)1e-11 | 65.0(−14.5)3e-11 |
| 3heptad-C/EBP | | 61.0(−12.6)6e-10 | | |

The two chimeras were mixed with the four different length acidic extensions appended to the F zipper and their stability was determined from CD thermal melts. Interestingly, the two additional basic regions were also stabilized by the acidic extensions. The degree of stabilization was the same for the three basic regions examined, thus suggesting that the interaction occurred with the more conserved part of the basic region.

Thus, two lines of evidence suggested that the acidic extension formed a coiled coil with the basic region in the proteins expressed and assayed in accordance with the invention. The first was that in α-helical content increased when the acid extensions were mixed with the basic regions to form chimeric structures. The second was determined from the fluorescence analysis of exemplary heterodimers formed between chimeras of the VBP and C/EBP bZIP proteins and the F zipper-acidic extension series (See Examples 1E and 8B). The tryptophan in the VBP-C/EBP chimera is located in the basic region, four heptads from the leucine zipper. If a coiled coil were formed between the basic region of VBP and the acidic extension, then only the heterodimer between the 4heptad-F and VBP-C/EBP would be expected to place the tryptophan in the coiled coil structure, thereby causing a new fluorescence signal. Indeed, this result was observed. However, such a change in the fluorescence signal was not observed in heterodimers which contained the shorter acidic extensions.

Example 12
The Acidic Extension is a DNA Mimetic

The importance of different coiled coil positions (a,b,c, d,e,f,g) in the acidic extension to heterodimer stability with native C/EBP was examined by producing four mutant proteins. Each protein comprised a subset of the mutations to the C/EBP basic region that was used to create 3heptad-F. The largest contribution to heterodimer stability was provided by the glutamic acids placed in the e and g positions. These negatively charged amino acids presumably interact with the positively charged amino acids found in abundance in the basic region, thus suggesting that the acidic extension acts as a DNA mimetic by matching the electrostatic properties of DNA. The three additional mutant proteins demonstrated the contributions of the N-terminal helical cap consisting of three glycines, the cap plus the hydrophobic core (a and d), and the cap plus general electrostatic and forming concerns (b, and c). All of the mutant proteins contributed some stability to the heterodimer with the wild type C/EBP basic region (see Example 1F).

Example 13
Transgenic Mouse Studies

Transgenic animals, and in particular mice, are created using the constructs described for the transient transfection assays in Examples 1F and 8C. Briefly, the constructs are introduced into an animal or an ancestor of the animal at an embryonic stage, i.e., the one-cell stage, or generally not later than about the eight-cell stage. Transgenic animals carrying the constructs of the invention can be made by several methods known to those having skill in the art. One method involves transfecting a retrovirus constructed to contain the DNA sequence encoding a dominant negative leucine-zipper containing protein to provide a complete shuttle vector harboring the dominant negative nucleic acid sequence as a transgene. Another method involves directly injecting a transgene into the embryo. A third method involves the use of embryonic stem cells. Examples of animals into which the transgenes or constructs may be introduced include, but are not limited to, mice, rats, other rodents, sheep, pigs, and primates (see "The Introduction of Foreign Genes into Mice" and the cited references therein, In: *Recombinant DNA*, Eds. J. D. Watson et al., W. H. Freeman and Company, New York, N.Y., pp. 254–272). Transgenic animals carrying and stably expressing transgenes encoding the DNs of the invention can be used as biological models for the study of cancer and tumor regression or atrophy, for example. The appropriate tissues of the transgenic animal can be monitored for the integration of the construct, or components thereof, by assaying for the presence of RNA or DNA in the cells using established methods in the art.

In addition, transgenic mice can be produced in which tissue specific promoters are used in constructs containing DNA sequences encoding acidic extensions to the zipper of bZIP, or structurally similar proteins, as well as other pertinent sequences, to act as dominant negatives to one or more of the three C/EBP isoforms expressed during adipose conversion of 3T3-L1 cells (Z. Cao et al., *Genes Dev.*, 5:1538–1552). The production of functional dominant negatives in this system will allow the inactivation of gene(s), or mutants thereof, involved in the conversion of cells to adipose cells. The constructs as described may provide the potential to reduce or alleviate the conditions of morbid obesity and type II diabetes associated with the syndrome of morbid obesity in model animals and in humans.

Tissue specific promoters such as the whey activating protein (WAP) which targets mammary tissue, can be used to create transgenic animals in which the DN is localized to and functions specifically in breast tissues. For example, a construct can be designed to include the mouse WAP promoter and isolated DNA encoding the DN proteins of the invention, in addition to the appropriate elements for proper transcription of the gene and protein expression in cells. The activity of the DN to inactivate the abnormal activity of cellular proteins can be monitored in mammary tissue of the female transgenic mice.

In addition, the constructs can be used in human gene therapy treatments as known in the art to inactivate cellular protein products the regulation of which is controlled by or linked to transcription regulatory proteins possessing leucine zipper structures. Gene therapy techniques which can be modified as required for use of the constructs of the invention are described, for example, in U.S. Pat. No. 5,399,346 to W. French Anderson et al.

Example 14
Transgenic Mouse Studies using a Dominant Negative C/EBP to Create Phenotypically "Skinny" Mice As set forth in Example 13, transgenic mouse studies were carried out and mouse pups were born which exhibited a transgenic phenotype showing that the dominant negatives produced and expressed in accordance with the invention functioned in an in vivo environment in an animal. The transgenic mice were produced by routine methods practiced in the art of transgenic animal production.

In these studies, transgenic mice were produced by injecting early-stage mouse embryos with the construct described in FIG. 30. As described, this plasmid construct was designed to contain the 422/aP2 promoter (adipose fatty acid-binding protein), DNA sequence encoding the dominant negative 3heptadF C/EBP of the invention, which produces, upon translation and expression, an acidically extended bZIP C/EBP protein, that functions as a dominant negative to the non-mutant C/EBP protein, and other regulatory sequences as described for FIG. 30. C/EBP has been implicated in the development and differentiation of adipose (fat) cells. The dominant negative 3heptadF C/EBP sequence was placed under the control of the 422/aP2 adipocyte-specific promoter, and also contained the FLAGφ10 epitope as described hereinabove.

Four initial founder mice were produced by injecting mouse embryos with the construct capable of expressing the dominant negative C/EBP protein. The founder mice were used to produce offspring carrying one or more copies of the transgene. One of the offspring of a founder mouse showed a thin, skinny phenotype, which would be expected if expression of the dominant negative affected the expression of normal C/EBP protein and resulted in negative regulation and influence of adipose or fat cell and tissue development and differentiation.

More specifically, the male founder transgenic mouse impregnated two female mice. The two litters produced by these two females contained two phenotypically distinct types of pups: the first types were scrawny, small-sized mice with scruffy fur and the second types were normal-sized with normal-looking fur. The small-sized, scrawny and scruffy pups all carried copies of the transgene, while their normal littermates did not. These results indicate that constructs designed to contain DNA encoding acidically extended dominant negatives and expressed as transgenes in animals in vivo can influence, e.g., via inactivation, the expression and/or function of a normal counterpart protein encoded by the normal gene. In addition, such dominant negatives can demonstrably affect the phenotypes of the animals carrying the transgene, which were bred from the transgenic founder animals.

The contents of the patents, articles, texts, and references contained herein are hereby incorporated by reference in their entirety.

Although the foregoing invention has been described in some detail by way of illustration and example for purposes of clarity of understanding, it will be obvious to those skilled in the art that certain changes and modifications may be practiced without departing from the spirit and scope thereof, as described in the specification and as defined in the appended claims.

```
                       SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
         (A) LENGTH: 24 amino acids
         (B) TYPE: amino acid
         (C) STRANDEDNESS: unknown
         (D) TOPOLOGY: linear (ii) MOLECULE TYPE: peptide (xi) SEQUENCE DESCRIPTION: SEQ ID NO:1:

Asp Pro Asp Leu Glu Lys Glu Ala Glu Glu Leu Glu Gln Glu Asn Ala
1               5                  10                  15

Glu Leu Glu Leu Glu Asp Ser Phe
            20

(2) INFORMATION FOR SEQ ID NO:2:

(i) SEQUENCE CHARACTERISTICS:
         (A) LENGTH: 25 amino acids
         (B) TYPE: amino acid
         (C) STRANDEDNESS: unknown
         (D) TOPOLOGY: linear (ii) MOLECULE TYPE: peptide (xi) SEQUENCE DESCRIPTION: SEQ ID NO:2:

Asp Pro Asp Leu Glu Lys Glu Ala Glu Glu Leu Glu Gln Glu Asn Ala
1               5                  10                  15

Glu Leu Glu Glu Leu Glu Asp Ser Phe
            20                  25

(2) INFORMATION FOR SEQ ID NO:3:

(i) SEQUENCE CHARACTERISTICS:
         (A) LENGTH: 26 amino acids
         (B) TYPE: amino acid
         (C) STRANDEDNESS: unknown
         (D) TOPOLOGY: linear (ii) MOLECULE TYPE: peptide (xi) SEQUENCE DESCRIPTION: SEQ ID NO:3:

Asp Pro Asp Leu Glu Lys Glu Ala Glu Glu Leu Glu Gln Glu Asn Ala
1               5                  10                  15

Glu Leu Glu Glu Glu Leu Glu Asp Ser Phe
            20                  25
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:4:

```
Asp Pro Asp Glu Glu Glu Asp Glu Glu Glu Leu Glu Glu Leu Glu
1               5                   10                  15

Asp Ser Phe
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:5:

```
Asp Pro Asp Leu Glu Glu Leu Glu Asp Ser Phe
1               5                   10
```

(2) INFORMATION FOR SEQ ID NO:6:

(i) SEQUENCE CHARACTERISTICS:
        (A) LENGTH: 210 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:6:

```
CTTCCTACAG ACCCTGCTGA AGAAGCAGCA CGAAAGAGAG AGGTTCGTCT AATGAAGAAC      60

AGGGAAGCAC CAAGAGAATG TCGTAGAAAG AAGAAAGAAT ATGTGAAATG TTTAGAGAAC     120

AGAGTGGCAG TGCTTGAAAA CCAAAAAAAA ACATTGATTG AGGAGCTAAA AGCACTTAAG     180

GACCTTTACT GCCACAAGTC AGATTAATTC                                     210
```

(2) INFORMATION FOR SEQ ID NO:7:

(i) SEQUENCE CHARACTERISTICS:
        (A) LENGTH: 69 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:7:

```
Leu Pro Thr Gln Pro Ala Glu Glu Ala Ala Arg Lys Arg Glu Val Arg
1               5                   10                  15

Leu Met Lys Asn Arg Glu Ala Ala Arg Glu Cys Arg Arg Lys Lys Lys
                20                  25                  30

Glu Tyr Val Lys Cys Leu Glu Asn Arg Val Ala Val Leu Glu Asn Gln
            35                  40                  45

Asn Lys Thr Leu Ile Glu Glu Leu Lys Ala Leu Lys Asp Leu Tyr Cys
50                  55                  60
```

```
His Lys Ser Asp Xaa
 65
```

(2) INFORMATION FOR SEQ ID NO:8:

(i) SEQUENCE CHARACTERISTICS:
        (A) LENGTH: 288 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:8:

```
ATGGACTACA AGGACGACGA TGACAAGCAT ATGGCTAGCA TGACTGGTGG ACAGCAAATG    60

GGTCGGGATC CCCTTCCTAC ACAGCCTGCT GAAGAAGCAG CACGAAAGAG AGAGGTTCGT   120

CTAATGAAGA ACAGGGAAGC AGCAAGAGAA TGTCGTAGAA AGAAGAAAGA ATATGTGAAA   180

TGTTTAGAGA ACAGAGTGGC AGTGCTTGAA AACCAAAACA AAACATTGAT TGAGGAGCTA   240

AAAGCACTTA AGGACCTTTA CTGCCACAAG TCAGATTAAT TCAAGCTT               288
```

(2) INFORMATION FOR SEQ ID NO:9:

(i) SEQUENCE CHARACTERISTICS:
        (A) LENGTH: 93 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:9:

```
Met Lys Tyr Lys Asp Asp Asp Lys His Val Ala Ser Met Thr Gly
 1               5                  10                  15

Gly Gln Gln Met Gly Arg Asp Pro Leu Pro Thr Gln Pro Ala Glu Glu
                20                  25                  30

Ala Ala Arg Lys Arg Glu Val Arg Leu Met Lys Asn Arg Glu Ala Ala
             35                  40                  45

Arg Glu Cys Arg Arg Lys Lys Lys Glu Tyr Val Lys Cys Leu Glu Asn
 50                  55                  60

Arg Val Ala Val Leu Glu Asn Gln Asn Lys Thr Leu Ile Glu Glu Leu
 65                  70                  75                  80

Lys Ala Leu Lys Asp Leu Tyr Cys His Lys Ser Asp Xaa
                 85                  90
```

(2) INFORMATION FOR SEQ ID NO:10:

(i) SEQUENCE CHARACTERISTICS:
        (A) LENGTH: 264 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:10:

```
ATGGACTACA AGGACGACGA TGACAAGCAT ATGGCTAGCA TGACTGGTGG ACAGCAAATG    60

GGTCGGGATC CGGACCTGGA ACAACGTGCT GAGGAACTGG CCCGTGAAAA CGAAGAGCTG   120

GAAAAGAGG CCGAAGAGCT GGAGCAGGAA CTGGCAGAAC TCGAGAACAG AGTGGCAGTG   180

CTTGAAAACC AAAACAAAAC ATTGATTGAG GAGCTAAAAG CACTTAAGGA CCTTTACTGC   240

CACAAGTCAG ATTAATTCAA GCTT                                        264
```

(2) INFORMATION FOR SEQ ID NO:11:

(i) SEQUENCE CHARACTERISTICS:
        (A) LENGTH: 88 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:11:

```
Met Asp Tyr Lys Asp Asp Asp Lys His Met Ala Ser Met Thr Gly
1               5                  10                  15

Gly Gln Gln Met Gly Arg Asp Pro Asp Leu Met Gln Arg Ala Glu Glu
            20                  25                  30

Leu Ala Arg Glu Asn Glu Glu Leu Glu Lys Glu Ala Glu Glu Leu Glu
            35                  40                  45

Gln Glu Leu Ala Glu Leu Glu Asn Arg Val Ala Val Leu Glu Asn Gln
50                  55                  60

Asn Lys Thr Leu Ile Glu Glu Leu Lys Ala Leu Lys Glu Leu Tyr Cys
65                  70                  75                  80

His Lys Ser Asp Xaa Phe Lys Leu
                85
```

(2) INFORMATION FOR SEQ ID NO:12:

(i) SEQUENCE CHARACTERISTICS:
        (A) LENGTH: 262 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:12:

```
GGATCCCAAG GTGGAACAGT TATCTCCAGA AGAAGAAGAG AAAAGGAGAA TCCGAAGGGA      60

AAGGAATAAG ATGGCTGCAG CCAAATGCCG CAACCGGAGG AGGGAGCTGA CTGATACACT     120

CCAAGCGGAG ACAGACCAAC TAGAAGATGA GAAGTCTGCT TTGCAGACCG AGATTGCCAA     180

CCTGCTGAAG GAGAAGGAAA AACTAGAGTT CATCCTGGCA GCTCACCGAC CTGCCTGCAA     240

GATCCCTGAT TAATTCAAGC TT                                              262
```

(2) INFORMATION FOR SEQ ID NO:13:

(i) SEQUENCE CHARACTERISTICS:
        (A) LENGTH: 82 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:13:

```
Pro Asp Lys Val Glu Gln Leu Ser Pro Glu Glu Glu Lys Arg Arg
1               5                  10                  15

Ile Arg Arg Glu Arg Asn Lys Met Ala Ala Ala Lys Cys Arg Asn Arg
            20                  25                  30

Arg Arg Glu Leu Thr Asp Thr Leu Gln Ala Glu Thr Asp Gln Leu Glu
            35                  40                  45

Asp Glu Lys Ser Ala Leu Gln Thr Glu Ile Ala Asn Leu Leu Lys Glu
50                  55                  60

Lys Glu Lys Leu Glu Phe Ile Leu Ala Ala His Arg Pro Ala Cys Lys
```

```
                65                  70                  75                  80
Ile Pro (2) INFORMATION FOR SEQ ID NO:14:

(i) SEQUENCE CHARACTERISTICS:
        (A) LENGTH: 318 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:14:

ATCGACTACA AGGACGACGA TGACAAGCAT ATGGCTAGCA TGACTGGTGG ACAGCAAATG     60

GGTCGGGATC CCAAGGTGGA ACAGTTATCT CCAGAAGAAG AAGAGAAAAG GAGAATCCGA    120

AAGGAAAGGA ATAAGATGGC TGCAGCCAAA TGCCGCAACC GGAGGAGGGA GCTGACTGAT    180

ACACTCCAAG CGGAGACAGA CCAACTAGAA GATGAGAAGT CTGCTTTGCA GACCGAGATT    240

GCCAACCTGC TGAAGGAGAA GGAAAAACTA GAGTTCATCC TGGCAGCTCA CCGACCTGCC    300

TGCAAGATCC CTGATTAA                                                  318

(2) INFORMATION FOR SEQ ID NO:15:

(i) SEQUENCE CHARACTERISTICS:
        (A) LENGTH: 105 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:15:

Met Asp Tyr Lys Asp Asp Asp Lys His Met Ala Ser Met Thr Gly
1               5                  10                  15

Gly Gln Gln Met Gly Arg Asp Pro Lys Val Glu Gln Leu Ser Pro Glu
                20                  25                  30

Glu Glu Glu Lys Arg Arg Ile Arg Arg Glu Arg Asn Lys Met Ala Ala
            35                  40                  45

Ala Lys Cys Arg Asn Arg Arg Arg Glu Leu Thr Asp Thr Leu Gln Ala
        50                  55                  60

Glu Thr Asp Gln Leu Glu Asp Glu Lys Ser Ala Leu Gln Thr Glu Ile
65                  70                  75                  80

Ala Asn Leu Leu Lys Glu Lys Glu Lys Leu Glu Phe Ile Leu Ala Ala
                85                  90                  95

His Arg Pro Ala Cys Lys Ile Pro Asp
                100                 105

(2) INFORMATION FOR SEQ ID NO:16:

(i) SEQUENCE CHARACTERISTICS:
        (A) LENGTH: 281 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:16:

ATATACATAT GGCTAGCATG ACTGGTGGAC AGCAAATGGG TCGGGATCCT GACCTGGAAC     60

AACGTGCTGA GGAACTGGCC CGTGAAAACG AAGAGCTGGA AAAGAGGGCC GAAGAGCTGG    120
```

```
AGCAGGAAAA CGCTGAACTC GAGGCGGAGA CAGACCAACT AGAAGATGAG AAGTCTCCTT      180

TGCAGACCGA GATTGCCAAC CTGCTGAAGG AGAAGGAAAA ACTAGAGTTC ATCCTGGCAG      240

CTCACCGACC TGCCTGCAAG ATCCCTGATT AATTCAAGCT T                         281
```

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:17:

```
Tyr Pro Tyr Asp Val Pro Asp Tyr Ala
1               5
```

(2) INFORMATION FOR SEQ ID NO:18:

(i) SEQUENCE CHARACTERISTICS:
        (A) LENGTH: 294 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:18:

```
ATGGACTACA AGGACGACGA TGACAAGCAT ATGGCTAGCA TGACTGGTGG ACAGCAAATG       60

GGTCGGGATC CTGACCTGGA ACAACGTGCT GAGGAACTGG CCCGTGAAAA CGAAGAGCTG      120

GAAAAGAGG CCGAAGAGCT GGAGCAGGAA AACGCTGAAC TCGAGGCGGA GACAGACCAA       180

CTAGAAGATG AGAAGTCTGC TTTGCAGACC GAGATTGCCA ACCTGCTGAA GGAGAAGGAA      240

AAACTAGAGT TCATCCTGGC AGCTCACCGA CCTGCCTGCA AGATCCCTGA TTAA            294
```

(2) INFORMATION FOR SEQ ID NO:19:

(i) SEQUENCE CHARACTERISTICS:
        (A) LENGTH: 98 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:19:

```
Met Asp Tyr Lys Asp Asp Asp Lys His Met Ala Ser Met Thr Gly
1               5                   10                  15

Gly Gln Gln Met Gly Arg Asp Pro Asp Leu Glu Gln Arg Ala Glu
                20                  25                  30

Leu Ala Arg Glu Asn Glu Glu Leu Glu Lys Lys Ala Glu Glu Leu Glu
            35                  40                  45

Gln Glu Asn Ala Glu Leu Glu Ala Glu Thr Asp Gln Leu Glu Asp Glu
        50                  55                  60

Lys Ser Ala Leu Gln Thr Glu Ile Ala Asn Leu Leu Lys Glu Lys Glu
65                  70                  75                  80

Lys Leu Glu Phe Ile Leu Ala Ala His Arg Pro Ala Cys Lys Ile Pro
                85                  90                  95

Asp Xaa
```

(2) INFORMATION FOR SEQ ID NO:20:

(i) SEQUENCE CHARACTERISTICS:
    (A) LENGTH: 345 base pairs
    (B) TYPE: nucleic acid
    (C) STRANDEDNESS: unknown
    (D) TOPOLOGY: linear (ii) MOLECULE TYPE: DNA (genomic)

(xi) SEQUENCE DESCRIPTION: SEQ ID NO:20:

```
ATCGACTACA AGGACGACGA TGACAAGCAT ATGGCTAGCA TGACTGGTGG ACAGCAAATG    60

GGTCGGGATC CCTCCCCTAT TGACATGGAG TCGCAGGAGA GAATCAAAGC CGAGAGAAAA   120

CGCATGAGAA ACAGAATTGC GGCGTCCAAA TGCCGGAAAA GGAAGTTGGA AAGGATTGCC   180

AGGTTGGAAG AAAAAGTGAA AACTTTGAAA GCCCAGAACT CAGAGCTGGC ATCCACGGCC   240

AACATGCTCA GAGAACAGGT TGCACAGCTT AAGCAGAAGG TCATGAACCA TGTCAACAGC   300

GGGTGCCAGC TAATGCTAAC ACAACAGTTG CAAACGTTTT GATTC                   345
```

(2) INFORMATION FOR SEQ ID NO:21:

(i) SEQUENCE CHARACTERISTICS:
    (A) LENGTH: 115 amino acids
    (B) TYPE: amino acid
    (C) STRANDEDNESS: unknown
    (D) TOPOLOGY: linear (ii) MOLECULE TYPE: peptide (xi) SEQUENCE DESCRIPTION: SEQ ID NO:21:

```
Met Asp Tyr Lys Asp Asp Asp Lys His Met Ala Ser Met Thr Gly
1               5                  10                  15

Gly Gln Gln Met Gly Arg Asp Pro Ser Pro Ile Asp Met Glu Ser Gln
            20                  25                  30

Glu Arg Ile Lys Ala Glu Arg Lys Arg Met Arg Asn Arg Ile Ala Ala
        35                  40                  45

Ser Lys Cys Arg Lys Arg Lys Leu Glu Arg Ile Ala Arg Leu Glu Glu
    50                  55                  60

Lys Val Lys Thr Leu Lys Ala Gln Asn Ser Glu Leu Ala Ser Thr Ala
65                  70                  75                  80

Asn Met Leu Arg Glu Gln Val Ala Gln Leu Lys Gln Lys Val Met Asn
                85                  90                  95

His Val Asn Ser Gly Cys Gln Leu Met Leu Thr Gln Gln Leu Gln Thr
            100                 105                 110

Phe Xaa Phe
        115
```

(2) INFORMATION FOR SEQ ID NO:22:

(i) SEQUENCE CHARACTERISTICS:
    (A) LENGTH: 324 base pairs
    (B) TYPE: nucleic acid
    (C) STRANDEDNESS: unknown
    (D) TOPOLOGY: linear (ii) MOLECULE TYPE: DNA (genomic)

(xi) SEQUENCE DESCRIPTION: SEQ ID NO:22:

```
ATACATATCG CTAGCATGAC TGGTGGACAG CAAATGGGTC GGGATCCCGA CGAAGAGGAA    60

GATGACGAAC AAGAACTCGA GGAACTGGAA GACAGCTTTC ACAGTTTGCG GGACTCAGTC   120

CCATCACTCC AAGGAGAGAA GGCATCCCGG GCCCAAATCC TAGACAAAGC AACAGAGTAT   180

ATCCAGTATA TGCGAAGGAA AAACCATACG CACCAGCAAG ACATTGATGA CCTCAAGCGG   240
```

```
CAGAATGCTC TTCTGGAGCA ACAAGTCCGT GCACTGGAGA AGGCAAGATC AAGTGCCCAA    300

CTGCAGATTT GAGGCAAGCT TATC                                          324
```

(2) INFORMATION FOR SEQ ID NO:23:

(i) SEQUENCE CHARACTERISTICS:
        (A) LENGTH: 98 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:23:

```
Met Ala Ser Met Thr Gly Gly Gln Gln Met Gly Arg Asp Pro Asp Glu
1               5                   10                  15

Glu Glu Asp Asp Glu Glu Glu Leu Glu Glu Leu Glu His Ser Leu Arg
            20                  25                  30

Asp Ser Val Pro Ser Leu Gln Gly Glu Lys Ala Ser Arg Ala Gln Ile
        35                  40                  45

Leu Asp Lys Ala Thr Glu Tyr Ile Gln Tyr Met Arg Arg Lys Asn His
    50                  55                  60

Thr His Gln Gln Asp Ile Asp Asp Leu Lys Arg Gln Asn Ala Leu Leu
65                  70                  75                  80

Glu Gln Gln Val Arg Ala Leu Glu Lys Ala Arg Ser Ser Ala Gln Leu
                85                  90                  95

Gln Thr
```

(2) INFORMATION FOR SEQ ID NO:24:

(i) SEQUENCE CHARACTERISTICS:
        (A) LENGTH: 344 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:24:

```
ATATACATAT GGCTAGCATG ACTGGTGGAC AGCAAATGGG TCGGGATCCT GACCTGGAAA     60

AAGAGGCCGA AGAGCTGGAG CAGGAAAACG CTGAACTCGA GCAACTGGAA GACAGCTTTC    120

ACAGTTTGCG GGACTCAGTC CCATCACTCC AAGGAGAGAA GGCATCCCGG GCCCAAATCC    180

TAGACAAAGC AACAGAGTAT ATCCAGTATA TGCGAAGGAA AAACCATACG CACCAGCAAG    240

ACATTGATGA CCTCAAGCGG CAGAATGCTC TTCTGGAGCA ACAAGTCCGT GCACTGGAGA    300

AGGCAAGATC AAGTGCCCAA CTGCAGACCT GAGGCAAGCT TATC                    344
```

(2) INFORMATION FOR SEQ ID NO:25:

(i) SEQUENCE CHARACTERISTICS:
        (A) LENGTH: 104 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:25:

```
Met Ala Ser Met Thr Gly Gly Gln Gln Met Gly Arg Asp Leu Glu Lys
1               5                   10                  15

Glu Ala Glu Glu Leu Glu Gln Glu Asn Ala Glu Leu Glu Glu Leu Glu
```

```
                  20                  25                  30
Asp Ser Phe His Ser Leu Arg Asp Ser Val Pro Ser Leu Gln Gly Glu
            35                  40                  45

Lys Ala Ser Arg Ala Gln Ile Leu Asp Lys Ala Glu Tyr Ile Gln Tyr
 50                  55                  60

Met Arg Arg Lys Asn His Thr His Gln Gln Asp Ile Asp Asp Leu Lys
 65                  70                  75                  80

Arg Gln Asn Ala Leu Leu Glu Gln Gln Val Arg Ala Leu Glu Lys Ala
                85                  90                  95

Arg Ser Ser Ala Gln Leu Gln Thr
            100
```

(2) INFORMATION FOR SEQ ID NO:26:

(i) SEQUENCE CHARACTERISTICS:
        (A) LENGTH: 341 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:26:

```
ATATACATAT GGCTAGCATG ACTCGTGGAC AGCAAATGGG TCGGGATCCT GACCTGGAAA    60

AAGAGGCCGA AGAGCTGGAG CAGGAAAACG CTGAACTCGA GCTGGAAGAC AGCTTTCACA   120

GTTTGCGGGA CTCAGTCCCA TCACTCCAAG GAGAGAAGGC ATCCCCCGCC CAAATCCTAG   180

ACAAAGCAAC AGAGTATATC CAGTATATGC GAAGGAAAAA CCATACCCAC CAGCAAGACA   240

TTGATGACCT CAAGCGGCAG AATGCTCTTC TGGAGCAACA AGTCCCTGCA CTGGAGAAGG   300

CAAGATCAAC TGCCCAACTG CAGACCTGAG GCAAGCTTAT C                      341
```

(2) INFORMATION FOR SEQ ID NO:27:

(i) SEQUENCE CHARACTERISTICS:
        (A) LENGTH: 88 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:27:

```
Met Cys Ser Met Thr Gly Gly Gln Gln Met Gly Arg Asp Leu Glu Lys
 1               5                  10                  15

Glu Ala Glu Glu Leu Glu Gln Glu Asn Ala Glu Leu Glu Leu Glu Asp
            20                  25                  30

Ser Phe His Ser Leu Arg Asp Ser Val Pro Ser Leu Gln Gly Glu Lys
            35                  40                  45

Ala Ser Arg Ala Gln Ile Leu Asp Lys Ala Thr Glu Asp Asp Leu Lys
 50                  55                  60

Arg Gln Asn Ala Leu Leu Glu Gln Gln Val Arg Ala Leu Glu Lys Ala
 65                  70                  75                  80

Arg Ser Ser Ala Gln Leu Gln Thr
            85
```

(2) INFORMATION FOR SEQ ID NO:28:

(i) SEQUENCE CHARACTERISTICS:
        (A) LENGTH: 347 base pairs
        (B) TYPE: nucleic acid
        (C) STRANDEDNESS: unknown (D) TOPOLOGY: linear (ii) MOLECULE TYPE: DNA (genomic)

(xi) SEQUENCE DESCRIPTION: SEQ ID NO:28:

ATATACATAT GGCTAGCATC ACTGGTGGAC AGCAAATGGG TCGGGATCCT GACCTGGAAA        60

AAGAGGCCGA AGAGCTGGAG CAGGAAAACG CTGAACTCGA GGAAGAGCTG AAGACAGCT        120

TTCACAGTTT GCGGGACTCA GTCCCATCAC TCCAAGGAGA GAAGGCATCC CGGGCCCAAA       180

TCCTAGACAA AGCAACAGAG TATATCCAGT ATATGCGAAG GAAAAACCAT ACGCACCAGC       240

AAGACATTGA TGACCTCAAG CGGCAGAATG CTCTTCTGCA GCAACAAGTC CGTGCACTGG       300

AGAAGGCAAG ATCAAGTGCC CAACTGCAGA CCTGAGGCAA GCTTATC                    347

(2) INFORMATION FOR SEQ ID NO:29:

(i) SEQUENCE CHARACTERISTICS:
        (A) LENGTH: 106 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:29:

Met Ala Ser Met Thr Gly Gly Gln Gln Met Gly Arg Asp Leu Glu Lys
1               5                   10                  15

Glu Ala Glu Glu Leu Glu Gln Glu Asn Ala Glu Leu Glu Gly Glu Leu
            20                  25                  30

Glu Asp Ser Phe His Ser Leu Arg Asp Ser Val Pro Ser Leu Gln Gly
        35                  40                  45

Glu Lys Ala Ser Arg Ala Gln Ile Leu Asp Lys Ala Thr Glu Tyr Ile
    50                  55                  60

Gln Tyr Met Arg Arg Lys Asn His Thr His Gln Asp Ile Asp Asp
65                  70                  75                  80

Leu Lys Arg Gln Asn Ala Leu Leu Glu Gln Gln Val Arg Ala Leu Glu
                85                  90                  95

Lys Ala Arg Ser Ser Ala Gln Leu Gln Thr
            100                 105

(2) INFORMATION FOR SEQ ID NO:30:

(i) SEQUENCE CHARACTERISTICS:
        (A) LENGTH: 277 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:30:

GGATCCCAAC GACAAGAGGC GGACACACAA CGTCTTGGAA CGTCAGAGGA GGAACGACCT        60

GAAGCGCAGC TTTTTTGCCC TGCGTGACCA GATCCCTGAA TTGGAAAACA ACGAAAAGGC       120

CCCCAAGGTA GTGATCCTCA AAAAAGCCAC CGCCTACATC CTGTCCATTC AAGCACACGA       180

GCACAAGCTC ACCTCTGAAA AGGACTTATT GAGGAAACGA CGAGAACAGT TGAAACACAA       240

ACTCGAACAG CTTCGAAACT CTGGTGCATA AAAGCTT                               277

(2) INFORMATION FOR SEQ ID NO:31:

(i) SEQUENCE CHARACTERISTICS:
        (A) LENGTH: 88 amino acids (B) TYPE: amino acid
          (C) STRANDEDNESS: unknown
          (D) TOPOLOGY: linear (ii) MOLECULE TYPE: peptide (xi) SEQUENCE DESCRIPTION: SEQ ID NO:31:

Asn Asp Lys Arg Arg Thr His Asn Val Leu Glu Arg Gln Arg Arg Asn
1               5                   10                  15

Glu Leu Lys Arg Ser Phe Phe Ala Leu Arg Asp Gln Ile Pro Glu Leu
            20                  25                  30

Glu Asn Asn Glu Lys Ala Pro Lys Val Val Ile Leu Lys Lys Ala Thr
        35                  40                  45

Ala Tyr Ile Leu Ser Ile Gln Ala Asp Glu His Lys Leu Thr Ser Glu
50                  55                  60

Lys Asp Leu Leu Arg Lys Arg Glu Gln Leu Lys His Lys Leu Glu
65                  70                  75                  80

Gln Leu Arg Asn Ser Gly Ala Xaa
                85

(2) INFORMATION FOR SEQ ID NO:32:

(i) SEQUENCE CHARACTERISTICS:
          (A) LENGTH: 296 base pairs
          (B) TYPE: nucleic acid
          (C) STRANDEDNESS: unknown
          (D) TOPOLOGY: linear (ii) MOLECULE TYPE: DNA (genomic)

(xi) SEQUENCE DESCRIPTION: SEQ ID NO:32:

ATGGCTAGCA TGACTGGTGG ACAGCAAATG GGTCGGGATC CTGGCGGTGG CCTGGAACAA        60

CGTGCTGAGG AACTGGCCCG TGAAAACGAA GAGCTGGAAA AAGAGGCCGA AGAGCTGGAG       120

CAGGAAAACG CTGAACTCGA GCAGGAAGTG TTGGAGTTGG AAAGTCGTAA TGACCGCCTG       180

CGCAAGGAAG TGGAACAGCT GGAGCGTGAA CTGGACACGC TGCGGGGTAT CTTCCGCCAG       240

CTGCCTGAGA GCTCCTTGGT CAAGGCCATG GGCAACTGCG CGTGAGGCGA ATTCAA          296

(2) INFORMATION FOR SEQ ID NO:33:

(i) SEQUENCE CHARACTERISTICS:
          (A) LENGTH: 13 amino acids
          (B) TYPE: amino acid
          (C) STRANDEDNESS: unknown
          (D) TOPOLOGY: linear (ii) MOLECULE TYPE: peptide (xi) SEQUENCE DESCRIPTION: SEQ ID NO:33:

Ala Ser Met Thr Gly Gly Gln Gln Met Gly Arg Asp Pro
1               5                   10

(2) INFORMATION FOR SEQ ID NO:34:

(i) SEQUENCE CHARACTERISTICS:
          (A) LENGTH: 52 amino acids
          (B) TYPE: amino acid
          (C) STRANDEDNESS: unknown
          (D) TOPOLOGY: linear (ii) MOLECULE TYPE: peptide (xi) SEQUENCE DESCRIPTION: SEQ ID NO:34:

Gly Gly Gly Thr Gln Gln Glu Val Leu Glu Leu Glu Ser Arg Asn Asp
1               5                   10                  15

```
Arg Leu Arg Lys Glu Val Glu Gln Leu Glu Arg Glu Leu Asp Thr Leu
        20                  25                  30

Arg Gly Ile Phe Arg Gln Leu Pro Glu Ser Ser Leu Val Lys Ala Met
            35                  40                  45

Gly Asn Cys Ala
 50
```

(2) INFORMATION FOR SEQ ID NO:35:

(i) SEQUENCE CHARACTERISTICS:
        (A) LENGTH: 12 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:35:

```
Gly Gly Gly Leu Glu Gln Glu Asn Ala Glu Leu Glu
 1               5                  10
```

(2) INFORMATION FOR SEQ ID NO:36:

(i) SEQUENCE CHARACTERISTICS:
        (A) LENGTH: 19 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:36:

```
Gly Gly Gly Leu Glu Lys Glu Ala Glu Glu Leu Glu Gln Glu Asn Ala
 1               5                  10                  15

Glu Leu Glu
```

(2) INFORMATION FOR SEQ ID NO:37:

(i) SEQUENCE CHARACTERISTICS:
        (A) LENGTH: 26 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:37:

```
Gly Gly Gly Leu Ala Arg Glu Asn Glu Glu Leu Glu Lys Glu Ala Glu
 1               5                  10                  15

Glu Leu Glu Gln Glu Asn Ala Glu Leu Glu
            20                  25
```

(2) INFORMATION FOR SEQ ID NO:38:

(i) SEQUENCE CHARACTERISTICS:
        (A) LENGTH: 33 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:38:

```
Gly Gly Gly Leu Glu Gln Arg Ala Glu Glu Leu Ala Arg Glu Asn Glu
 1               5                  10                  15

Glu Leu Glu Lys Glu Ala Glu Glu Leu Glu Gln Glu Asn Ala Glu Leu
```

```
         20                  25                  30
Glu (2) INFORMATION FOR SEQ ID NO:39:

(i) SEQUENCE CHARACTERISTICS:
        (A) LENGTH: 26 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:39:

Gly Gly Gly Leu Ala Arg Asn Asn Ile Ala Val Arg Lys Ser Arg Asp
1               5                   10                  15

Lys Ala Lys Gln Arg Asn Val Glu Leu Glu
            20                  25

(2) INFORMATION FOR SEQ ID NO:40:

(i) SEQUENCE CHARACTERISTICS:
        (A) LENGTH: 26 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:40:

Gly Gly Gly Leu Ala Arg Asn Asn Ile Ala Leu Arg Lys Ser Ala Asp
1               5                   10                  15

Lys Leu Lys Gln Arg Asn Val Glu Leu Glu
            20                  25

(2) INFORMATION FOR SEQ ID NO:41:

(i) SEQUENCE CHARACTERISTICS:
        (A) LENGTH: 26 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:41:

Gly Gly Gly Leu Ala Arg Glu Asn Ile Ala Val Glu Lys Glu Arg Asp
1               5                   10                  15

Lys Ala Glu Gln Glu Asn Val Glu Leu Glu
            20                  25

(2) INFORMATION FOR SEQ ID NO:42:

(i) SEQUENCE CHARACTERISTICS:
        (A) LENGTH: 26 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:42:

Gly Gly Gly Leu Ala Arg Asn Asn Glu Glu Val Arg Lys Ser Arg Glu
1               5                   10                  15

Glu Ala Lys Gln Arg Asn Ala Glu Leu Glu
            20                  25
```

(2) INFORMATION FOR SEQ ID NO:43:

(i) SEQUENCE CHARACTERISTICS:
        (A) LENGTH: 141 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:43:

```
Ser Glu Tyr Gln Pro Ser Leu Phe Ala Leu Asn Pro Met Gly Phe Ser
 1               5                  10                  15

Pro Leu Asp Gly Ser Lys Ser Thr Asn Glu Asn Val Ser Ala Ser Thr
            20                  25                  30

Ser Thr Ala Lys Pro Met Val Gly Gln Leu Ile Phe Asp Lys Phe Ile
        35                  40                  45

Lys Thr Glu Glu Asp Pro Gly Lys Ala Lys Lys Ser Val Asp Lys Asn
 50                  55                  60

Ser Asn Glu Tyr Arg Val Arg Arg Glu Arg Asn Asn Ile Ala Val Arg
65                  70                  75                  80

Lys Ser Arg Asp Lys Ala Lys Gln Arg Asn Val Glu Thr Gln Gln Lys
                85                  90                  95

Val Leu Glu Leu Thr Ser Asp Asn Asp Arg Leu Arg Lys Arg Val Glu
            100                 105                 110

Gln Leu Ser Arg Glu Leu Asp Thr Leu Arg Gly Ile Phe Arg Gln Leu
        115                 120                 125

Pro Glu Ser Ser Leu Val Lys Ala Met Gly Asn Cys Ala
    130                 135                 140
```

(2) INFORMATION FOR SEQ ID NO:44:

(i) SEQUENCE CHARACTERISTICS:
        (A) LENGTH: 83 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:44:

```
Pro Val Lys Asp Glu Arg Glu Leu Lys Arg Gln Lys Arg Lys Gln Ser
 1               5                  10                  15

Asn Arg Glu Ser Ala Arg Arg Ser Arg Leu Arg Asn Gln Ala Glu Cys
            20                  25                  30

Glu Gln Thr Gln Gln Lys Val Leu Glu Leu Thr Ser Asp Asn Asp Arg
        35                  40                  45

Leu Arg Lys Arg Val Glu Gln Leu Ser Arg Glu Leu Asp Thr Leu Arg
 50                  55                  60

Gly Ile Phe Arg Gln Leu Pro Glu Ser Ser Leu Val Lys Ala Met Gly
65                  70                  75                  80

Asn Cys Ala
```

(2) INFORMATION FOR SEQ ID NO:45:

(i) SEQUENCE CHARACTERISTICS:
        (A) LENGTH: 102 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:45:

Ala Ser Met Thr Gly Gly Gln Gln Met Gly Arg Asp Pro Leu Glu Glu
1               5                   10                  15

Lys Val Phe Val Pro Asp Glu Gln Lys Asp Glu Lys Tyr Trp Thr Arg
            20                  25                  30

Arg Lys Lys Asn Asn Val Ala Ala Lys Arg Ser Arg Asp Ala Arg Arg
        35                  40                  45

Leu Lys Glu Asn Gln Thr Gln Gln Lys Val Leu Glu Leu Thr Ser Asp
    50                  55                  60

Asn Asp Arg Leu Arg Lys Arg Val Glu Gln Leu Ser Arg Glu Leu Asp
65                  70                  75                  80

Thr Leu Arg Gly Ile Phe Arg Gln Leu Pro Glu Ser Ser Leu Val Lys
                85                  90                  95

Ala Met Gly Asn Cys Ala
            100

(2) INFORMATION FOR SEQ ID NO:46:

(i) SEQUENCE CHARACTERISTICS:
        (A) LENGTH: 28 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:46:

GTCAGTCAGA TTGCGCAATA TCGGTCAG                                          28

(2) INFORMATION FOR SEQ ID NO:47:

(i) SEQUENCE CHARACTERISTICS:
        (A) LENGTH: 10 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:47:

ATTGCGCAAT                                                              10

(2) INFORMATION FOR SEQ ID NO:48:

(i) SEQUENCE CHARACTERISTICS:
        (A) LENGTH: 13 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:48:

Met Asp Tyr Lys Asp Asp Asp Lys Lys Lys Arg Lys
1               5                   10

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:49:

Tyr Pro Tyr Asp Val Pro Asp Tyr Ala
1               5

(2) INFORMATION FOR SEQ ID NO:50:

(i) SEQUENCE CHARACTERISTICS:
        (A) LENGTH: 8 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:50:

Asp Tyr Lys Asp Asp Asp Asp Lys
1               5

(2) INFORMATION FOR SEQ ID NO:51:

(i) SEQUENCE CHARACTERISTICS:
        (A) LENGTH: 11 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:51:

Ala Ser Met Thr Gly Gly Gln Gln Met Gly Arg
1               5                   10

(2) INFORMATION FOR SEQ ID NO:52:

(i) SEQUENCE CHARACTERISTICS:
        (A) LENGTH: 89 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:52:

Met Ala Ser Met Thr Gly Gly Gln Gln Met Gly Arg Asp Pro Gly Gly
1               5                   10                  15

Gly Leu Glu Gln Arg Ala Glu Glu Leu Ala Arg Glu Asn Glu Glu Leu
                20                  25                  30

Glu Lys Glu Ala Glu Glu Leu Glu Gln Glu Asn Ala Glu Leu Glu Gln
            35                  40                  45

Glu Val Leu Glu Leu Glu Ser Arg Asn Asp Arg Leu Arg Lys Glu Val
    50                  55                  60

Glu Gln Leu Glu Arg Glu Leu Asp Thr Leu Arg Gly Ile Phe Arg Gln
65                  70                  75                  80

Leu Pro Glu Ser Ser Leu Val Lys Ala
                85

(2) INFORMATION FOR SEQ ID NO:53:

(i) SEQUENCE CHARACTERISTICS:
        (A) LENGTH: 34 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:53:

Asp Pro Asp Leu Glu Gln Arg Ala Glu Glu Leu Ala Arg Glu Asn Glu
1               5                  10                  15

Glu Leu Glu Lys Glu Ala Glu Glu Leu Gln Glu Asn Ala Glu Leu
            20                  25                  30

Glu Gln (2) INFORMATION FOR SEQ ID NO:54:

(i) SEQUENCE CHARACTERISTICS:
        (A) LENGTH: 34 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:54:

Asp Pro Asp Leu Glu Gln Arg Ala Glu Glu Leu Ala Arg Glu Asn Glu
1               5                  10                  15

Glu Leu Glu Lys Glu Ala Glu Glu Leu Gln Glu Leu Ala Glu Leu
            20                  25                  30

Glu Gln (2) INFORMATION FOR SEQ ID NO:55:

(i) SEQUENCE CHARACTERISTICS:
        (A) LENGTH: 31 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:55:

Arg Ile Lys Ala Glu Arg Lys Arg Met Arg Asn Arg Ile Ala Ala Ser
1               5                  10                  15

Lys Cys Arg Lys Arg Lys Leu Glu Arg Ile Ala Arg Leu Glu Glu
            20                  25                  30

(2) INFORMATION FOR SEQ ID NO:56:

(i) SEQUENCE CHARACTERISTICS:
        (A) LENGTH: 31 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:56:

Ser Asn Glu Tyr Arg Val Arg Arg Glu Arg Asn Asn Ile Ala Val Arg
1               5                  10                  15

Lys Ser Arg Asp Lys Ala Lys Gln Arg Asn Val Glu Thr Gln Gln
            20                  25                  30

(2) INFORMATION FOR SEQ ID NO:57:

(i) SEQUENCE CHARACTERISTICS:
        (A) LENGTH: 34 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:57:

Gly Gly Gly Leu Glu Gln Arg Ala Glu Glu Leu Ala Arg Glu Asn Glu
1               5                   10                  15

Glu Leu Glu Lys Glu Ala Glu Glu Leu Glu Gln Glu Asn Ala Glu Leu
                20                  25                  30

Glu Gln (2) INFORMATION FOR SEQ ID NO:58:

(i) SEQUENCE CHARACTERISTICS:
        (A) LENGTH: 31 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:58:

Ser Asn Glu Tyr Arg Val Arg Arg Glu Arg Asn Asn Ile Ala Val Arg
1               5                   10                  15

Lys Ser Arg Asp Lys Ala Lys Gln Arg Asn Val Glu Thr Gln Gln
                20                  25                  30

(2) INFORMATION FOR SEQ ID NO:59:

(i) SEQUENCE CHARACTERISTICS:
        (A) LENGTH: 31 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:59:

Asp Glu Lys Tyr Trp Thr Arg Arg Lys Lys Asn Asn Val Ala Ala Lys
1               5                   10                  15

Arg Ser Arg Asp Ala Arg Arg Leu Lys Glu Asn Gln Thr Gln Gln
                20                  25                  30

(2) INFORMATION FOR SEQ ID NO:60:

(i) SEQUENCE CHARACTERISTICS:
        (A) LENGTH: 31 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:60:

Glu Leu Lys Arg Gln Lys Arg Lys Gln Ser Asn Arg Glu Ser Ala Arg
1               5                   10                  15

Arg Ser Arg Leu Arg Lys Gln Ala Glu Cys Glu Gln Leu Gln Gln
                20                  25                  30

What is claimed is:

1. An isolated DNA molecule encoding an acidically modified nucleic acid binding protein containing an N-terminal extension of acidic amino acid residues, thereby forming an acidic N-terminal extension of a protein-protein interaction surface of a dimerization or multimerization surface of said acidically modified protein, said acidic N-terminal extension allowing said acidically modified protein to stably dimerize or multimerize with a normal cellular protein.

2. An isolated DNA molecule encoding an acidically modified nucleic acid binding protein comprising a dimerization or multimerization domain having appended N-terminally thereto an N-terminal extension of acidic amino acid residues, wherein said N-terminal exension of acidic amino acid residues replaces a basic nucleic acid binding domain in said acidically modified nucleic acid binding protein, and further wherein said N-terminal extension of said acidically modified protein allows said acidically modified protein to stably dimerize or multimerize with a cellular protein.

3. The DNA molecule according to claim 1 or claim 2, wherein said encoded acidically modified nucleic acid binding protein is an acidically modified DNA binding protein.

4. The DNA molecule according to claim 3, wherein said encoded acidically modified DNA binding protein is an acidically modified bZIP protein.

5. The DNA molecule according to claim 4, wherein said encoded acidically modified bZIP protein is selected from the group consisting of Fos, Jun, GCN4, LRF-1, VBP, GBF-, opaque, DBP, CHOP-10, CREB, C/EBP, PAR, ATF2, and plant G-box protein.

6. The DNA molecule according to claim 3, wherein said encoded acidically modified nucleic acid binding protein is an acidically modified basic helix-loop-helix (bHLH) protein.

7. The DNA molecule according to claim 6, wherein said acidically modified bHLH protein is selected from the group consisting of c-myc, n-myc, i-myc, max, mad, ID, MyoD1, E12, AP-4, TFE3, USF, and FIP.

8. The DNA molecule according to claim 1 or claim 2, wherein said acidic amino acid residues of said encoded acidically modified nucleic acid binding protein are glutamic acid or aspartic acid.

9. The DNA molecule according to claim 1 or claim 2, wherein said acidic extension of said encoded acidically modified nucleic acid binding protein comprises from two to one-hundred amino acid residues.

10. The DNA molecule according to claim 9, wherein said acidic extension of said encoded acidically modified nucleic acid binding protein comprises from three to fifty amino acid residues.

11. The DNA molecule according to claim 10, wherein said acidic extension of said encoded acidically modified nucleic acid binding protein comprises from three to thirty amino acid residues.

12. The DNA molecule according to claim 11, wherein said acidic extension of said encoded acidically modified nucleic acid binding protein comprises twenty-eight amino acid residues.

13. The DNA molecule according to claim 1 or claim 2, wherein said acidic extension of said encoded acidically modified nucleic acid binding protein is amphipathic.

14. The DNA molecule according to claim 1 or claim 2, wherein said encoded acidically modified nucleic acid binding protein inhibits the activation of endogenous activator molecules.

15. The DNA molecule according to claim 3, wherein said acidic extension of said encoded acidically modifed nucleic acid binding protein replaces the basic region of said DNA binding protein.

16. The DNA molecule according to claim 1 or claim 2, wherein said encoded acidically modified nucleic acid binding protein is a transcription regulating protein.

17. The DNA molecule according to claim 1 or claim 2, wherein said encoded acidically modified nucleic acid binding protein is an acidically modified RNA binding protein.

18. The DNA molecule according to claim 1 or claim 2, wherein said encoded acidic amino acid residues dimerize with the basic region of a cellular DNA binding protein to inhibit the binding of said protein to DNA.

19. The DNA molecule according to claim 1 or claim 2, wherein said encoded acidic amino acid residues dimerize with the basic region of a cellular RNA binding protein to inhibit the binding of said protein to RNA.

20. The DNA molecule according to claim 1 or claim 2, wherein said acidic N-terminal extension of said acidically modified protein replaces a basic nucleic acid binding region of a dimeric or multimeric nucleic acid binding protein.

21. The DNA molecule according to claim 20, wherein said acidically modified nucleic acid binding protein is an acidically modified DNA or an RNA binding protein.

22. The DNA molecule according to claim 1 or claim 2, wherein at least one amino acid comprising the acidic N-terminal extension is an acidic amino acid.

23. The DNA molecule according to claim 1 or claim 2, wherein two or more amino acids comprising the acidic N-terminal extension are acidic amino acids.

24. The DNA molecule according to claim 1 or claim 2, wherein all of the amino acids comprising the acidic N-terminal extension are acidic amino acids.

25. The DNA molecule according to claim 1 or claim 2, wherein the N-terminal acidic extension comprises repeating domains of amino acids having at least one acidic amino acid in each repeating domain.

26. The DNA molecule according to claim 25, wherein said repeating domains are heptad repeats.

27. The DNA molecule according to claim 1 or claim 2, wherein said acidic N-terminal extension comprises an N-terminal amino acid cap.

28. The DNA molecule according to claim 27, wherein said N-terminal amino acid cap comprises an aspartic acid residue and a proline residue.

29. The DNA molecule according to claim 28, wherein said N-terminal amino acid cap further comprises three glycine residues.

30. The DNA molecule according to claim 28, wherein said N-terminal amino acid cap further comprises two aspartic acid residues.

31. The DNA molecule according to claim 28, wherein said N-terminal amino acid cap further comprises three glutamic acid residues.

32. The DNA molecule according to claim 1 or claim 2, wherein said acidic extension of said encoded acidically modified nucleic acid binding protein comprises form three to thirteen amino acid residues.

33. An isolated DNA molecule encoding an acidically modified nucleic acid binding protein containing an N-terminal extension of acidic amino acid residues, thereby forming an acidic N-terminal extension of a protein-protein interaction surface, or of a dimerization or multimerization surface, of said acidically modified protein, said encoded acidically modified protein containing said acidic N-terminal extension being a dominant negative to a naturally occurring cell protein.

34. The DNA molecule according to claim 1 consisting of the sequence as shown in any one of SEQ ID NOS: 6, 10, 14, 16, 18, 22, 24, 26, 28, or 32.

35. The DNA molecule according to claim 2 consisting of the sequence as shown in any one of SEQ ID NOS: 6, 10, 14, 16, 18, 22, 24, 26, 28, or 32.

36. The DNA molecule according to claim 33 consisting of the sequence as shown in any one of SEQ ID NOS: 6, 10, 14, 16, 18, 22, 24, 26, 28, or 32.

37. The DNA molecule according to claim 1, claim 34, claim 36, or claim 2, said encoded acidically modified nucleic acid binding protein being a dominant negative to a naturally occurring cellular protein.

38. A plasmid vector construct comprising the DNA molecule according to claim 1 or claim 2, a promoter, a transcription initiation site, a transcription termination site, an origin of replication site, and a polyadenylation site, for expression in eukaryotic cells.

39. The vector according to claim 38, wherein said eukaryotic cells are selected from the group consisting of plant cells, yeast cells, and mammalian cells.

40. A plasmid vector construct comprising the DNA molecule according to claim 1 or claim 2, a promoter, a transcription initiation site and a transcription termination site for expression in prokaryotic cells.

41. The construct according to claim 38, wherein said promoter is tissue specific.

42. A plasmid vector construct comprising the DNA molecule according to claim 1 or claim 2, a cell- or tissue-specific promoter, being inducible or noninducible, a transcription initiation site, a transcription termination site, an origin of replication site, and a polyadenylation site, for expression in host cells.

43. A viral vector construct comprising the DNA molecule according to claim 1 or claim 2, for expression in host cells.

44. The viral vector construct according to claim 43, wherein said vector is selected from the group consisting of Simian Virus 40 (SV40) virus vector, adenovirus vector, vaccinia virus vector and adeno-associated virus vector.

45. The vector according to claim 44, wherein said virus vector is an adenovirus vector.

46. The vector according to claim 42, wherein said host cells are eukaryotic cells.

47. The vector according to claim 43, wherein said host cells are eukaryotic cells.

48. The vector according to claim 46, wherein said eukaryotic cells are selected from the group consisting of plant cells, yeast cells and mammalian cells.

49. The vector according to claim 47, wherein said eukaryotic cells are selected from the group consisting of plant cells, yeast cells and mammalian cells.

* * * * *

UNITED STATES PATENT AND TRADEMARK OFFICE
CERTIFICATE OF CORRECTION

PATENT NO. : 5,942,433
DATED : August 24, 1999
INVENTOR(S) : C. Vinson et al.

It is certified that error appears in the above-identified patent and that said Letters Patent is hereby corrected as shown below:

Column 7,
Line 64, replace "DPDLEKEAEELEQENAELEELEDSF" with
-- DPDLEKEAEELEQENAELEEELEDSF --.

Column 75,
Line 63, after "interaction surface" insert -- or --.

Column 78,
Line 36, delete "form" and insert -- from --.

Signed and Sealed this

Eleventh Day of March, 2003

JAMES E. ROGAN
*Director of the United States Patent and Trademark Office*